US011466021B2

(12) United States Patent
Parham et al.

(10) Patent No.: US 11,466,021 B2
(45) Date of Patent: Oct. 11, 2022

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Dominik Joosten, Frankfurt am Main (DE); Aurélie Ludemann, Frankfurt am Main (DE); Tobias Grossmann, Darmstadt (DE); Jonas Kroeber, Frankfurt am Main (DE); Christian Eickhoff, Mannheim (DE)

(73) Assignee: MERCK PATENT GMBH, Darmstadt (DE)

( * ) Notice: Subject to any disclaimer, the term of this patent is extended or adjusted under 35 U.S.C. 154(b) by 697 days.

(21) Appl. No.: 16/463,608

(22) PCT Filed: Dec. 4, 2017

(86) PCT No.: PCT/EP2017/081291
§ 371 (c)(1),
(2) Date: May 23, 2019

(87) PCT Pub. No.: WO2018/104194
PCT Pub. Date: Jun. 14, 2018

(65) Prior Publication Data
US 2020/0199138 A1  Jun. 25, 2020

(30) Foreign Application Priority Data
Dec. 5, 2016  (EP) .................................. 16202146

(51) Int. Cl.
*C07D 491/16* (2006.01)
*C07D 471/16* (2006.01)
*C07D 471/06* (2006.01)
*C07D 471/22* (2006.01)
*H01L 51/00* (2006.01)
*H01L 51/42* (2006.01)

(52) U.S. Cl.
CPC ......... *C07D 491/16* (2013.01); *C07D 471/06* (2013.01); *C07D 471/16* (2013.01); *C07D 471/22* (2013.01); *H01L 51/0067* (2013.01); *H01L 51/0068* (2013.01); *H01L 51/0072* (2013.01); *H01L 51/4273* (2013.01)

(58) Field of Classification Search
None
See application file for complete search history.

(56) References Cited

U.S. PATENT DOCUMENTS

| 5,432,172 A | 7/1995 | Spector et al. |
| 9,741,942 B2 | 8/2017 | Stoessel et al. |
| 2009/0004485 A1 | 1/2009 | Zheng et al. |
| 2017/0077416 A1 | 3/2017 | Kim et al. |
| 2017/0352820 A1 | 12/2017 | Kim et al. |

FOREIGN PATENT DOCUMENTS

| KR | 20150065381 A | 6/2015 |
| KR | 20150065383 A | 6/2015 |
| WO | WO-2014056567 A1 | 4/2014 |
| WO | WO-2016006791 A1 | 1/2016 |

OTHER PUBLICATIONS

Gellerman et al. (Tetrahedron Lett. (1993), 34(11), 1827-30).*
"11-(4-Chlorophenyl)-2,12,15-triazapentacyclo[11.7.1.03.8.09.21.014.19]henicosa-1,3,5,79,11,13(21),14(19),15,17-decaen-20-one", PubChem, 2020, pp. 1-6_54608997.
"11-(2-Methoxyphenyl)-2,12,15-triazapentacyclo[11.7.1.03.8.0921.014,19]henicosa-1,3,5,7,9,11,13(21),14(19),15,17-decaen-20-one", PubChem, 2020, pp. 1-6_54608996.
"11-(4-Methylphenyl)-2,12,15-triazapentacyclo[11.7.03,8,09,21,014,19]henicosa-1,3,5,7,9,11,13(21),14(19),15,17-decaen-20-one", PubChem, 2020, pp. 1-6_54608995.
"11-(4-Nitrophenyl)-2,12,15-triazapentacyclo[11.7.1.03,8.0921.014,19] henicosa-1,3,5,7,9,11,13(21),14(19),15,17-decaen-20-one", PubChem, 2020, pp. 1-6_54608965.
"11-(3-Methoxyphenyl)-2,12,15-triazapentacyclo[11.7.1.03,8.09,21.014,19]henicosa-1,3,5,7,9,11,13(21),14(19),15,17-decaen-20-one", PubChem, 2020, pp. 1-6_54608964.
"11-(4-Chlorophenyl-2,12,15-triazapentacyclo[11,7,1,03,8,09,21,014,19] henicosa-1,3,5,7,9,11,13(21),14(19),15,17-decaen-20-one", PubChem, 2020, pp. 1-6_54608892.
International Search Report for PCT/EP2017/081291 dated Feb. 6, 2018.
Written Opinion of the International Searching Authority for PCT/EP2017/081291 dated Feb. 6, 2018.

* cited by examiner

*Primary Examiner* — Jay Yang
(74) *Attorney, Agent, or Firm* — Faegre Drinker Biddle & Reath LLP

(57) ABSTRACT

The present invention relates to compounds suitable for use in electronic devices, and to electronic devices, especially organic electroluminescent devices, comprising these compounds.

12 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2017/081291, filed. Dec. 4, 2017, which claims benefit of European Application No. 16202146.3, filed Dec. 5, 2016, both of which are incorporated herein by reference in their entirety.

The present invention relates to materials for use in electronic devices, especially in organic electroluminescent devices, and to electronic devices, especially organic electroluminescent devices comprising these materials.

Emitting materials used in organic electroluminescent devices (OLEDs) are frequently organometallic complexes which exhibit phosphorescence rather than fluorescence. For quantum-mechanical reasons, up to four times the energy efficiency and power efficiency is possible using organometallic compounds as phosphorescent emitters. In general terms, however, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials and the charge transport properties thereof can thus also lead to distinct improvements in the OLED properties.

It is an object of the present invention to provide compounds suitable for use in an OLED, especially as matrix material for phosphorescent emitters. A further problem addressed by the present invention is that of providing further organic semiconductors for organic electroluminescent devices, in order thus to enable the person skilled in the art to have a greater possible choice of materials for the production of OLEDs.

It has been found that, surprisingly, particular compounds described below achieve this object and are of good suitability for use in OLEDs and lead to improvements in the organic electroluminescent device. These improvements relate particularly to the lifetime, efficiency and/or operating voltage. The present invention therefore provides these compounds and electronic devices, especially organic electroluminescent devices, comprising such compounds.

The present invention therefore provides a compound of formula (1)

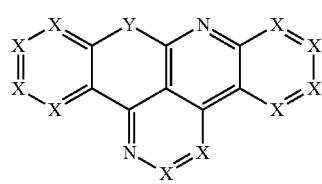

Formula (1)

where the symbols and indices used are as follows:
X is the same or different at each instance and is CR or N;
Y is NR', C(R")$_2$, C=O, BR', O or S;
R, R" are the same or different at each instance and are H, D, F, Cl, Br, I, N(R$^1$)$_2$, NAr$_2$, CN, NO$_2$, OR$^1$, SR$^1$, COOR$^1$, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl group having 1 to 20 carbon atoms or an alkenyl or alkynyl group having 2 to 20 carbon atoms or a branched or cyclic alkyl group having 3 to 20 carbon atoms and where the alkyl, alkenyl or alkynyl group may in each case be substituted by one or more R$^1$ radicals, where one or more nonadjacent CH$_2$ groups may be replaced by Si(R$^1$)$_2$, C=O, NR$^1$, O, S or CONR$^1$, or an aromatic or heteroaromatic ring system which has 5 to 60 aromatic ring atoms, preferably 5 to 40 aromatic ring atoms, and may be substituted in each case by one or more R$^1$ radicals; at the same time, two R radicals together may also form an aliphatic or heteroaliphatic ring system; in addition, two R" radicals together may also form an aliphatic, heteroaliphatic, aromatic or heteroaromatic ring system;

R' is an aromatic or heteroaromatic ring system which has 5 to 40 aromatic ring atoms and may be substituted by one or more R$^1$ radicals;

Ar is the same or different at each instance and is an aromatic or heteroaromatic ring system which has 5 to 40 aromatic ring atoms and may be substituted by one or more R$^1$ radicals;

R$^1$ is the same or different at each instance and is H, D, F, Cl, Br, I, N(R$^2$)$_2$, CN, NO$_2$, OR$^2$, SR$^2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R$^2$ radicals and where one or more nonadjacent CH$_2$ groups may be replaced by Si(R$^2$)$_2$, C=O, NR$^2$, O, S or CONR$^2$, or an aromatic or heteroaromatic ring system which has 5 to 40 aromatic ring atoms and may be substituted in each case by one or more R$^2$ radicals; at the same time, two or more R$^1$ radicals together may form a ring system;

R$^2$ is the same or different at each instance and is H, D, F or an aliphatic, aromatic or heteroaromatic organic radical, especially a hydrocarbyl radical, having 1 to 20 carbon atoms, in which one or more hydrogen atoms may also be replaced by F;

with the proviso that the compound of the formula (1) contains at least one substituent R' and/or that the compound of the formula (1) contains at least one substituent R selected from the group consisting of NAr$_2$ and an aromatic or heteroaromatic ring system which has 5 to 60 aromatic ring atoms and may be substituted by one or more R$^1$ radicals;

where the following compounds are excluded from the invention:

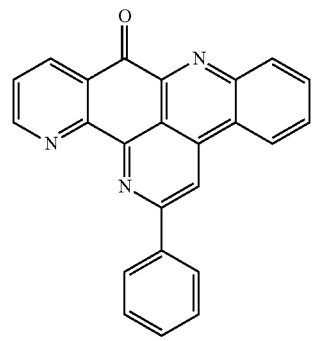

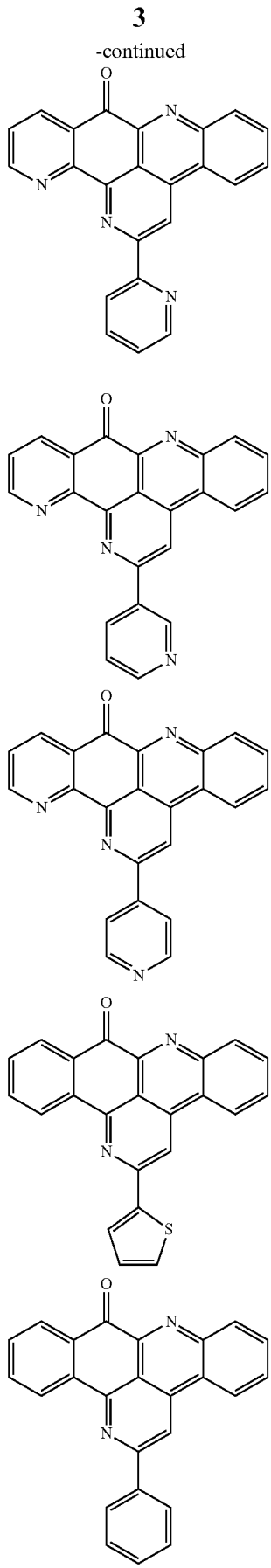
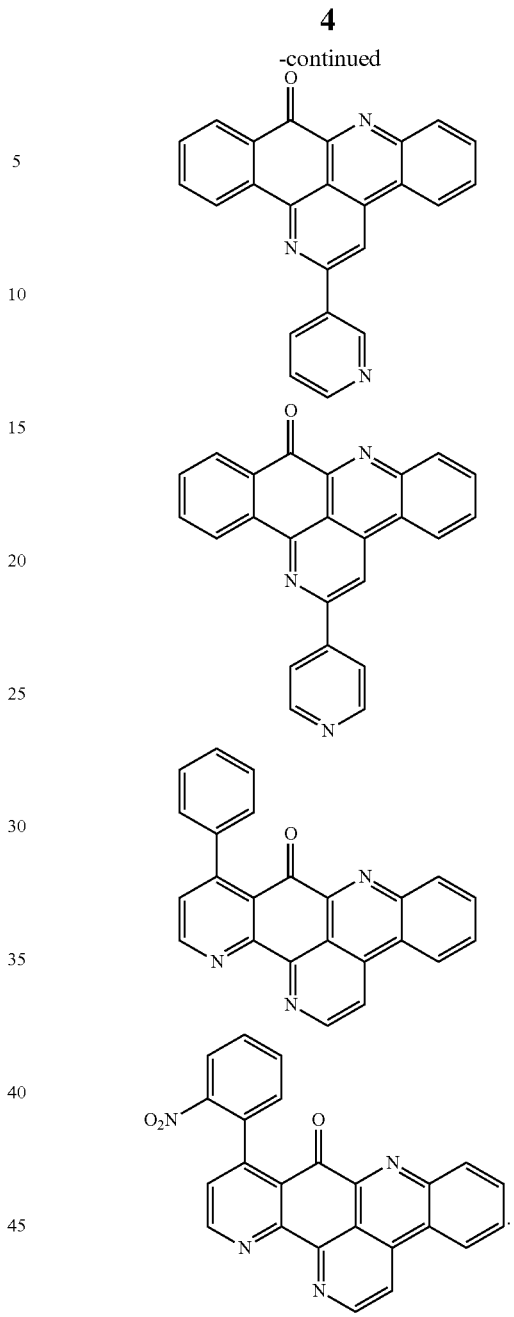

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylflourene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems.

When two R or R" or $R^1$ radicals together form a ring system, it may be mono- or polycyclic, and aliphatic, heteroaliphatic, or else, for R" or $R^1$ radicals, aromatic or heteroaromatic. In this case, the radicals which together form a ring system are preferably adjacent, meaning that these radicals are bonded to the same carbon atom or to carbon atoms directly bonded to one another.

The wording that two or more radicals together may form a ring, in the context of the present description, shall be understood to mean, inter alis, that the two radicals are joined to one another by a chemical bond with formal elimination of two hydrogen atoms. This is illustrated by the following scheme:

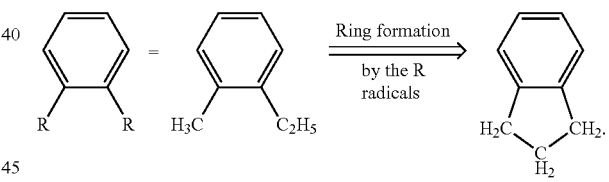

In addition, however, the abovementioned wording shall also be understood to mean that, if one of the two radicals is hydrogen, the second radical binds to the position to which the hydrogen atom was bonded, forming a ring. This shall be illustrated by the following scheme:

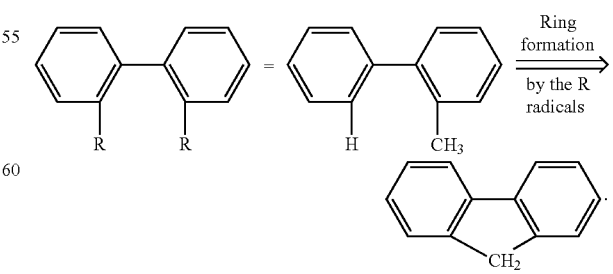

In a preferred embodiment of the invention, Y is NR', O or S, more preferably NR' or O and most preferably NR'.

Compounds with Y=C=O are especially suitable as an intermediate, for example for the synthesis of the corresponding Spiro compounds.

Preference is thus given to a compound of one of the following formulae (1') and (1''):

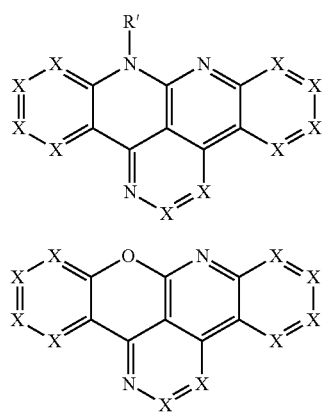

Formula (1')

Formula (1'')

where X has the definitions given above and the compound of the formula (1'') has at least one R radical selected from the group consisting of $NAr_2$ and an aromatic or heteroaromatic ring system. Particular preference is given here to the compound of the formula (1').

In a preferred embodiment, compounds of the formula (1), (1') or (1'') have not more than two nitrogen atoms per ring, meaning that a maximum of two symbols X per ring are N, or a maximum of one symbol X in the ring with the nitrogen atom explicitly shown is N. Preferably, the compounds contain a maximum of one nitrogen atom per ring, meaning that a maximum of one symbol X per ring is N, or none of the symbols X in the ring with the nitrogen atom explicitly shown is N. More preferably, a total of not more than two symbols X are N; in particular, not more than one symbol X is N. Most preferably, all symbols X are CR.

Preference is given to the compounds of the formulae (2a) to (2k)

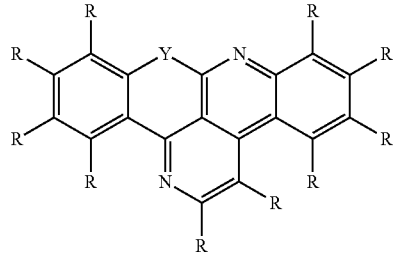

Formula (2a)

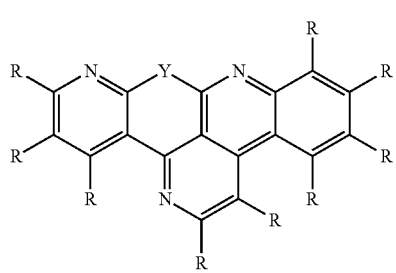

Formula (2b)

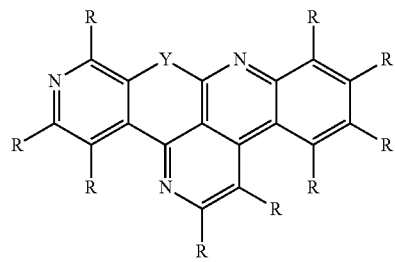

Formula (2c)

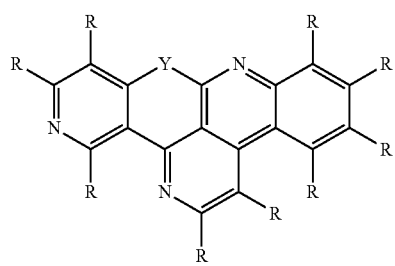

Formula (2d)

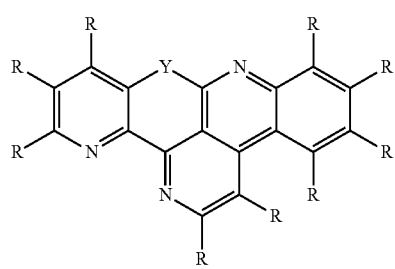

Formula (2e)

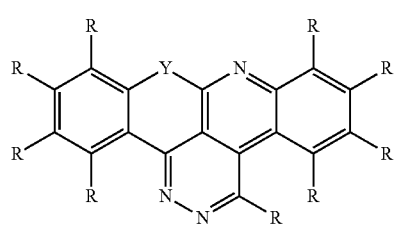

Formula (2f)

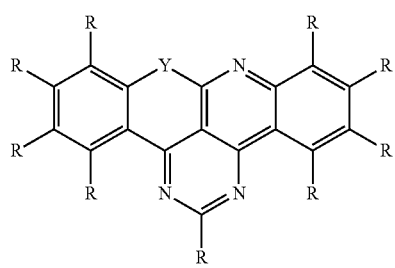

Formula (2g)

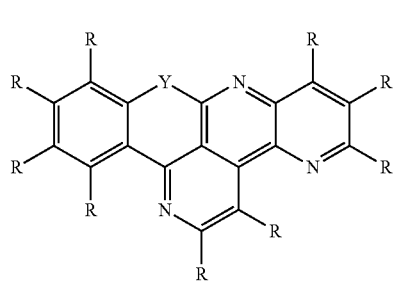

Formula (2h)

-continued

Formula (2i)
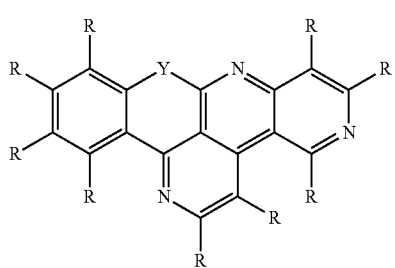

Formula (2j)
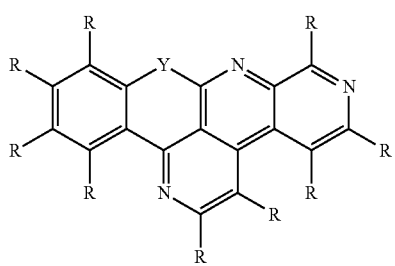

Formula (2k)
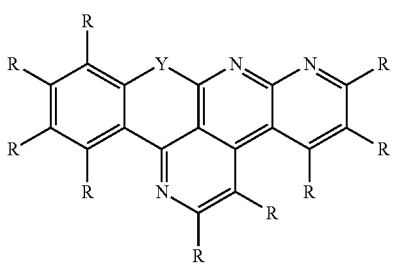

where the symbols used have the definitions given above.
Preference is given to the compounds of the formulae (2a) to (2e) and (2h) to (2k). Particular preference is given to the compound of the formula (2a). Very particular preference is given to the compounds of the formula (2a') or (2a")

Formula (2a')
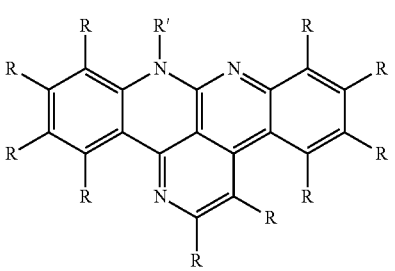

Formula (2a")
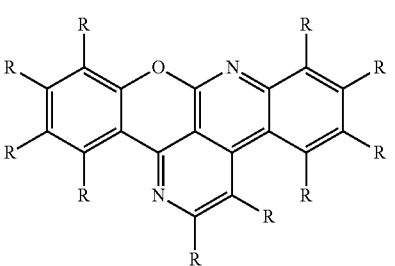

where R and R' have the definitions given above and at least one R group in formula (2a") is selected from the group consisting of $NAr_2$ and an aromatic or heteroaromatic ring system.

A preferred embodiment of the compounds of the formula (2a) is the compounds of the following formula (3):

Formula (3)
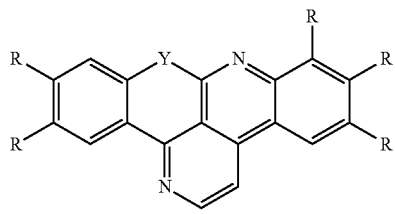

where the symbols used have the definitions given above.
Particular preference is given to the compounds of the formulae (3') and (3")

Formula (3')
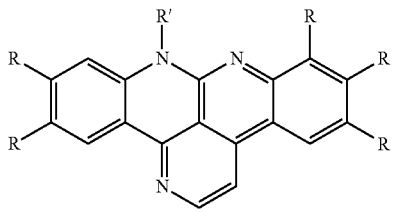

Formula (3")
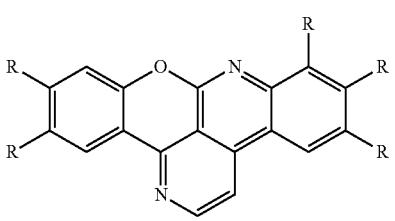

where R and R' have the definitions given above and at least one R group in formula (3") is selected from the group consisting of $NAr_2$ and an aromatic or heteroaromatic ring system.

A preferred embodiment of the compounds of the formula (3) is the compounds of the following formula (4):

Formula (4)

where the symbols used have the definitions given above.
Particular preference is given to the compounds of the formulae (4') and (4")

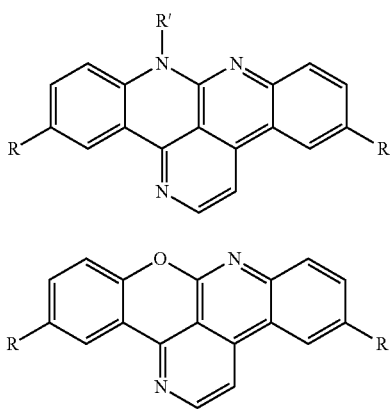

Formula (4')

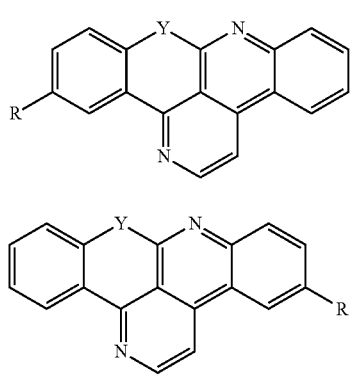

Formula (4")

where R and R¹ have the definitions given above and at least one R group in formula (4") is selected from the group consisting of NAr₂ and an aromatic or heteroaromatic ring system.

Particular preference is given to the compounds of the following formulae (5) and (6):

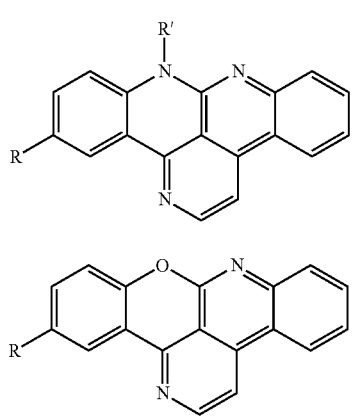

Formula (5)

Formula (6)

where the symbols used have the definitions given above.

Very particular preference is given to the compounds of the formulae (5'), (5"), (6') and (6")

Formula (5')

Formula (5")

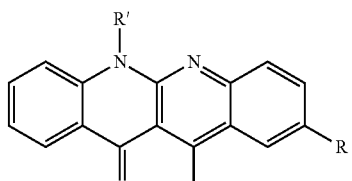

Formula (6')

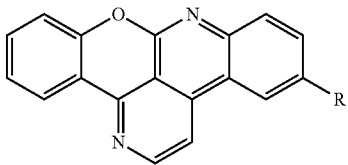

Formula (6")

where R and R' have the definitions given above and the R group in formulae (5") and (6") is selected from the group consisting of NAr₂ and an aromatic or heteroaromatic ring system.

There follows a description of preferred substituents R and R' in the compounds of the invention.

In a preferred embodiment of the invention, R is the same or different at each instance and is selected from the group consisting of H, D, F, NAr₂, CN, OR¹, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R¹ radicals, and where one or more nonadjacent CH₂ groups may be replaced by O, or an aromatic or heteroaromatic ring system which has 6 to 30 aromatic ring atoms and may be substituted in each case by one or more R¹ radicals; at the same time, two R radicals together may also form an aliphatic ring system. More preferably, R is the same or different at each instance and is selected from the group consisting of H, NAr₂, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more R¹ radicals, but is preferably unsubstituted, or an aromatic or heteroaromatic ring system which has 6 to 24 aromatic ring atoms and may be substituted in each case by one or more preferably nonaromatic R¹ radicals. Most preferably, R is the same or different at each instance and is selected from the group consisting of H or an aromatic or heteroaromatic ring system which has 6 to 24 aromatic ring atoms and may be substituted in each case by one or more preferably nonaromatic R¹ radicals.

In a further preferred embodiment of the invention, R' is an aromatic or heteroaromatic ring system which has 6 to 30 aromatic ring atoms and may be substituted by one or more R¹ radicals. In a particularly preferred embodiment of the invention, R' is an aromatic or heteroaromatic ring system which has 6 to 24 aromatic ring atoms and may be substituted by one or more preferably nonaromatic R¹ radicals.

In a further preferred embodiment of the invention, R¹ is the same or different at each instance and is selected from the group consisting of H, D, F, CN, OR², a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R² radicals, and where one or more nonadjacent CH₂ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, an alkyl group having 1 to 4 carbon atoms or an aryl group having 6 to 10 carbon atoms, which may be substituted by an alkyl group having 1 to 4 carbon atoms, but is preferably unsubstituted.

As described above, the compound of the invention contains at least one R' group, and/or it contains at least one substituent R selected from the group consisting of $NAr_2$ and an aromatic or heteroaromatic ring system which has 5 to 60 aromatic ring atoms and which may be substituted by one or more $R^1$ radicals. When Y=NR', it may be preferable when the base skeleton is unsubstituted, i.e. when R=H.

There follows a description of preferred aromatic and heteroaromatic ring systems which may be present as substituent R and/or R' or as Ar group within the $NAr_2$ substituent in the compound of the invention.

Suitable aromatic or heteroaromatic ring systems R, R' or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, phenanthrene, triphenylene or a combination of two or three of these groups, each of which may be substituted by one or more $R^1$ radicals.

The R, R' and Ar groups here are preferably selected from the groups of the following formulae Ar-1 to Ar-75:

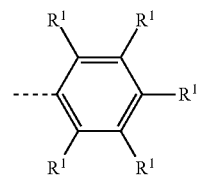

Ar-1

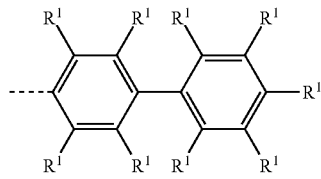

Ar-2

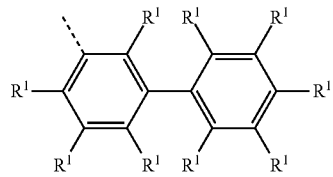

Ar-3

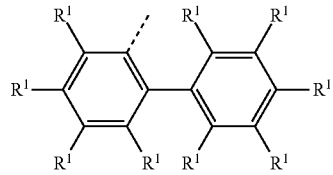

Ar-4

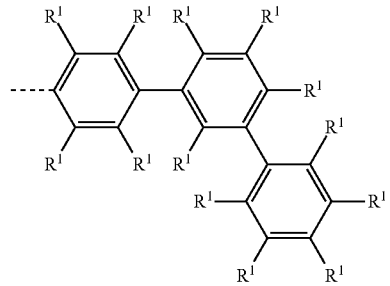

Ar-5

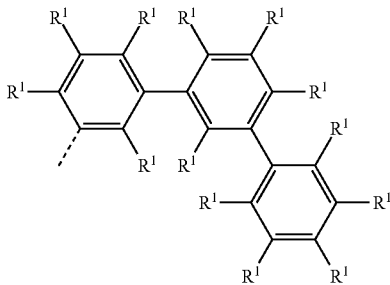

Ar-6

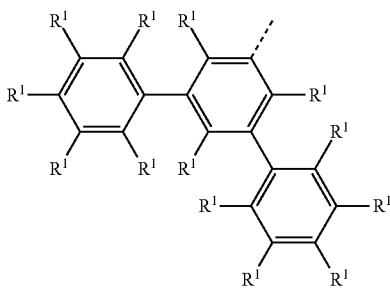

Ar-7

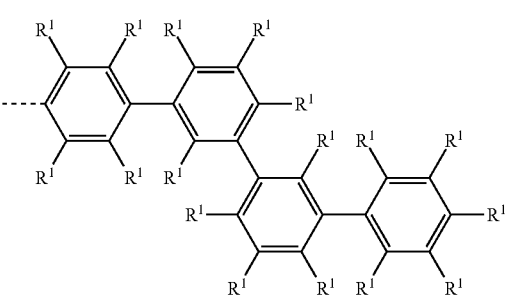

Ar-8

-continued
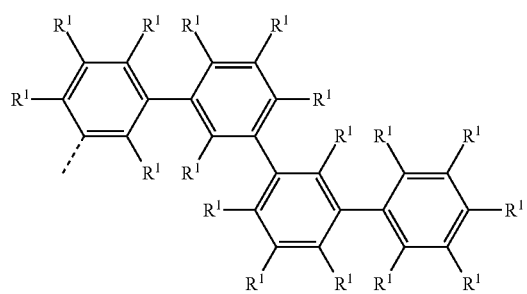
Ar-9
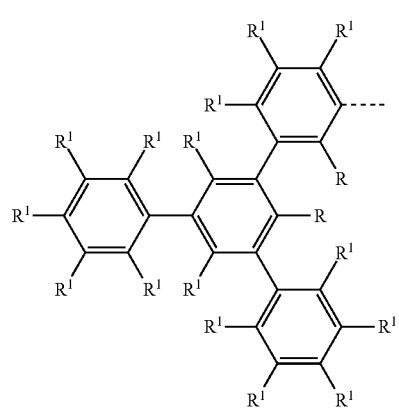
Ar-10
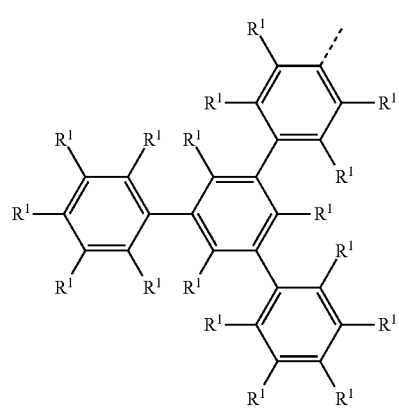
Ar-11
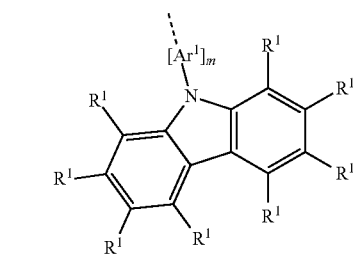
Ar-12
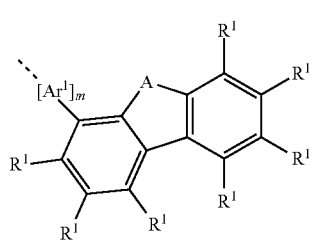
Ar-13
-continued
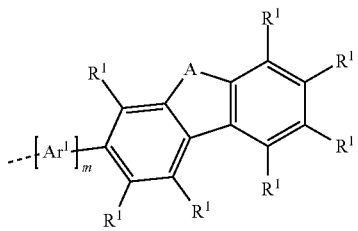
Ar-14
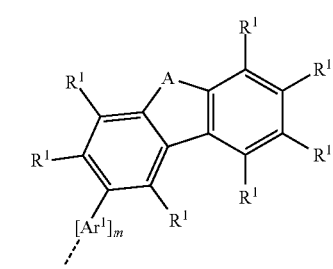
Ar-15
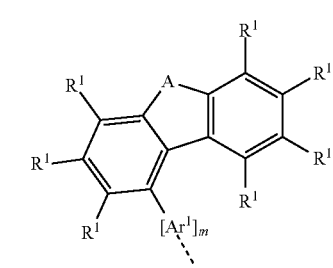
Ar-16
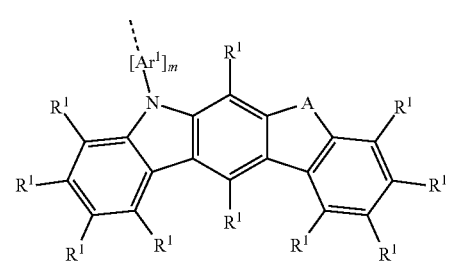
Ar-17
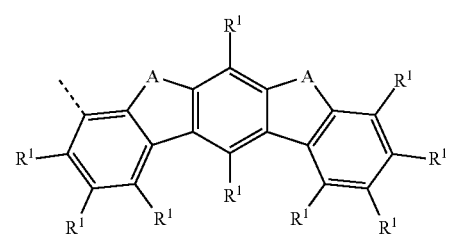
Ar-18
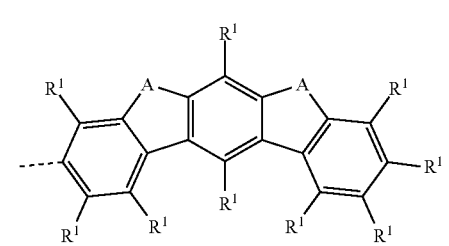
Ar-19

Ar-20
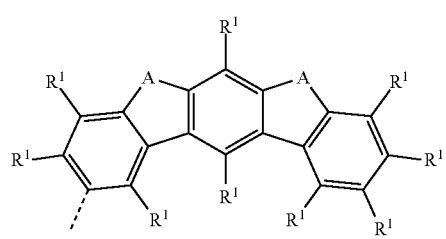
Ar-21
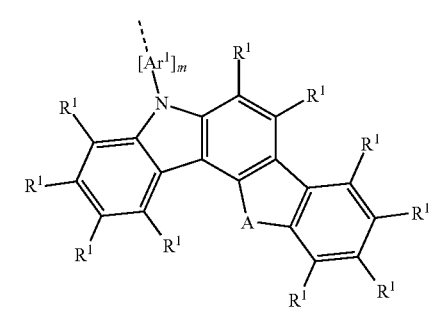
Ar-22
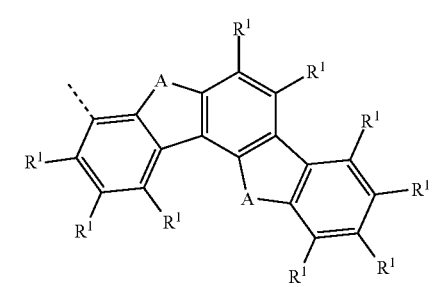
Ar-23
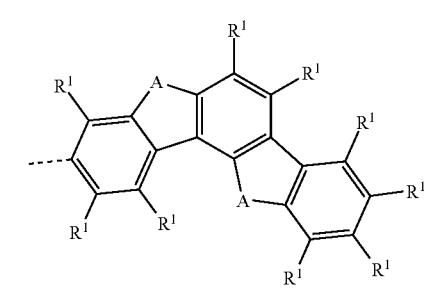
Ar-24
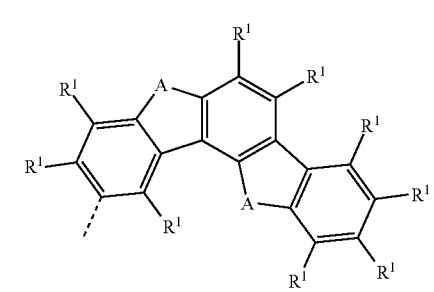
Ar-25
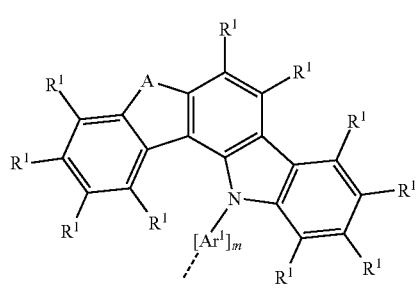
Ar-26
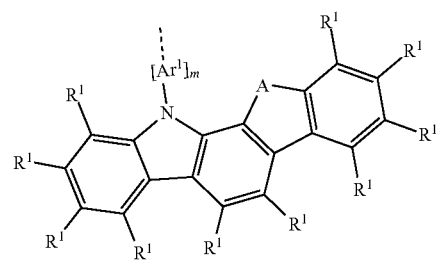
Ar-27
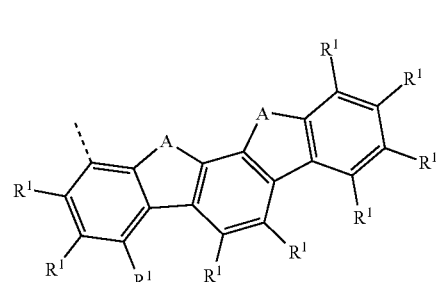
Ar-28
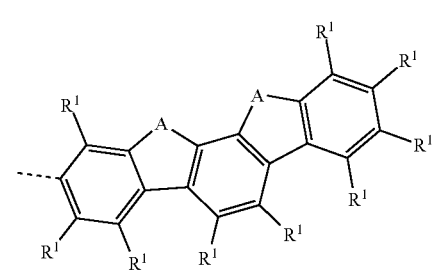
Ar-29
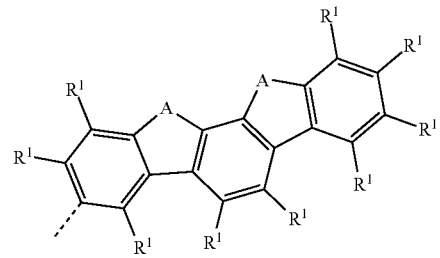
Ar-30
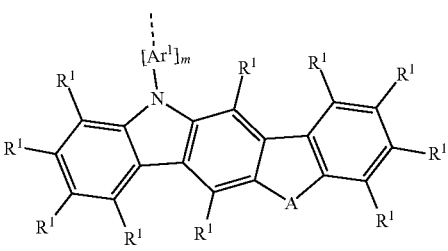

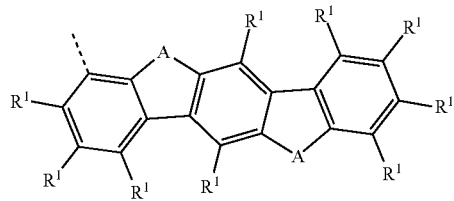
Ar-31
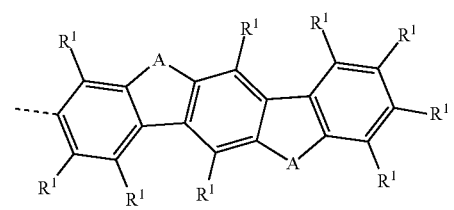
Ar-32
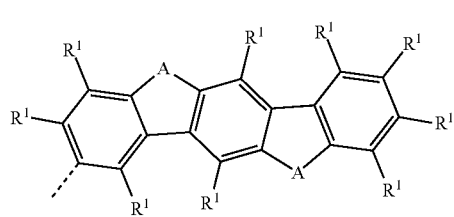
Ar-33
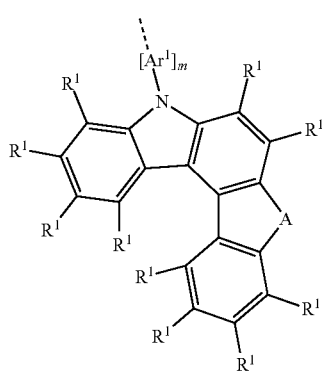
Ar-34
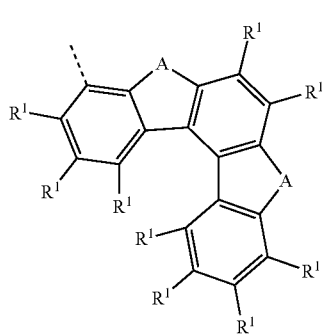
Ar-35
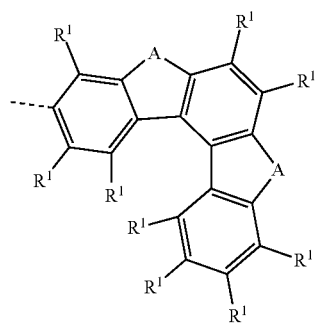
Ar-36
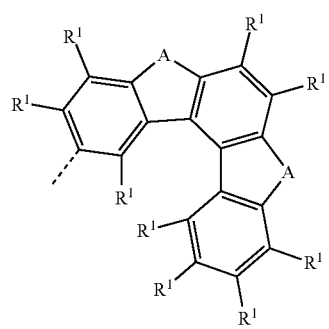
Ar-37
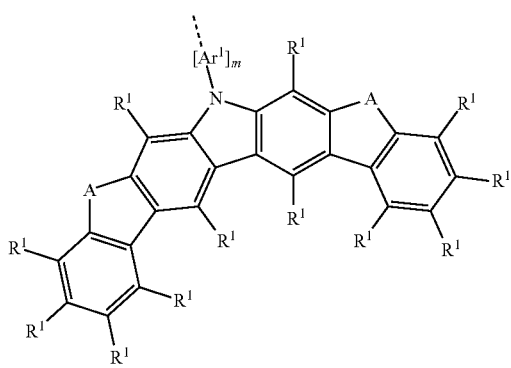
Ar-38
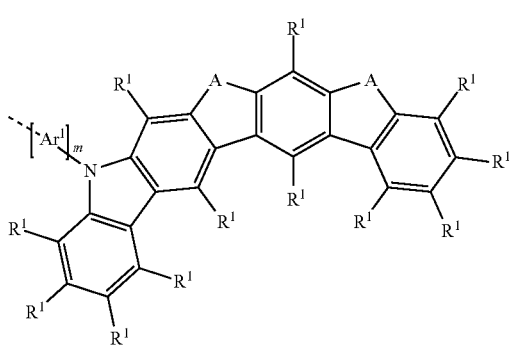
Ar-39

-continued
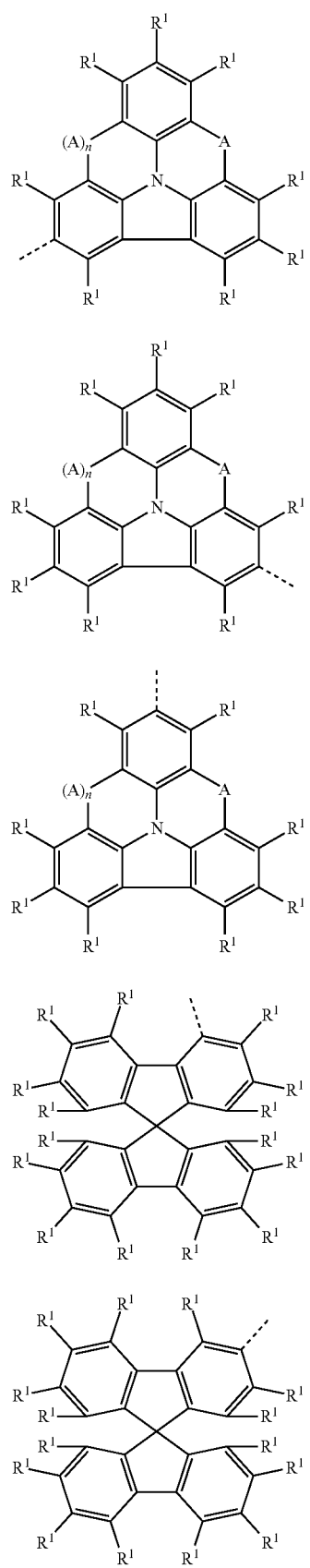
Ar-40
Ar-41
Ar-42
Ar-43
Ar-44
-continued
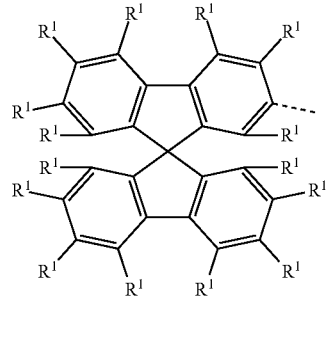
Ar-45
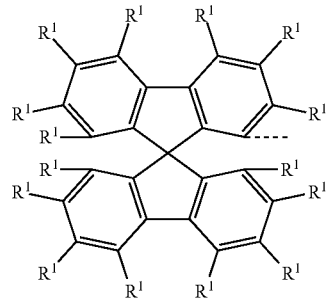
Ar-46
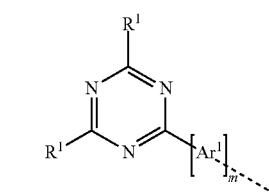
Ar-47
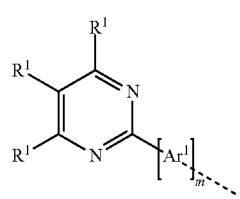
Ar-48
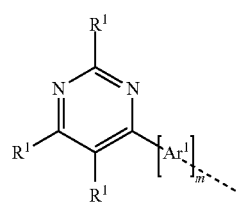
Ar-49
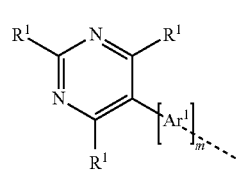
Ar-50
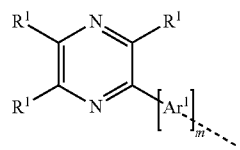
Ar-51

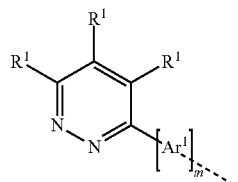 Ar-52
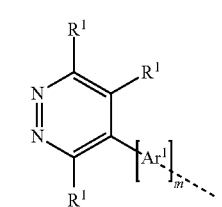 Ar-53
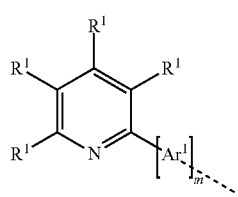 Ar-54
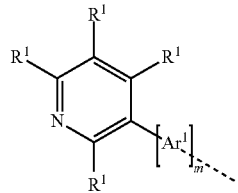 Ar-55
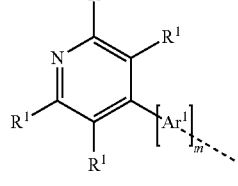 Ar-56
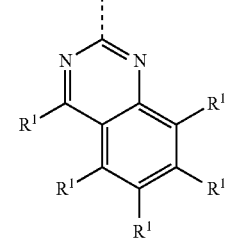 Ar-57
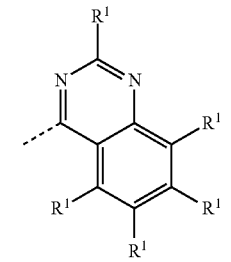 Ar-58
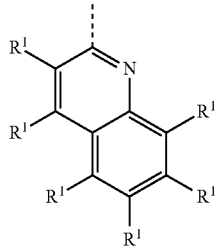 Ar-59
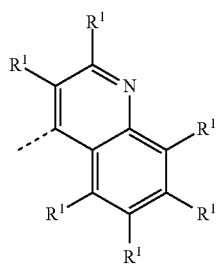 Ar-60
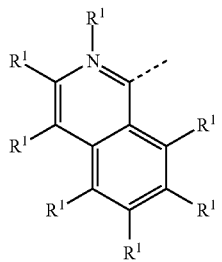 Ar-61
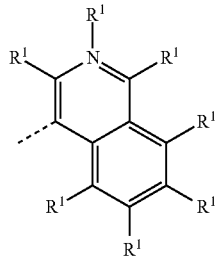 Ar-62
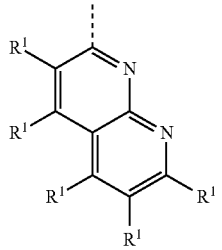 Ar-63
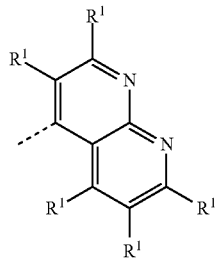 Ar-64

Ar-65 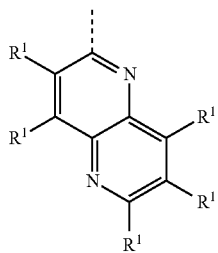

Ar-66 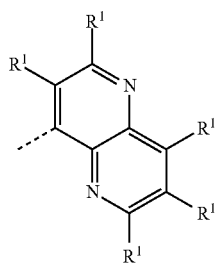

Ar-67 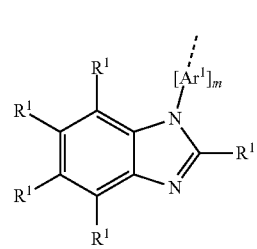

Ar-68 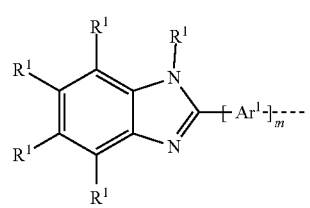

Ar-69 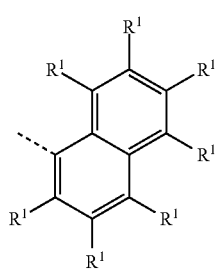

Ar-70 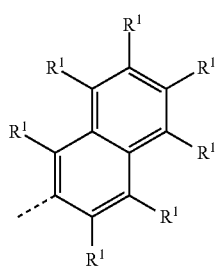

Ar-71 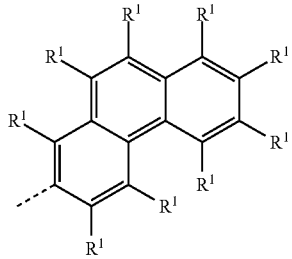

Ar-72 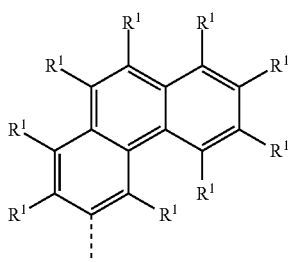

Ar-73 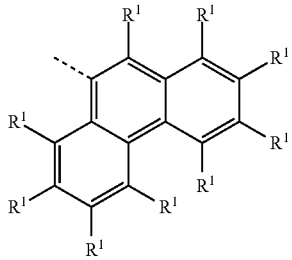

Ar-74 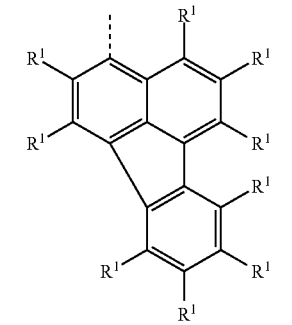

Ar-75 where R¹ has the definitions given above, the dotted bond represents the bond to Y or to a carbon atom of the base skeleton in formula (1) or in the preferred embodiments or to the nitrogen atom in the NAr₂ group and, in addition:

Ar¹ is the same or different at each instance and is a bivalent aromatic or heteroaromatic ring system which has 6 to 18 aromatic ring atoms and may be substituted in each case by one or more R radicals;

A is the same or different at each instance and is $C(R^1)_2$, $NR^1$, O or S;

n is 0 or 1, where n=0 means that no A group is bonded at this position and $R^1$ radicals are bonded to the corresponding carbon atoms instead;

m is 0 or 1, where m=0 means that the $Ar^1$ group is absent and that the corresponding aromatic or heteroaromatic group is bonded directly to Y or a carbon atom of the base skeleton in formula (1) or in the preferred embodiments, or to the nitrogen atom in the $NAr_2$ group; with the proviso that m=1 for the structures (Ar-12), (Ar-17), (Ar-21), (Ar-25), (Ar-26), (Ar-30), (Ar-34), (Ar-38) and (Ar-39) when these groups are embodiments of R' or Ar.

When the abovementioned groups for R, R' or Ar have two or more A groups, possible options for these include all combinations from the definition of A. Preferred embodiments in that case are those in which one A group is $NR^1$ and the other A group is $C(R^1)_2$ or in which both A groups are $NR^1$ or in which both A groups are O. In a particularly preferred embodiment of the invention, in R, R' or Ar groups having two or more A groups, at least one A group is $C(R^1)_2$ or is $NR^1$.

When A is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this substituent $R^1$ is the same or different at each instance and is an aromatic or heteroaromatic ring system which has 6 to 24 aromatic ring atoms, which does not have any fused aryl groups and which does not have any fused heteroaryl groups in which two or more aromatic or heteroaromatic 6-membered ring groups are fused directly to one another, and which may also be substituted in each case by one or more $R^2$ radicals. Particular preference is given to phenyl, biphenyl, terphenyl and quaterphenyl having bonding patterns as listed above for Ar-1 to Ar-11, where these structures may be substituted by one or more $R^2$ radicals, but are preferably unsubstituted.

When A is $C(R^1)_2$, the substituents $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more $R^2$ radicals. Most preferably, $R^1$ is a methyl group or a phenyl group. In this case, the $R^1$ radicals together may also form a ring system, which leads to a Spiro system.

Further suitable R, R' or Ar groups are groups of the formula $-Ar^4-N(Ar^2)(Ar^3)$ where $Ar^2$, $Ar^3$ and $Ar^4$ are the same or different at each instance and are an aromatic or heteroaromatic ring system which has 5 to 24 aromatic ring atoms and may be substituted in each case by one or more $R^1$ radicals. The total number of aromatic ring atoms in $Ar^2$, $Ar^3$ and $Ar^4$ here is not more than 60 and preferably not more than 40.

In this case, $Ar^4$ and $Ar^2$ may also be bonded to one another and/or $Ar^2$ and $Ar^3$ to one another by a group selected from $C(R^1)_2$, $NR^1$, O and S. Preferably, $Ar^4$ and $Ar^2$ are joined to one another and $Ar^2$ and $Ar^3$ to one another in the respective ortho position to the bond to the nitrogen atom. In a further embodiment of the invention, none of the $Ar^2$, $Ar^3$ and $Ar^4$ groups are bonded to one another.

Preferably, $Ar^4$ is an aromatic or heteroaromatic ring system which has 6 to 24 aromatic ring atoms, preferably 6 to 12 aromatic ring atoms, and may be substituted in each case by one or more $R^1$ radicals. More preferably, $Ar^4$ is selected from the group consisting of ortho-, meta- or para-phenylene or ortho-, meta- or para-biphenyl, each of which may be substituted by one or more $R^1$ radicals, but are preferably unsubstituted. Most preferably, $Ar^4$ is an unsubstituted phenylene group. This is especially true when $Ar^4$ is bonded to $Ar^2$ via a single bond.

Preferably, $Ar^2$ and $Ar^3$ are the same or different at each instance and are an aromatic or heteroaromatic ring system which has 6 to 24 aromatic ring atoms and may be substituted in each case by one or more $R^1$ radicals. Particularly preferred $Ar^2$ and $Ar^3$ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more $R^1$ radicals. More preferably, $Ar^2$ and $Ar^3$ are the same or different at each instance and are an aromatic ring system which has 6 to 24 aromatic ring atoms and may be substituted by one or more $R^1$ radicals, especially selected from the groups consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

At the same time, in compounds of the invention that are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta- or para-terphenyl or quaterphenyl or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the R, R', Ar, $R^1$ and $R^2$ radicals do not contain any fused aryl or heteroaryl groups in which two or more six-membered rings are fused directly to one another. An exception to this is formed by phenanthrene and triphenylene which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

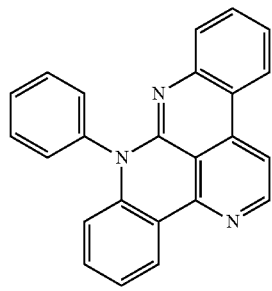 [SMILES: c1ccc(N2c3ccccc3-c3nccc4c3c2nc2ccccc24)cc1]
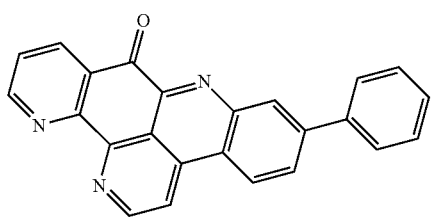 [SMILES: O=C1c2cccnc2-c2nccc3c2c1nc1cc(-c2ccccc2)ccc13]
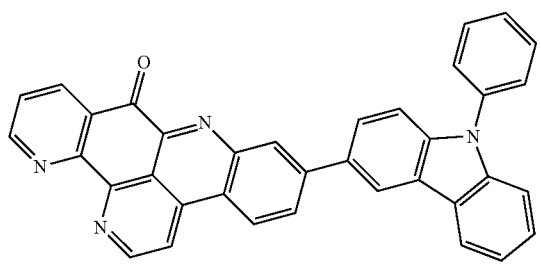 [SMILES: O=C1c2cccnc2-c2nccc3c2c1nc1cc(-c2ccc4c(c2)c2ccccc2n4-c2ccccc2)ccc13]
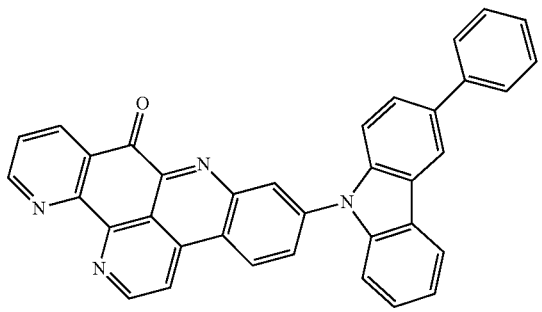 [SMILES: O=C1c2cccnc2-c2nccc3c2c1nc1cc(-n2c4ccccc4c4cc(-c5ccccc5)ccc42)ccc13]
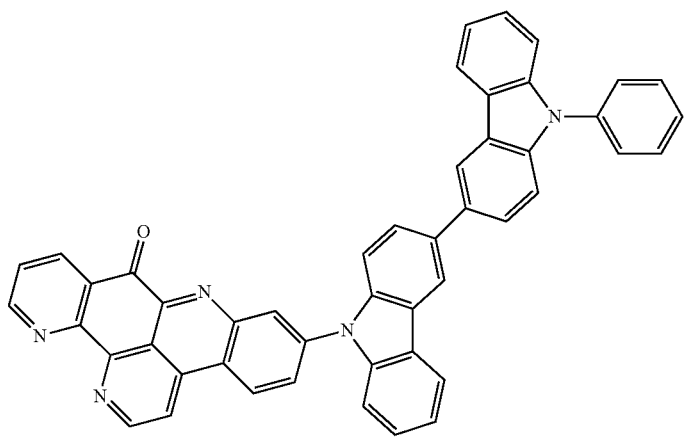 [SMILES: O=C1c2cccnc2-c2nccc3c2c1nc1cc(-n2c4ccccc4c4cc(-c5ccc6c(c5)c5ccccc5n6-c5ccccc5)ccc42)ccc13]

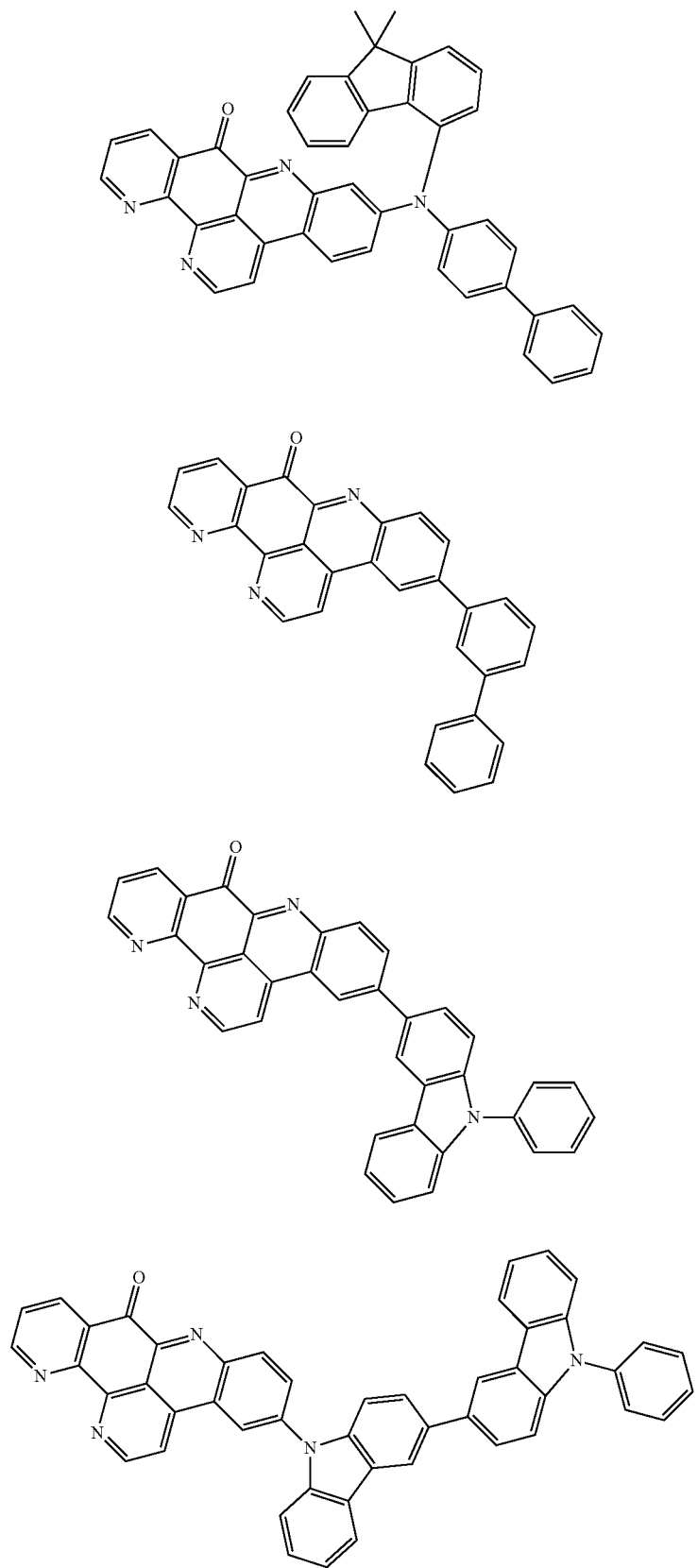

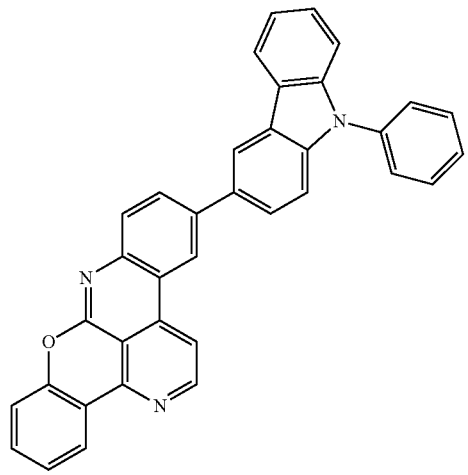 [SMILES: c1ccc(-n2c3ccccc3c3cc(-c4ccc5nc6c7c(nccc7c5c4)-c4ccccc4O6)ccc32)cc1]
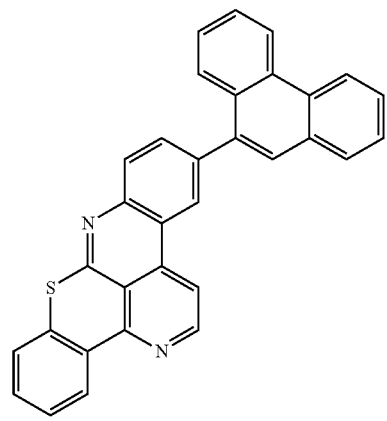 [SMILES: c1ccc2c(c1)Sc1nc3ccc(-c4cc5ccccc5c5ccccc45)cc3c3ccnc-2c13]
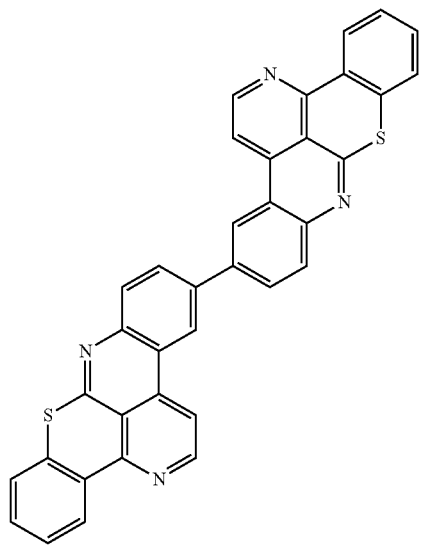 [SMILES: c1ccc2c(c1)Sc1nc3ccc(-c4ccc5nc6c7c(nccc7c5c4)-c4ccccc4S6)cc3c3ccnc-2c13]

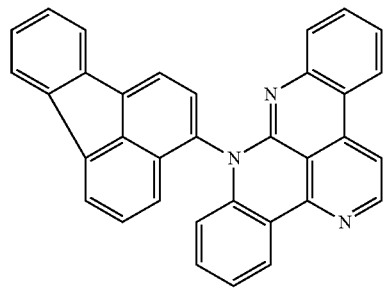 [SMILES: c1ccc2c(c1)-c1cccc3c(N4c5ccccc5-c5nccc6c5c4nc4ccccc46)ccc-2c13]
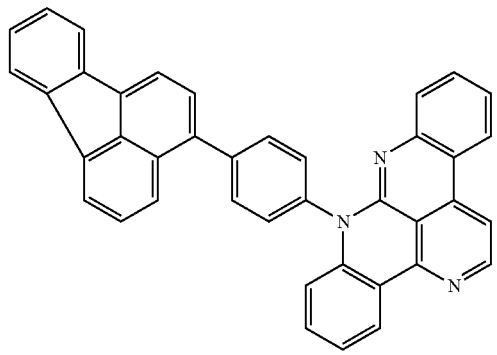 [SMILES: c1ccc2c(c1)-c1cccc3c(-c4ccc(N5c6ccccc6-c6nccc7c6c5nc5ccccc57)cc4)ccc-2c13]
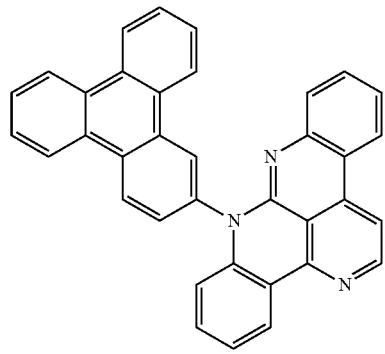 [SMILES: c1ccc2c(c1)-c1nccc3c1c(nc1ccccc13)N2c1ccc2c3ccccc3c3ccccc3c2c1]
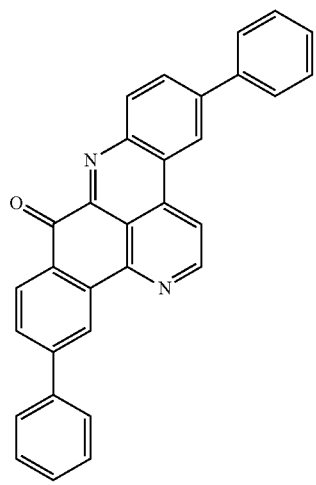 [SMILES: O=C1c2ccc(-c3ccccc3)cc2-c2nccc3c2c1nc1ccc(-c2ccccc2)cc13]

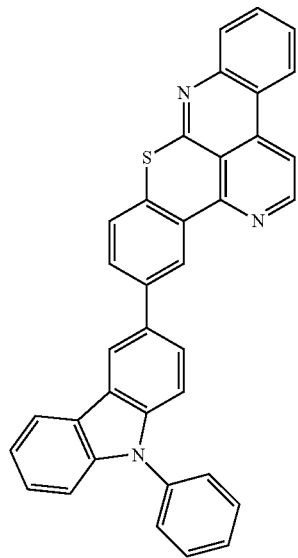 [SMILES: c1ccc(-n2c3ccccc3c3cc(-c4ccc5c(c4)-c4nccc6c4c(nc4ccccc46)S5)ccc32)cc1]
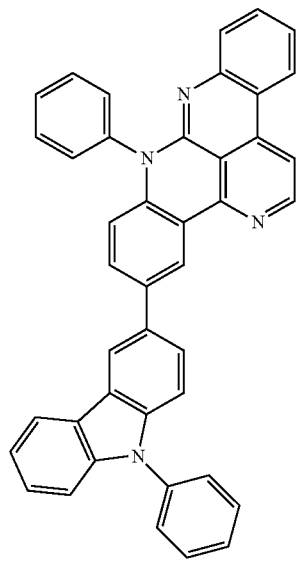 [SMILES: c1ccc(N2c3ccc(-c4ccc5c(c4)c4ccccc4n5-c4ccccc4)cc3-c3nccc4c3c2nc2ccccc24)cc1]
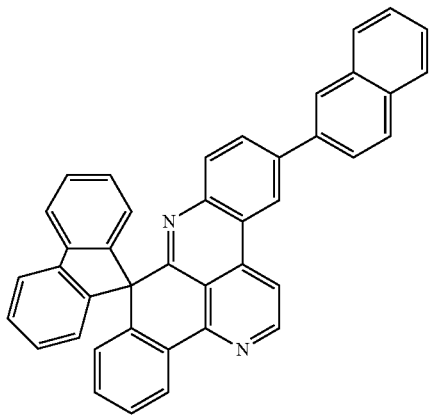 [SMILES: c1ccc2c(c1)-c1ccccc1C21c2ccccc2-c2nccc3c2c1nc1ccc(-c2ccc4ccccc4c2)cc13]

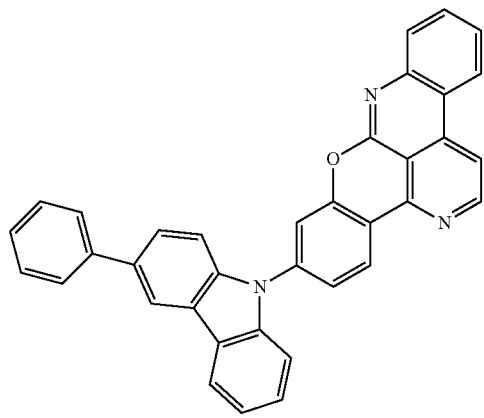 [SMILES: c1ccc(-c2ccc3c(c2)c2ccccc2n3-c2ccc3c(c2)Oc2nc4ccccc4c4ccnc-3c24)cc1]
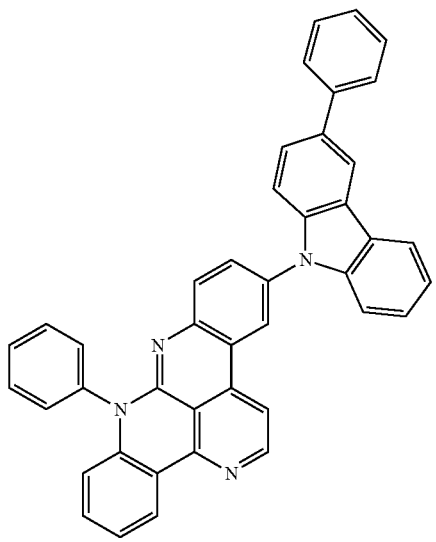 [SMILES: c1ccc(-c2ccc3c(c2)c2ccccc2n3-c2ccc3nc4c5c(nccc5c3c2)-c2ccccc2N4c2ccccc2)cc1]
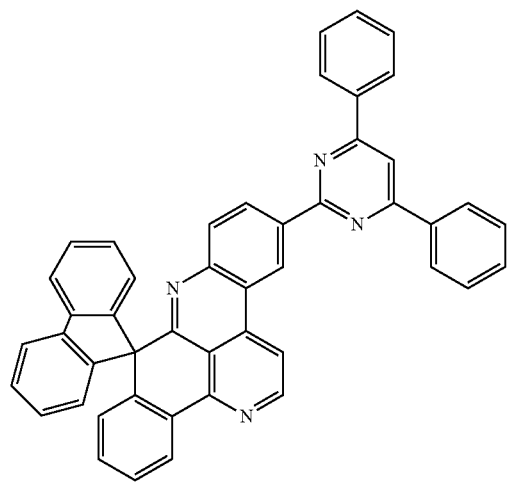 [SMILES: c1ccc(-c2cc(-c3ccccc3)nc(-c3ccc4nc5c6c(nccc6c4c3)-c3ccccc3C53c4ccccc4-c4ccccc43)n2)cc1]

-continued
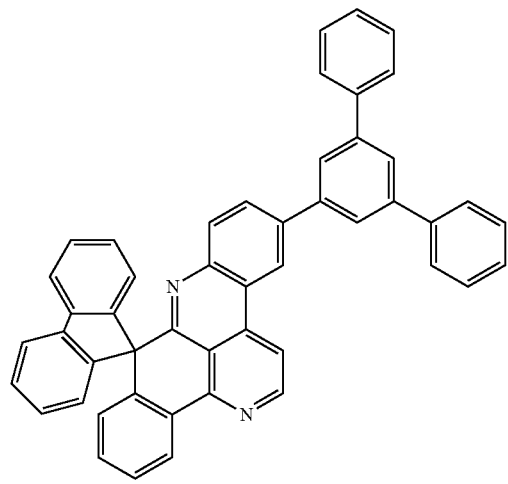 [SMILES: c1ccc(-c2cc(-c3ccccc3)cc(-c3ccc4nc5c6c(nccc6c4c3)-c3ccccc3C53c4ccccc4-c4ccccc43)c2)cc1]
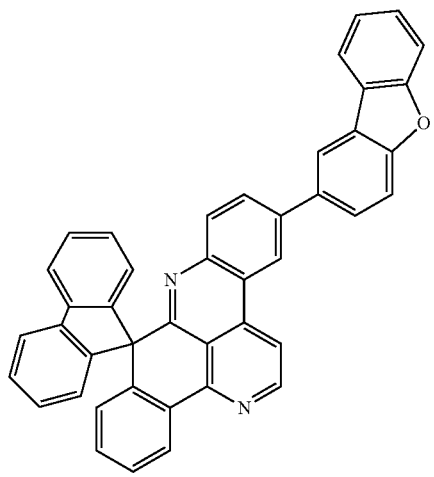 [SMILES: c1ccc2c(c1)-c1ccccc1C21c2ccccc2-c2nccc3c2c1nc1ccc(-c2ccc4oc5ccccc5c4c2)cc13]
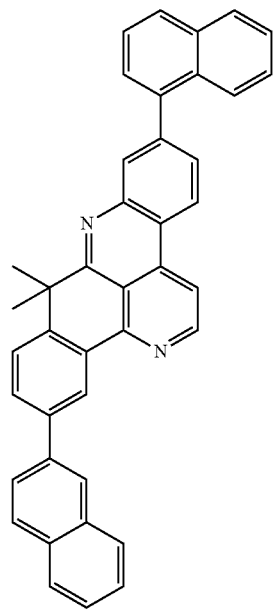 [SMILES: CC1(C)c2ccc(-c3ccc4ccccc4c3)cc2-c2nccc3c2c1nc1cc(-c2cccc4ccccc24)ccc13]

-continued
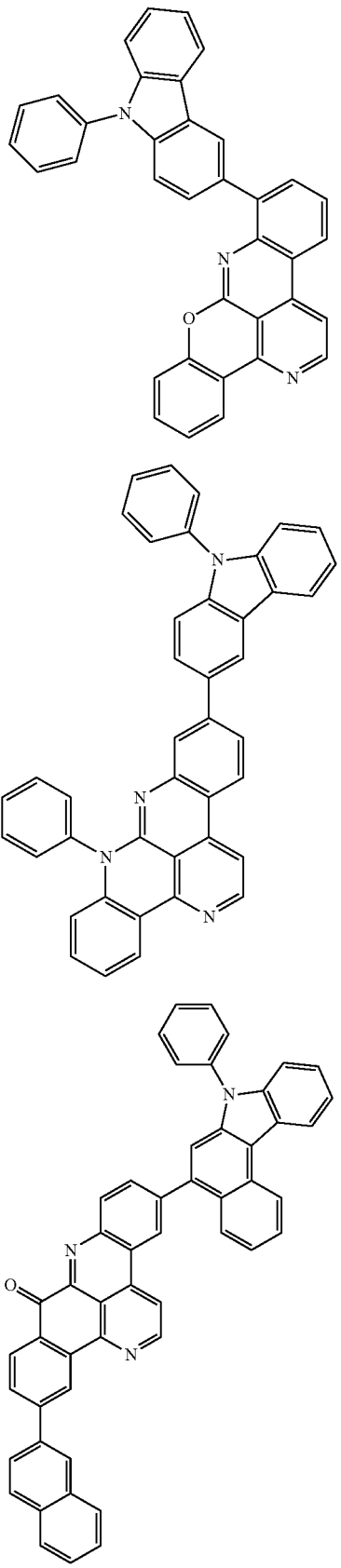

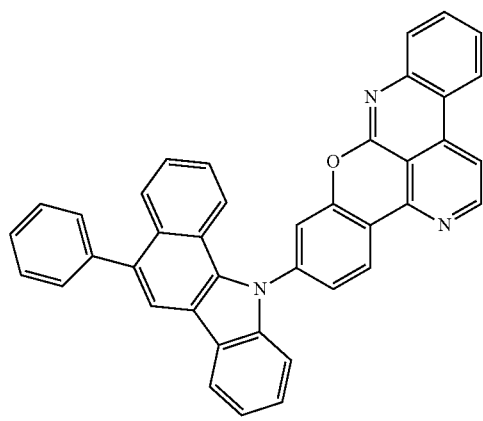 [SMILES: c1ccc(-c2cc3c4ccccc4n(-c4ccc5c(c4)Oc4nc6ccccc6c6ccnc-5c46)c3c3ccccc23)cc1]
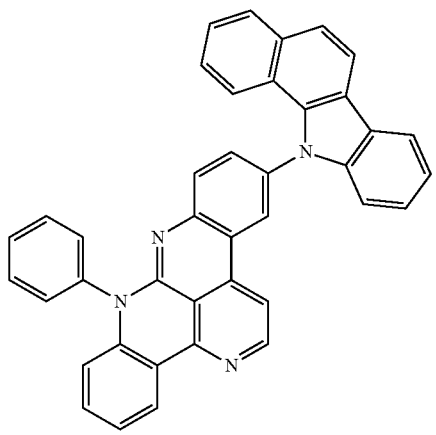 [SMILES: c1ccc(N2c3ccccc3-c3nccc4c3c2nc2ccc(-n3c5ccccc5c5ccc6ccccc6c53)cc24)cc1]
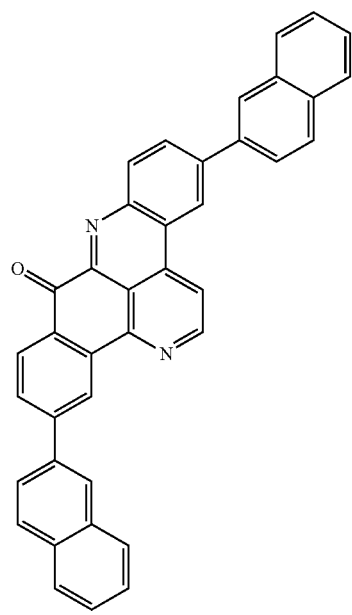 [SMILES: O=C1c2ccc(-c3ccc4ccccc4c3)cc2-c2nccc3c2c1nc1ccc(-c2ccc4ccccc4c2)cc13]

-continued
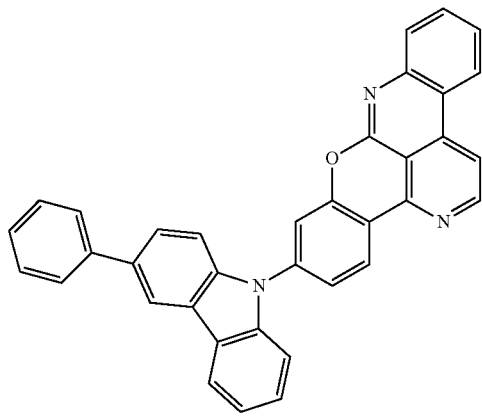 [SMILES: c1ccc(-c2ccc3c(c2)c2ccccc2n3-c2ccc3c(c2)Oc2nc4ccccc4c4ccnc-3c24)cc1]
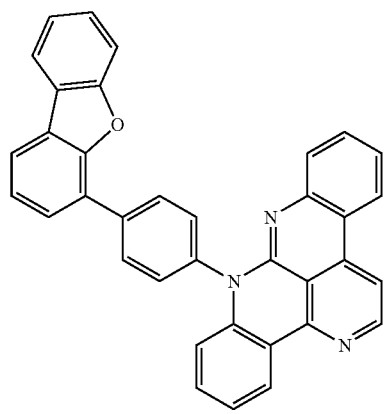 [SMILES: c1ccc2c(c1)-c1nccc3c1c(nc1ccccc13)N2c1ccc(-c2cccc3c2oc2ccccc23)cc1]
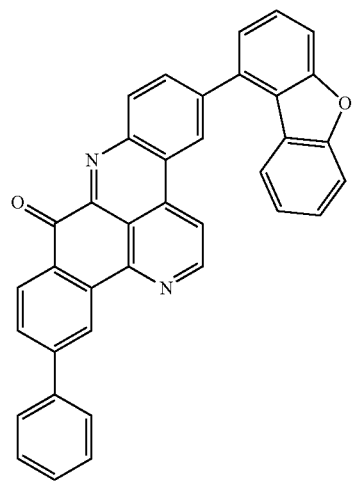 [SMILES: O=C1c2ccc(-c3ccccc3)cc2-c2nccc3c2c1nc1ccc(-c2cccc4oc5ccccc5c24)cc13]

-continued
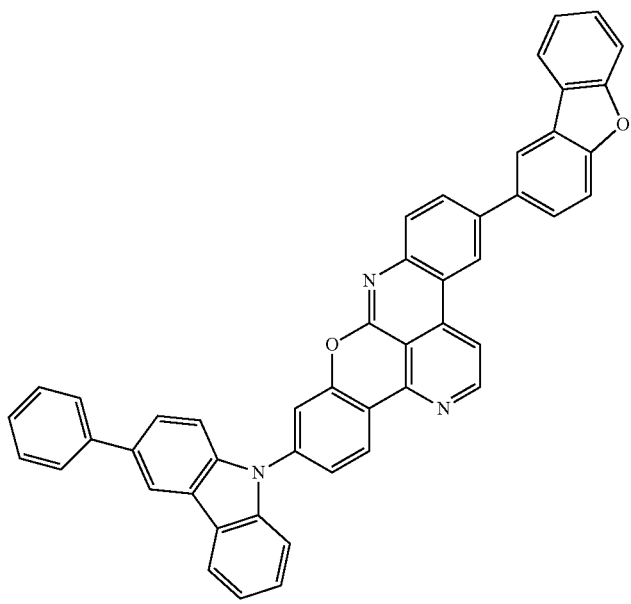 [SMILES: c1ccc(-c2ccc3c(c2)c2ccccc2n3-c2ccc3c(c2)Oc2nc4ccc(-c5ccc6oc7ccccc7c6c5)cc4c4ccnc-3c24)cc1]
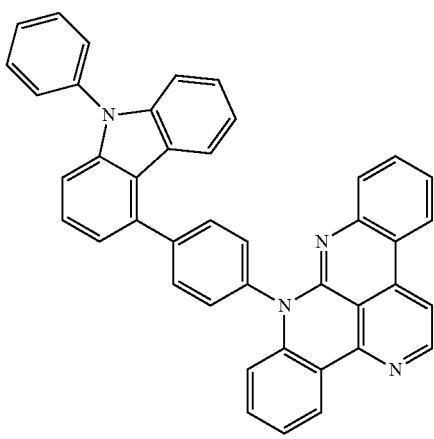 [SMILES: c1ccc(-n2c3ccccc3c3c(-c4ccc(N5c6ccccc6-c6nccc7c6c5nc5ccccc57)cc4)cccc32)cc1]
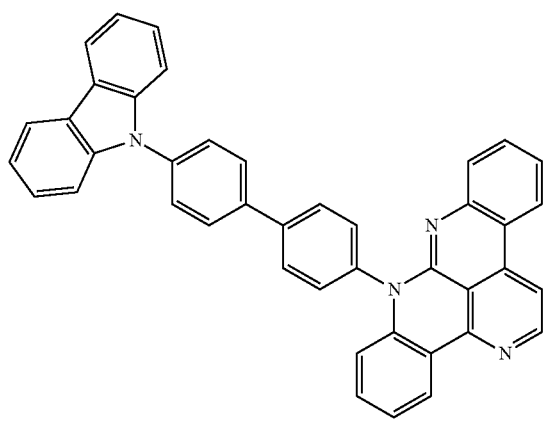 [SMILES: c1ccc2c(c1)-c1nccc3c1c(nc1ccccc13)N2c1ccc(-c2ccc(-n3c4ccccc4c4ccccc43)cc2)cc1]

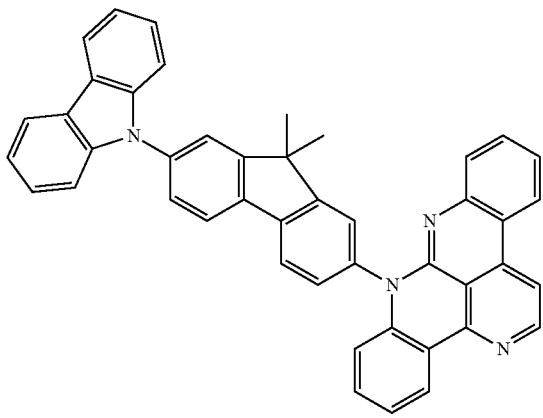 [SMILES: CC1(C)c2cc(N3c4ccccc4-c4nccc5c4c3nc3ccccc35)ccc2-c2ccc(-n3c4ccccc4c4ccccc43)cc21]
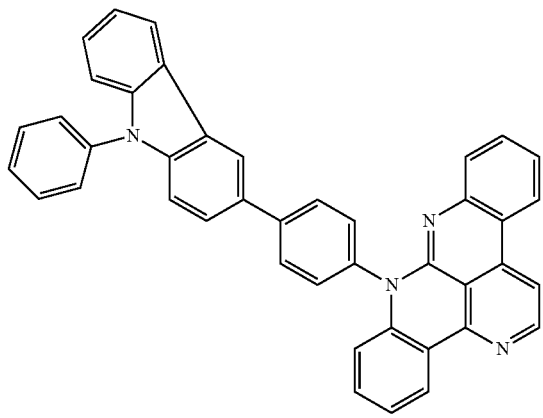 [SMILES: c1ccc(-n2c3ccccc3c3cc(-c4ccc(N5c6ccccc6-c6nccc7c6c5nc5ccccc57)cc4)ccc32)cc1]
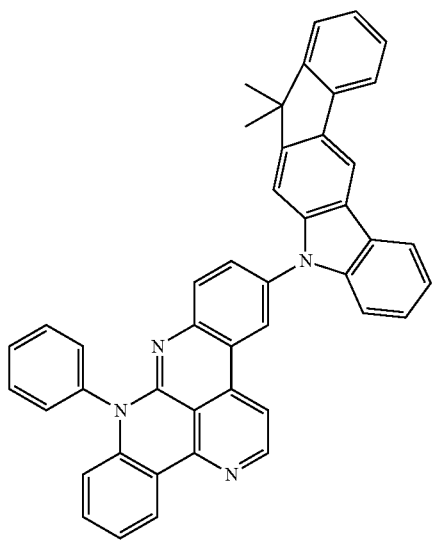 [SMILES: CC1(C)c2ccccc2-c2cc3c4ccccc4n(-c4ccc5nc6c7c(nccc7c5c4)-c4ccccc4N6c4ccccc4)c3cc21]

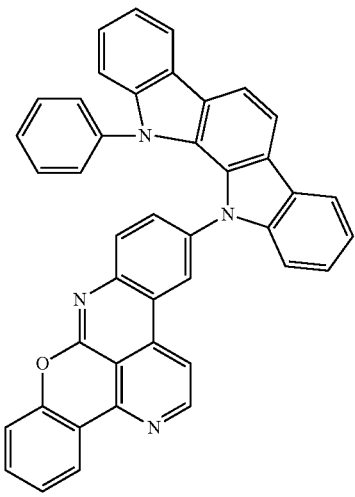 [SMILES: c1ccc(-n2c3ccccc3c3ccc4c5ccccc5n(-c5ccc6nc7c8c(nccc8c6c5)-c5ccccc5O7)c4c32)cc1]
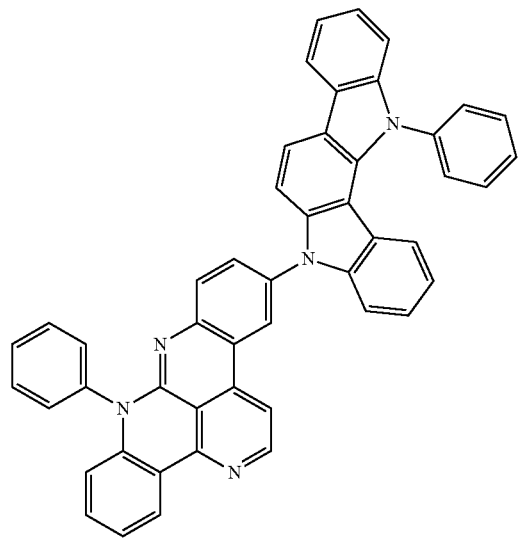 [SMILES: c1ccc(N2c3ccccc3-c3nccc4c3c2nc2ccc(-n3c5ccccc5c5c3ccc3c6ccccc6n(-c6ccccc6)c35)cc24)cc1]
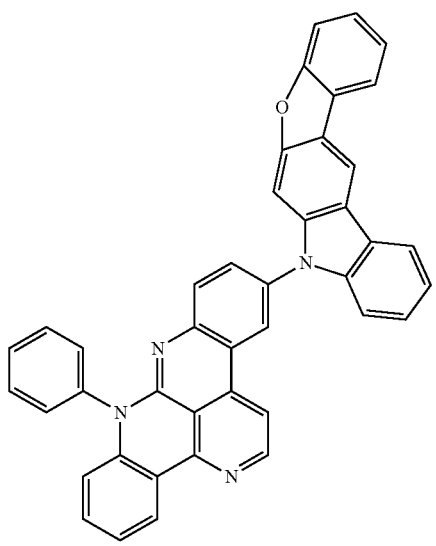 [SMILES: c1ccc(N2c3ccccc3-c3nccc4c3c2nc2ccc(-n3c5ccccc5c5cc6c(cc53)oc3ccccc36)cc24)cc1]

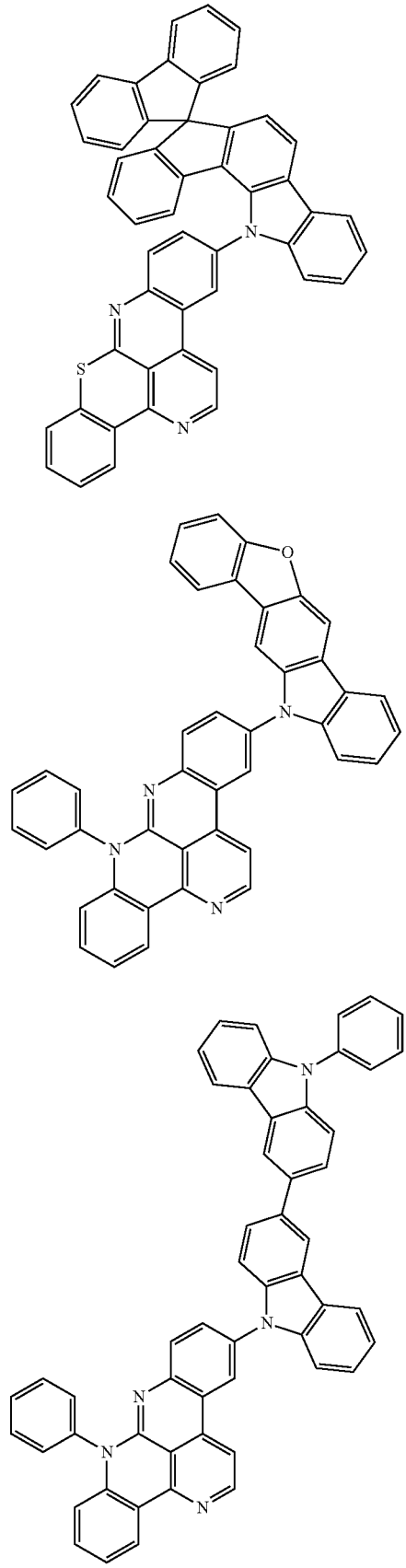

-continued
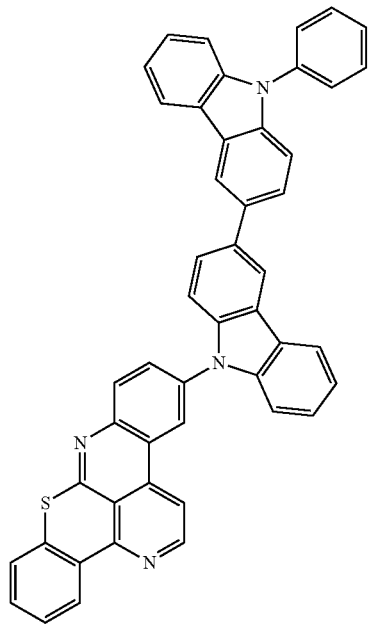 [SMILES: c1ccc(-n2c3ccccc3c3cc(-c4ccc5c(c4)c4ccccc4n5-c4ccc5nc6c7c(nccc7c5c4)-c4ccccc4S6)ccc32)cc1]
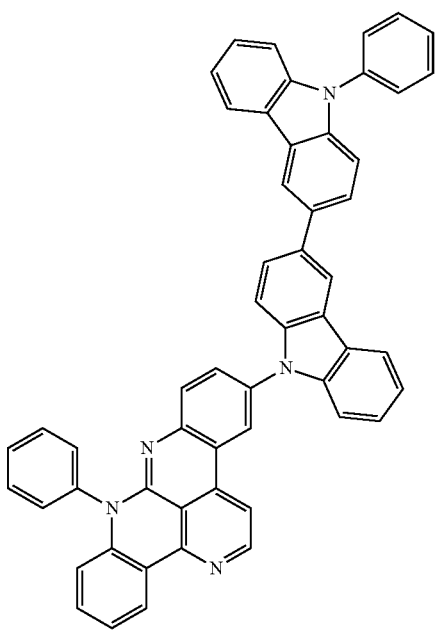 [SMILES: c1ccc(N2c3ccccc3-c3nccc4c3c2nc2ccc(-n3c5ccccc5c5cc(-c6ccc7c(c6)c6ccccc6n7-c6ccccc6)ccc53)cc24)cc1]

-continued
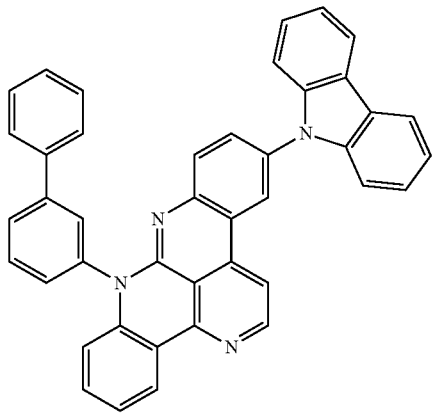 [SMILES: c1ccc(-c2cccc(N3c4ccccc4-c4nccc5c4c3nc3ccc(-n4c6ccccc6c6ccccc64)cc35)c2)cc1]
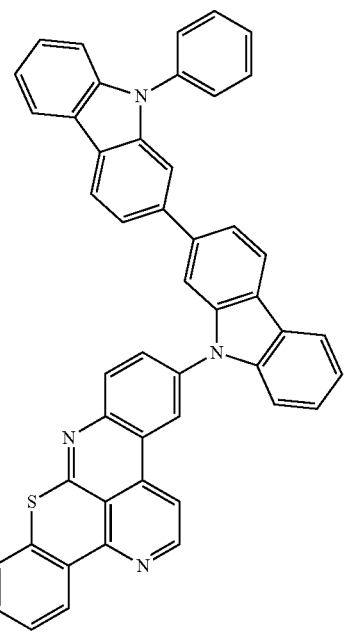
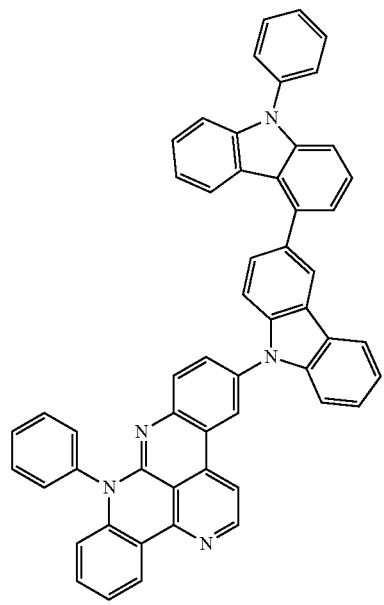 [SMILES: c1ccc(N2c3ccccc3-c3nccc4c3c2nc2ccc(-n3c5ccccc5c5cc(-c6cccc7c6c6ccccc6n7-c6ccccc6)ccc53)cc24)cc1]

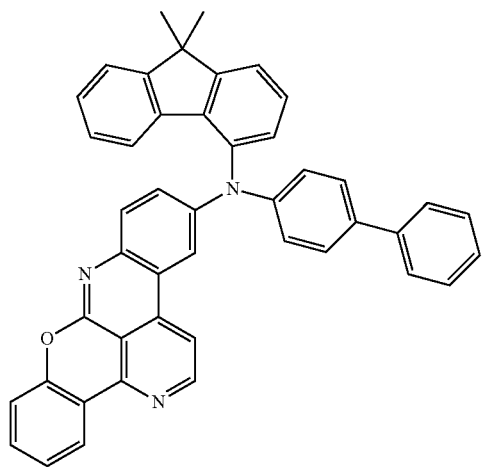 [SMILES: CC1(C)c2ccccc2-c2c(N(c3ccc(-c4ccccc4)cc3)c3ccc4nc5c6c(nccc6c4c3)-c3ccccc3O5)cccc21]
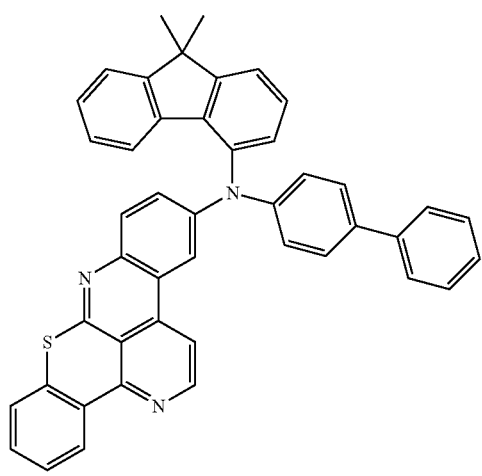 [SMILES: CC1(C)c2ccccc2-c2c(N(c3ccc(-c4ccccc4)cc3)c3ccc4nc5c6c(nccc6c4c3)-c3ccccc3S5)cccc21]
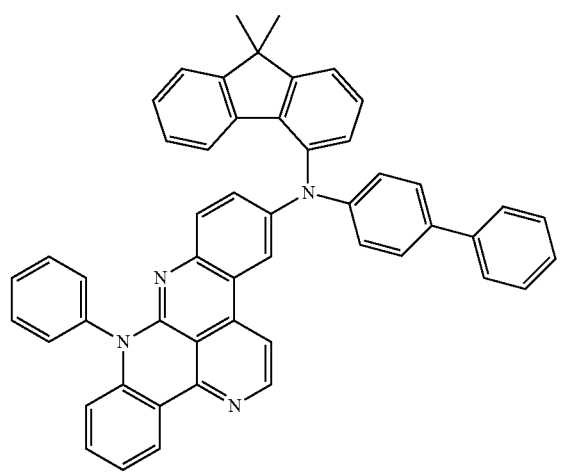 [SMILES: CC1(C)c2ccccc2-c2c(N(c3ccc(-c4ccccc4)cc3)c3ccc4nc5c6c(nccc6c4c3)-c3ccccc3N5c3ccccc3)cccc21]

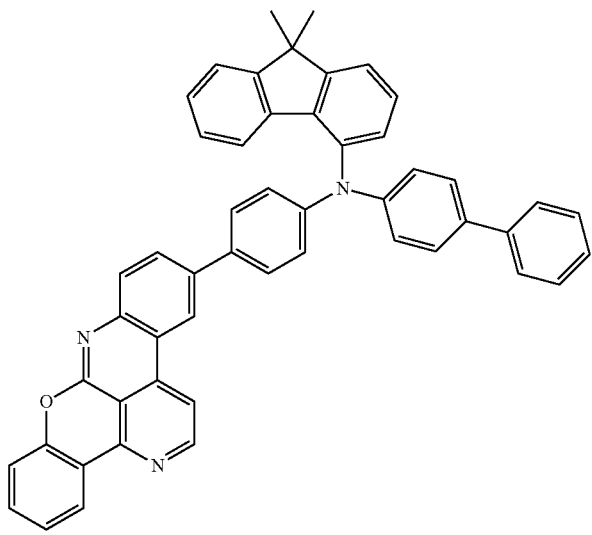 [SMILES: CC1(C)c2ccccc2-c2c(N(c3ccc(-c4ccccc4)cc3)c3ccc(-c4ccc5nc6c7c(nccc7c5c4)-c4ccccc4O6)cc3)cccc21]
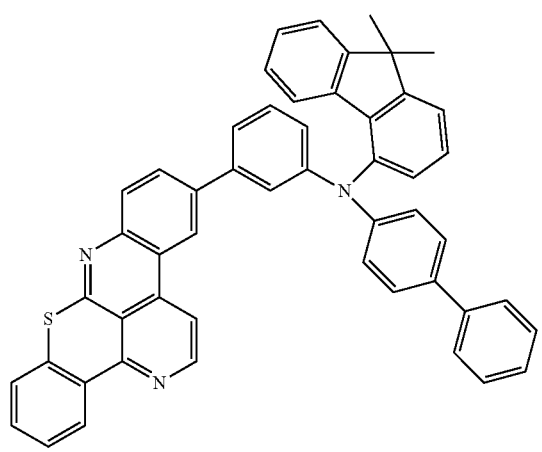 [SMILES: CC1(C)c2ccccc2-c2c(N(c3ccc(-c4ccccc4)cc3)c3cccc(-c4ccc5nc6c7c(nccc7c5c4)-c4ccccc4S6)c3)cccc21]
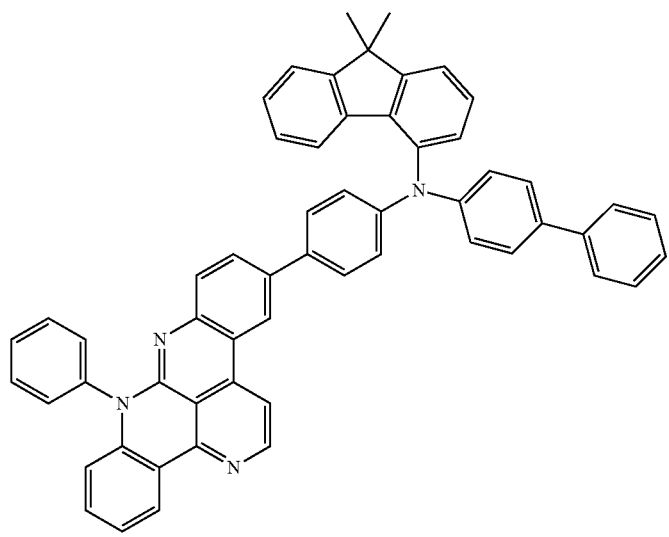 [SMILES: CC1(C)c2ccccc2-c2c(N(c3ccc(-c4ccccc4)cc3)c3ccc(-c4ccc5nc6c7c(nccc7c5c4)-c4ccccc4N6c4ccccc4)cc3)cccc21]

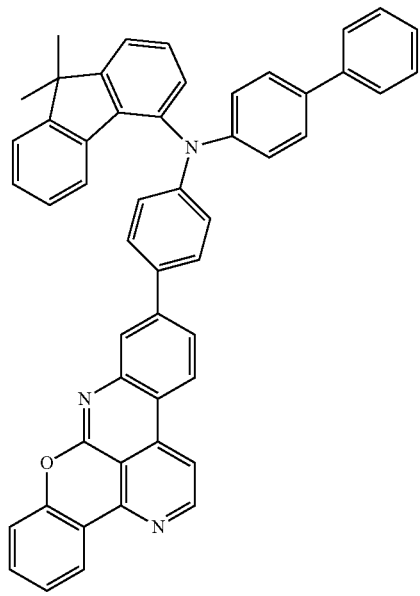 [SMILES: CC1(C)c2ccccc2-c2c(N(c3ccc(-c4ccccc4)cc3)c3ccc(-c4ccc5c(c4)nc4c6c(nccc65)-c5ccccc5O4)cc3)cccc21]
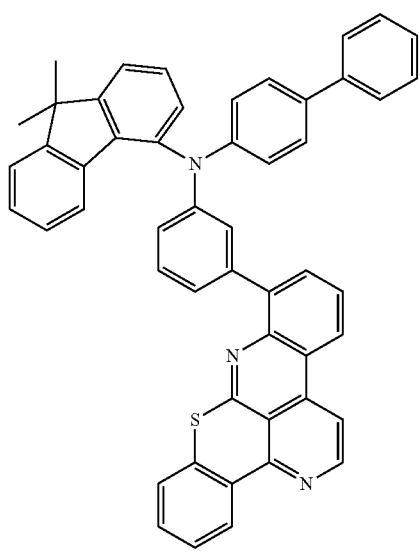 [SMILES: CC1(C)c2ccccc2-c2c(N(c3ccc(-c4ccccc4)cc3)c3cccc(-c4cccc5c4nc4c6c(nccc65)-c5ccccc5S4)c3)cccc21]

-continued
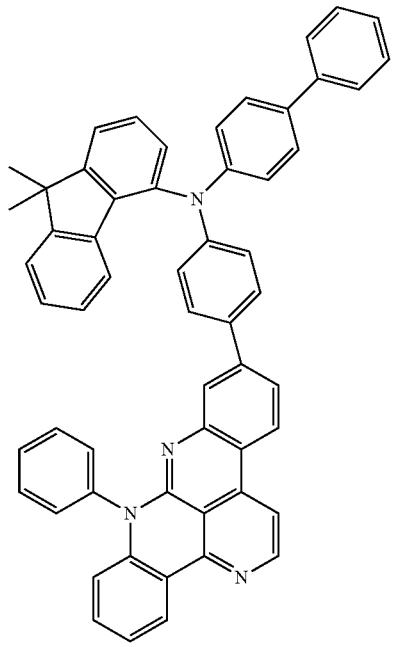 [SMILES: CC1(C)c2ccccc2-c2c(N(c3ccc(-c4ccccc4)cc3)c3ccc(-c4ccc5c(c4)nc4c6c(nccc65)-c5ccccc5N4c4ccccc4)cc3)cccc21]
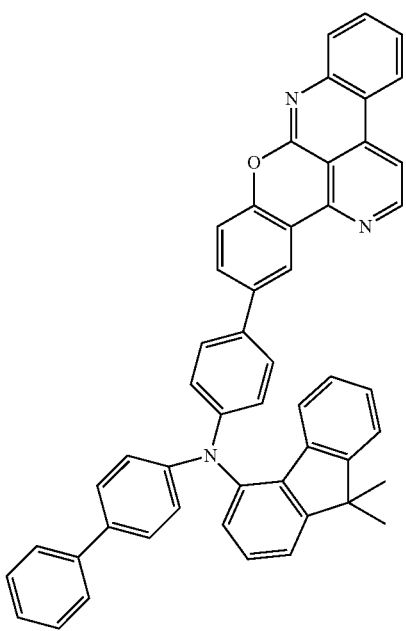 [SMILES: CC1(C)c2ccccc2-c2c(N(c3ccc(-c4ccccc4)cc3)c3ccc(-c4ccc5c(c4)-c4nccc6c4c(nc4ccccc46)O5)cc3)cccc21]

-continued
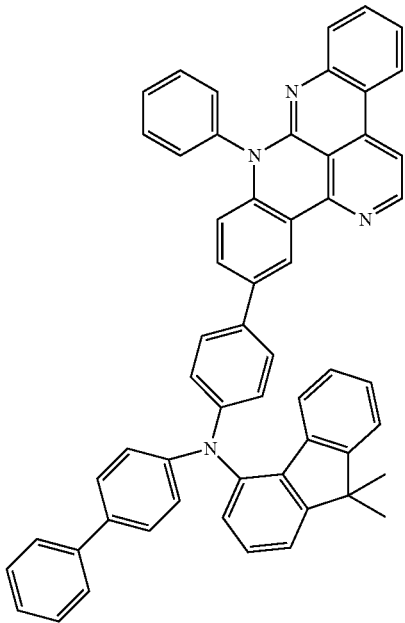 [SMILES: CC1(C)c2ccccc2-c2c(N(c3ccc(-c4ccccc4)cc3)c3ccc(-c4ccc5c(c4)-c4nccc6c4c(nc4ccccc46)N5c4ccccc4)cc3)cccc21]
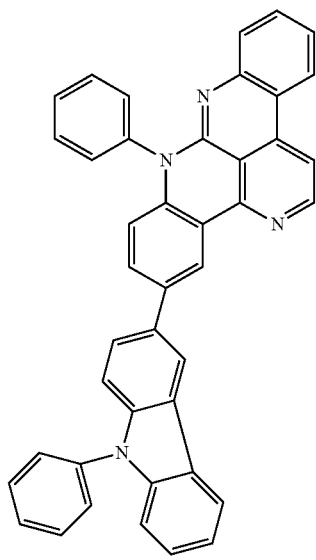 [SMILES: c1ccc(N2c3ccc(-c4ccc5c(c4)c4ccccc4n5-c4ccccc4)cc3-c3nccc4c3c2nc2ccccc24)cc1]

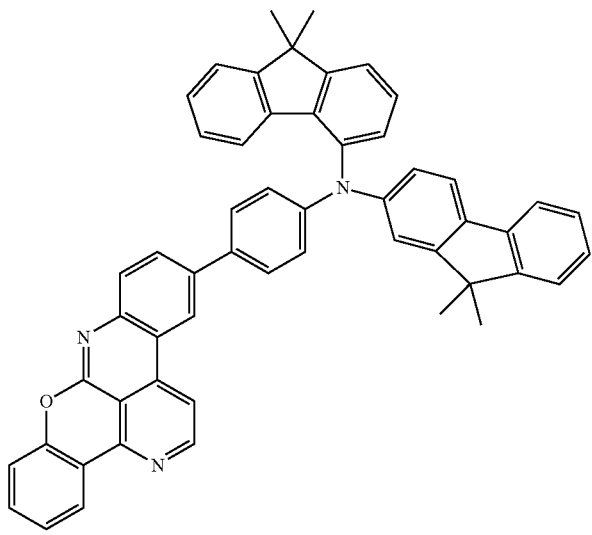 [SMILES: CC1(C)c2ccccc2-c2ccc(N(c3ccc(-c4ccc5nc6c7c(nccc7c5c4)-c4ccccc4O6)cc3)c3cccc4c3-c3ccccc3C4(C)C)cc21]
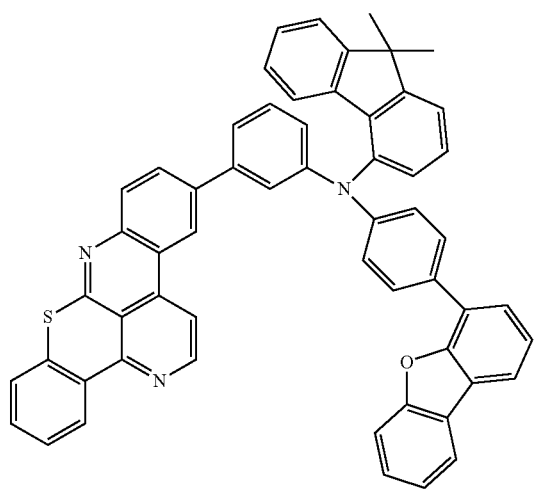 [SMILES: CC1(C)c2ccccc2-c2c(N(c3ccc(-c4cccc5c4oc4ccccc45)cc3)c3cccc(-c4ccc5nc6c7c(nccc7c5c4)-c4ccccc4S6)c3)cccc21]
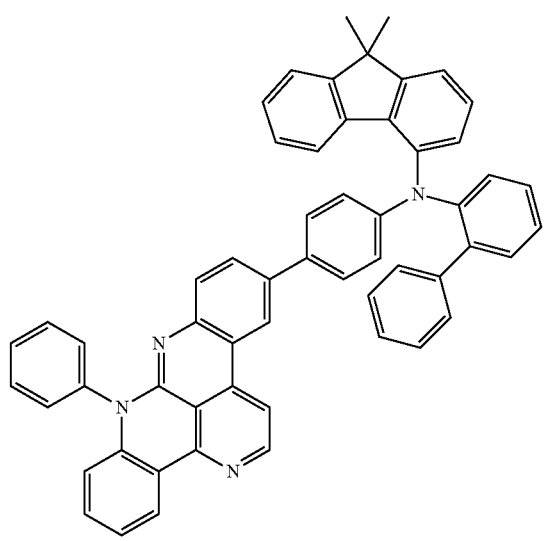 [SMILES: CC1(C)c2ccccc2-c2c(N(c3ccc(-c4ccc5nc6c7c(nccc7c5c4)-c4ccccc4N6c4ccccc4)cc3)c3ccccc3-c3ccccc3)cccc21]

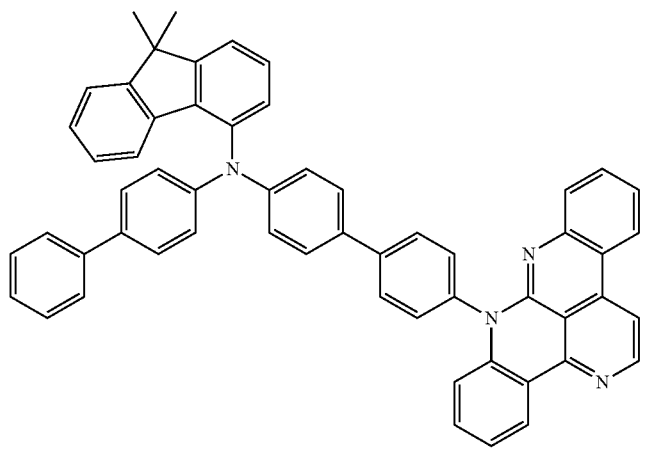 [SMILES: CC1(C)c2ccccc2-c2c(N(c3ccc(-c4ccccc4)cc3)c3ccc(-c4ccc(N5c6ccccc6-c6nccc7c6c5nc5ccccc57)cc4)cc3)cccc21]
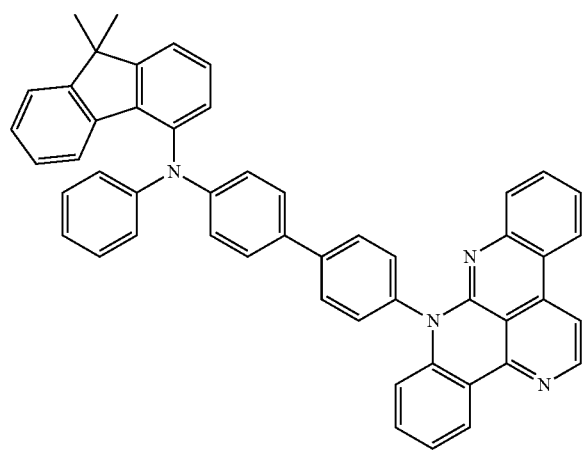 [SMILES: CC1(C)c2ccccc2-c2c(N(c3ccccc3)c3ccc(-c4ccc(N5c6ccccc6-c6nccc7c6c5nc5ccccc57)cc4)cc3)cccc21]
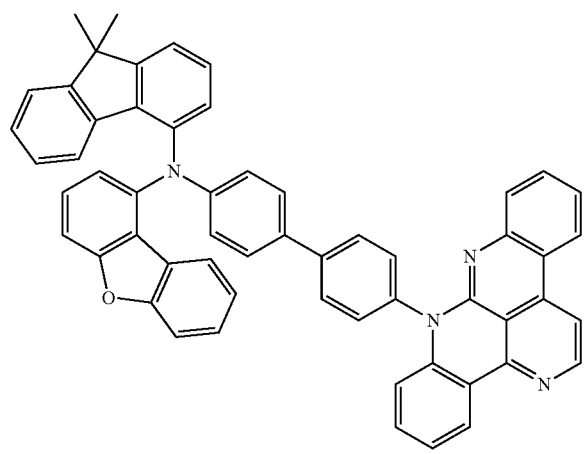 [SMILES: CC1(C)c2ccccc2-c2c(N(c3ccc(-c4ccc(N5c6ccccc6-c6nccc7c6c5nc5ccccc57)cc4)cc3)c3cccc4oc5ccccc5c34)cccc21]

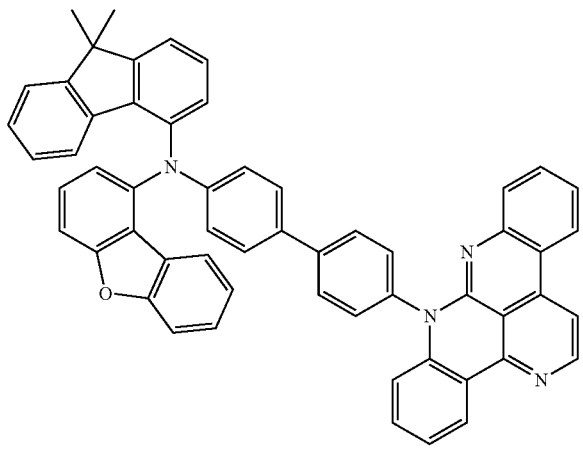 [SMILES: CC1(C)c2ccccc2-c2c(N(c3ccc(-c4ccc(N5c6ccccc6-c6nccc7c6c5nc5ccccc57)cc4)cc3)c3cccc4oc5ccccc5c34)cccc21]
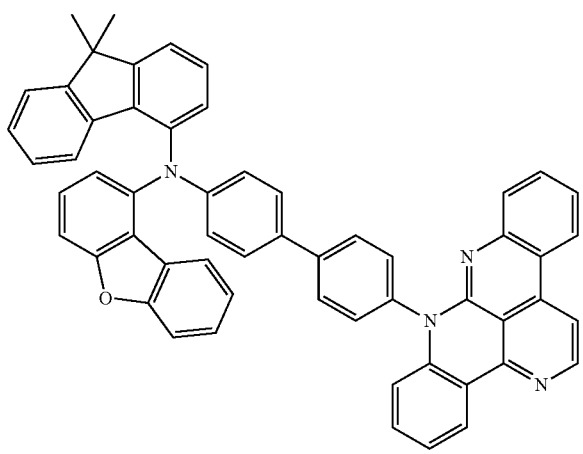 [SMILES: CC1(C)c2ccccc2-c2c(N(c3ccc(-c4ccc(N5c6ccccc6-c6nccc7c6c5nc5ccccc57)cc4)cc3)c3cccc4oc5ccccc5c34)cccc21]
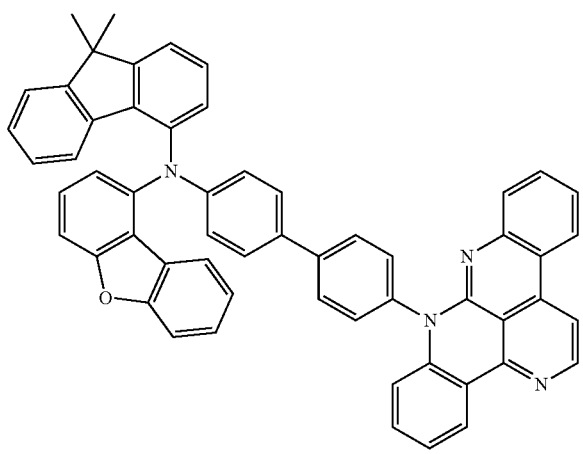 [SMILES: CC1(C)c2ccccc2-c2c(N(c3ccc(-c4ccc(N5c6ccccc6-c6nccc7c6c5nc5ccccc57)cc4)cc3)c3cccc4oc5ccccc5c34)cccc21]

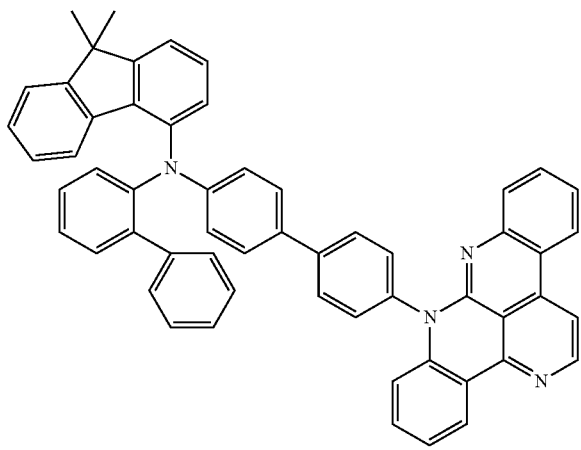 [SMILES: CC1(C)c2ccccc2-c2c(N(c3ccc(-c4ccc(N5c6ccccc6-c6nccc7c6c5nc5ccccc57)cc4)cc3)c3ccccc3-c3ccccc3)cccc21]
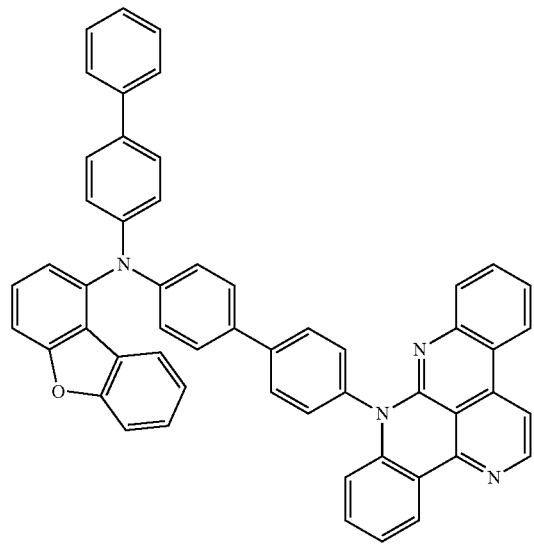 [SMILES: c1ccc(-c2ccc(N(c3ccc(-c4ccc(N5c6ccccc6-c6nccc7c6c5nc5ccccc57)cc4)cc3)c3cccc4oc5ccccc5c34)cc2)cc1]
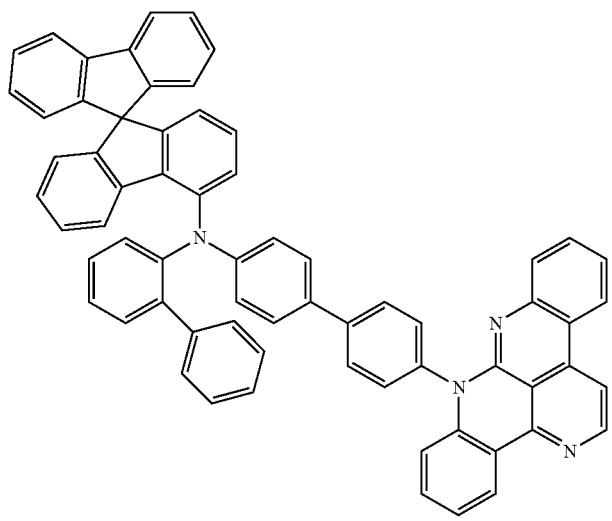 [SMILES: c1ccc(-c2ccccc2N(c2ccc(-c3ccc(N4c5ccccc5-c5nccc6c5c4nc4ccccc46)cc3)cc2)c2cccc3c2-c2ccccc2C32c3ccccc3-c3ccccc32)cc1]

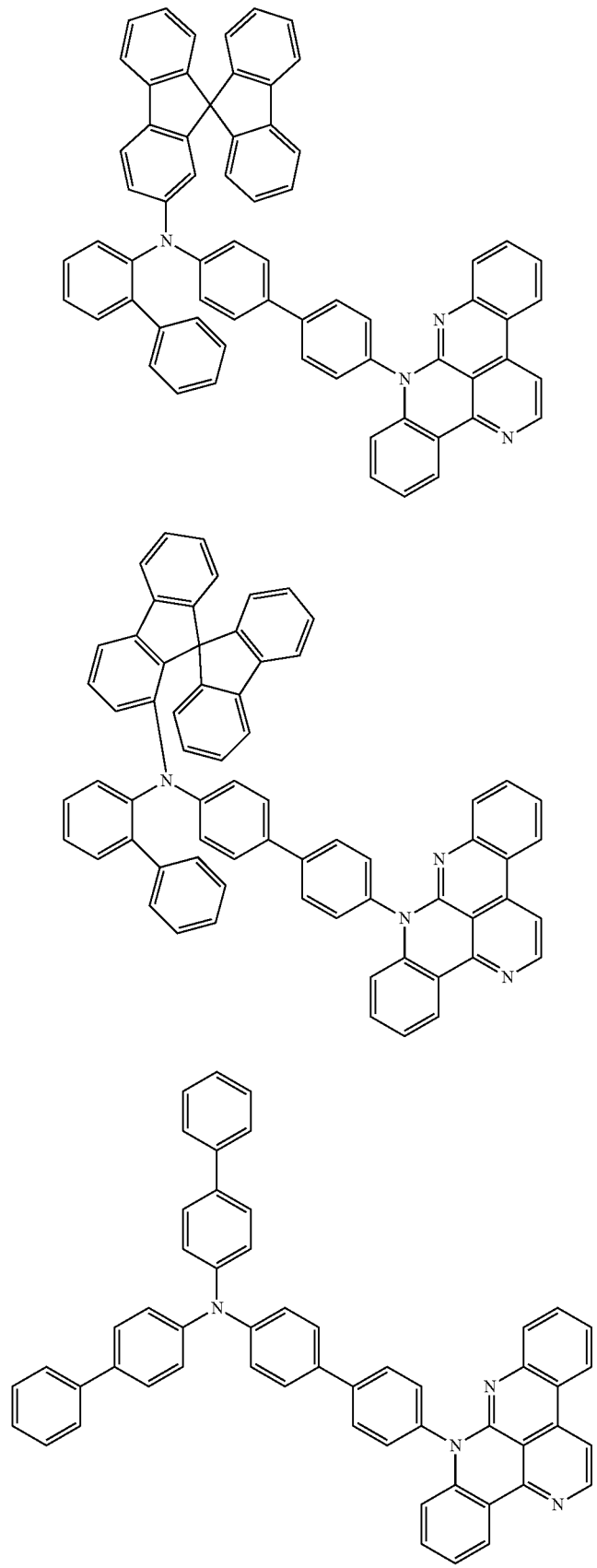

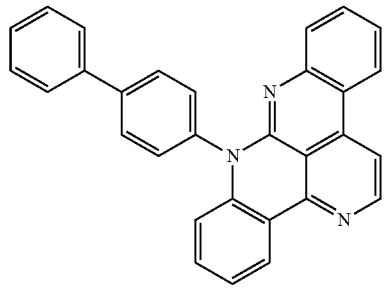 [SMILES: c1ccc(-c2ccc(N3c4ccccc4-c4nccc5c4c3nc3ccccc35)cc2)cc1]
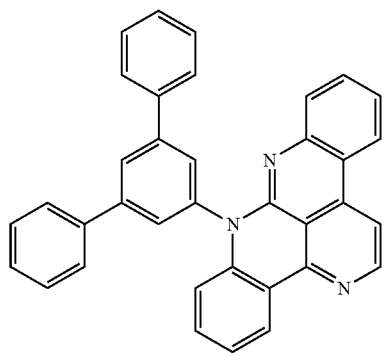 [SMILES: c1ccc(-c2cc(-c3ccccc3)cc(N3c4ccccc4-c4nccc5c4c3nc3ccccc35)c2)cc1]
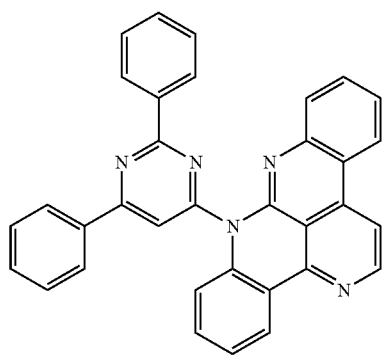 [SMILES: c1ccc(-c2cc(N3c4ccccc4-c4nccc5c4c3nc3ccccc35)nc(-c3ccccc3)n2)cc1]
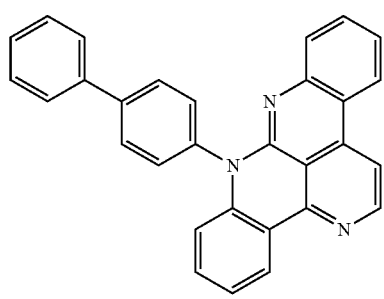 [SMILES: c1ccc(-c2ccc(N3c4ccccc4-c4nccc5c4c3nc3ccccc35)cc2)cc1]

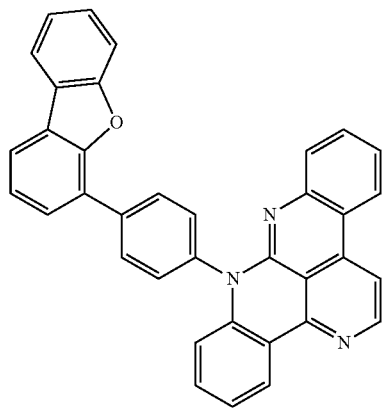 [SMILES: c1ccc2c(c1)-c1nccc3c1c(nc1ccccc13)N2c1ccc(-c2cccc3c2oc2ccccc23)cc1]
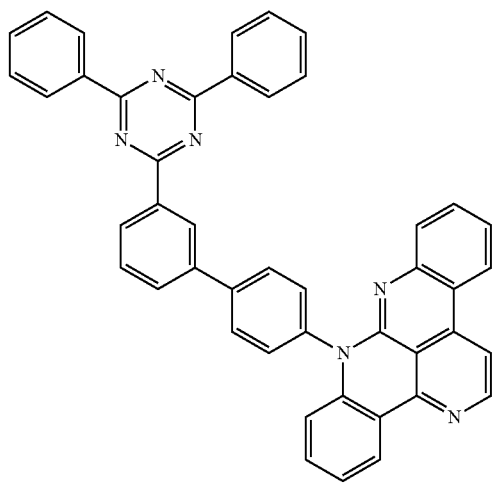 [SMILES: c1ccc(-c2nc(-c3ccccc3)nc(-c3cccc(-c4ccc(N5c6ccccc6-c6nccc7c6c5nc5ccccc57)cc4)c3)n2)cc1]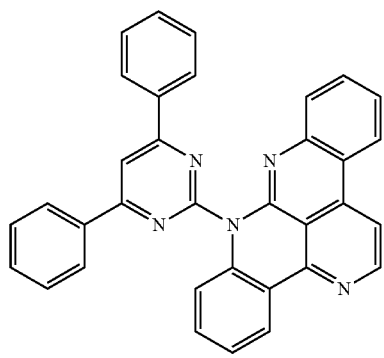 [SMILES: c1ccc(-c2cc(-c3ccccc3)nc(N3c4ccccc4-c4nccc5c4c3nc3ccccc35)n2)cc1]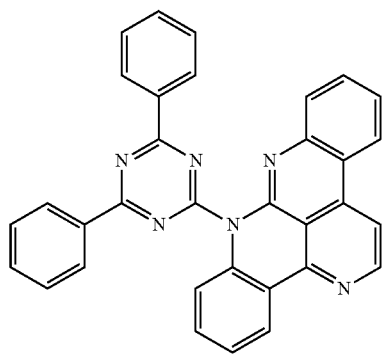

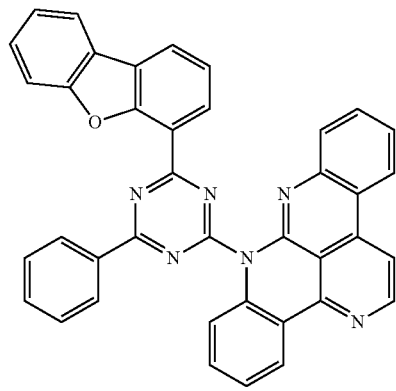 [SMILES: c1ccc(-c2nc(-c3cccc4c3oc3ccccc34)nc(N3c4ccccc4-c4nccc5c4c3nc3ccccc35)n2)cc1]
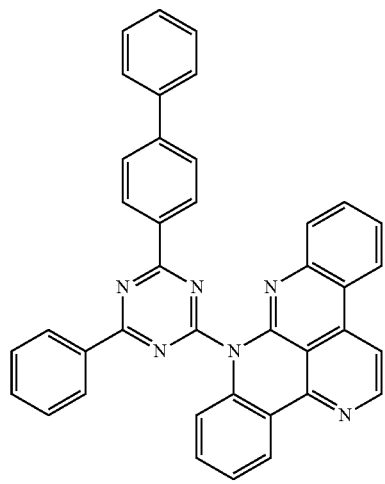 [SMILES: c1ccc(-c2ccc(-c3nc(-c4ccccc4)nc(N4c5ccccc5-c5nccc6c5c4nc4ccccc46)n3)cc2)cc1]
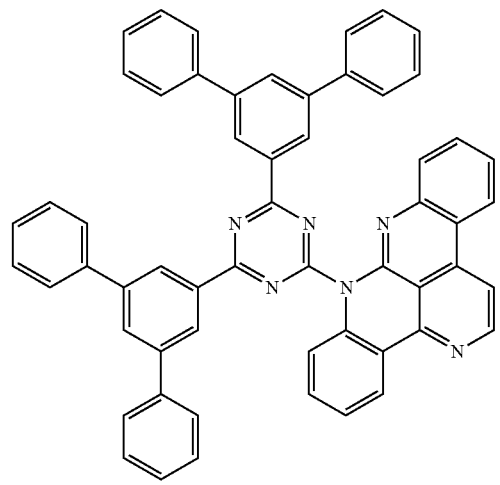 [SMILES: c1ccc(-c2cc(-c3ccccc3)cc(-c3nc(-c4cc(-c5ccccc5)cc(-c5ccccc5)c4)nc(N4c5ccccc5-c5nccc6c5c4nc4ccccc46)n3)c2)cc1]

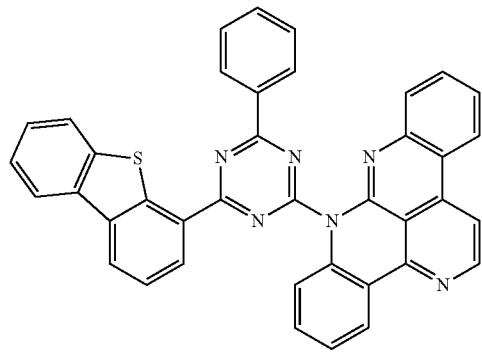 [SMILES: c1ccc(-c2nc(-c3cccc4c3sc3ccccc34)nc(N3c4ccccc4-c4nccc5c4c3nc3ccccc35)n2)cc1]
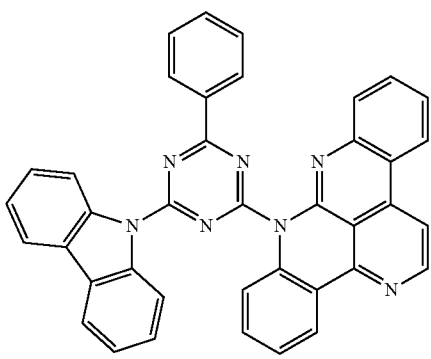 [SMILES: c1ccc(-c2nc(N3c4ccccc4-c4nccc5c4c3nc3ccccc35)nc(-n3c4ccccc4c4ccccc43)n2)cc1]
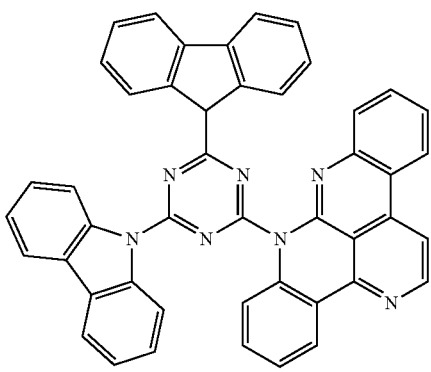 [SMILES: c1ccc2c(c1)-c1ccccc1C2c1nc(N2c3ccccc3-c3nccc4c3c2nc2ccccc24)nc(-n2c3ccccc3c3ccccc32)n1]
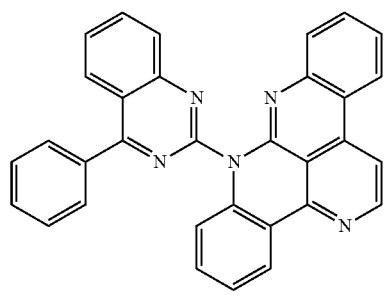 [SMILES: c1ccc(-c2nc(N3c4ccccc4-c4nccc5c4c3nc3ccccc35)nc3ccccc23)cc1]

-continued
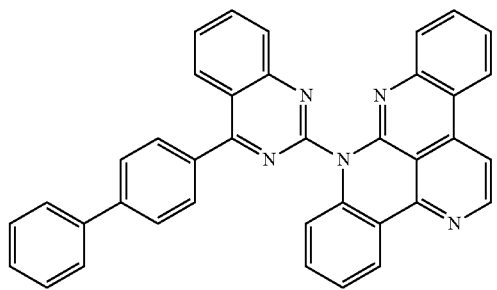 [SMILES: c1ccc(-c2ccc(-c3nc(N4c5ccccc5-c5nccc6c5c4nc4ccccc46)nc4ccccc34)cc2)cc1]
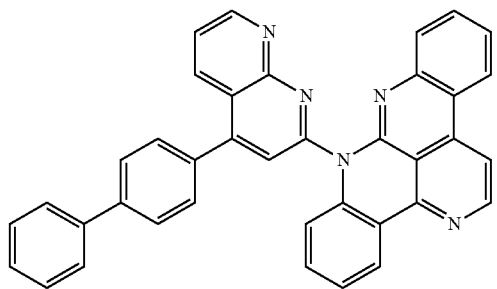 [SMILES: c1ccc(-c2ccc(-c3cc(N4c5ccccc5-c5nccc6c5c4nc4ccccc46)nc4ncccc34)cc2)cc1]
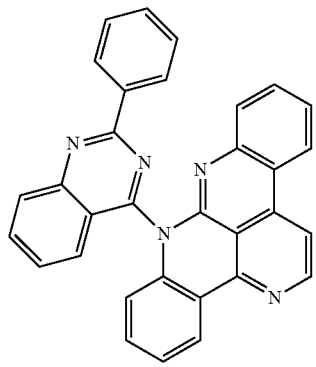 [SMILES: c1ccc(-c2nc(N3c4ccccc4-c4nccc5c4c3nc3ccccc35)c3ccccc3n2)cc1]
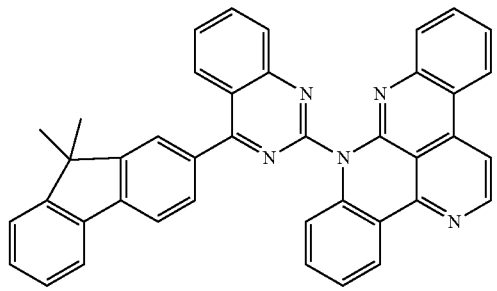 [SMILES: CC1(C)c2ccccc2-c2ccc(-c3nc(N4c5ccccc5-c5nccc6c5c4nc4ccccc46)nc4ccccc34)cc21]
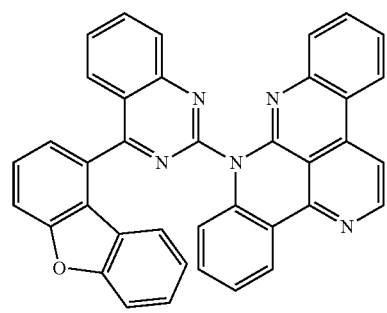 [SMILES: c1ccc2c(c1)-c1nccc3c1c(nc1ccccc13)N2c1nc(-c2cccc3oc4ccccc4c23)c2ccccc2n1]

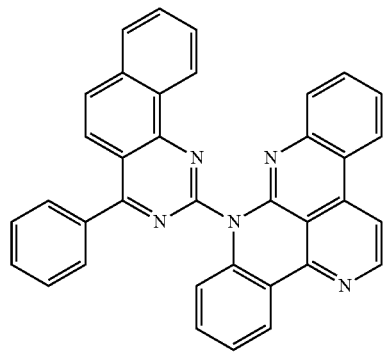 [SMILES: c1ccc(-c2nc(N3c4ccccc4-c4nccc5c4c3nc3ccccc35)nc3c2ccc2ccccc23)cc1]
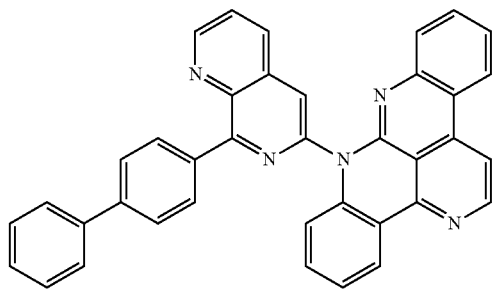 [SMILES: c1ccc(-c2ccc(-c3nc(N4c5ccccc5-c5nccc6c5c4nc4ccccc46)cc4cccnc34)cc2)cc1]
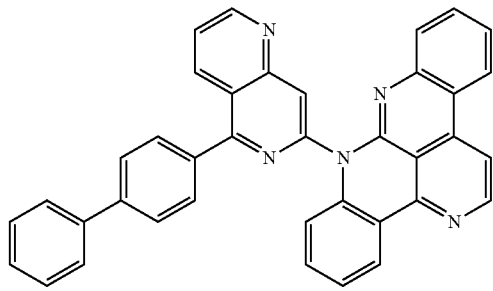 [SMILES: c1ccc(-c2ccc(-c3nc(N4c5ccccc5-c5nccc6c5c4nc4ccccc46)cc4ncccc34)cc2)cc1]
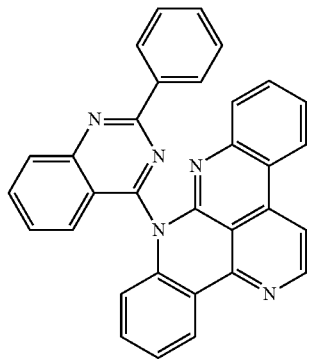 [SMILES: c1ccc(-c2nc(N3c4ccccc4-c4nccc5c4c3nc3ccccc35)c3ccccc3n2)cc1]
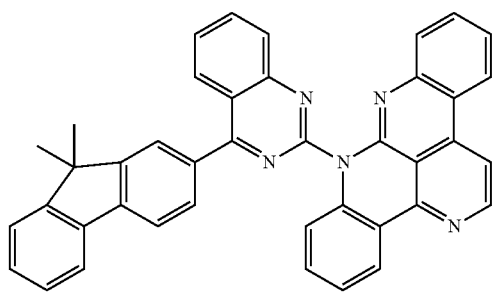 [SMILES: CC1(C)c2ccccc2-c2ccc(-c3nc(N4c5ccccc5-c5nccc6c5c4nc4ccccc46)nc4ccccc34)cc21]

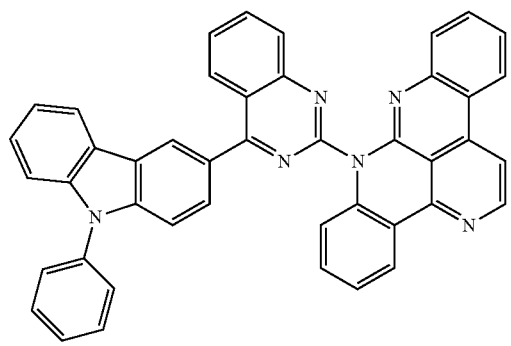 [SMILES: c1ccc(-n2c3ccccc3c3cc(-c4nc(N5c6ccccc6-c6nccc7c6c5nc5ccccc57)nc5ccccc45)ccc32)cc1]
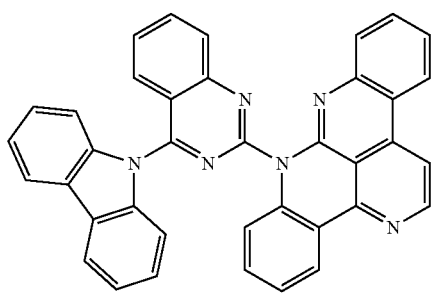 [SMILES: c1ccc2c(c1)-c1nccc3c1c(nc1ccccc13)N2c1nc(-n2c3ccccc3c3ccccc32)c2ccccc2n1]
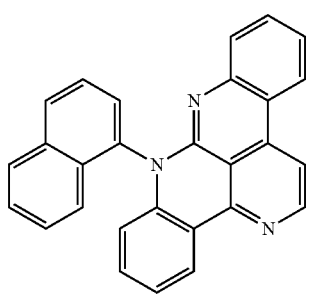 [SMILES: c1ccc2c(c1)-c1nccc3c1c(nc1ccccc13)N2c1cccc2ccccc12]
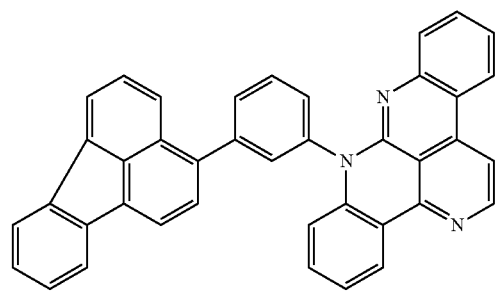 [SMILES: c1cc(-c2ccc3c4c(cccc24)-c2ccccc2-3)cc(N2c3ccccc3-c3nccc4c3c2nc2ccccc24)c1]

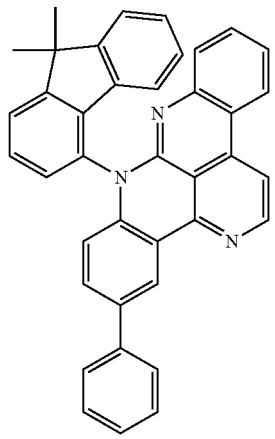 [SMILES: CC1(C)c2ccccc2-c2c(N3c4ccc(-c5ccccc5)cc4-c4nccc5c4c3nc3ccccc35)cccc21]
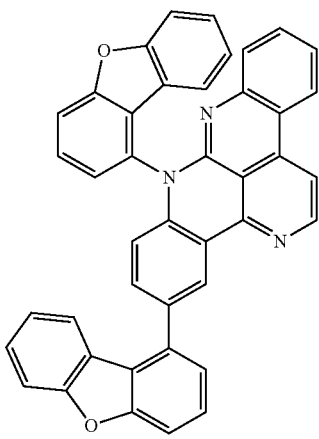 [SMILES: c1ccc2c(c1)nc1c3c(nccc32)-c2cc(-c3cccc4oc5ccccc5c34)ccc2N1c1cccc2oc3ccccc3c12]
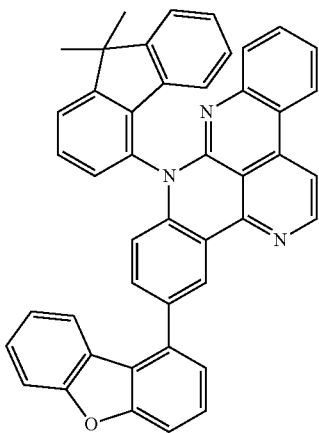 [SMILES: CC1(C)c2ccccc2-c2c(N3c4ccc(-c5cccc6oc7ccccc7c56)cc4-c4nccc5c4c3nc3ccccc35)cccc21]

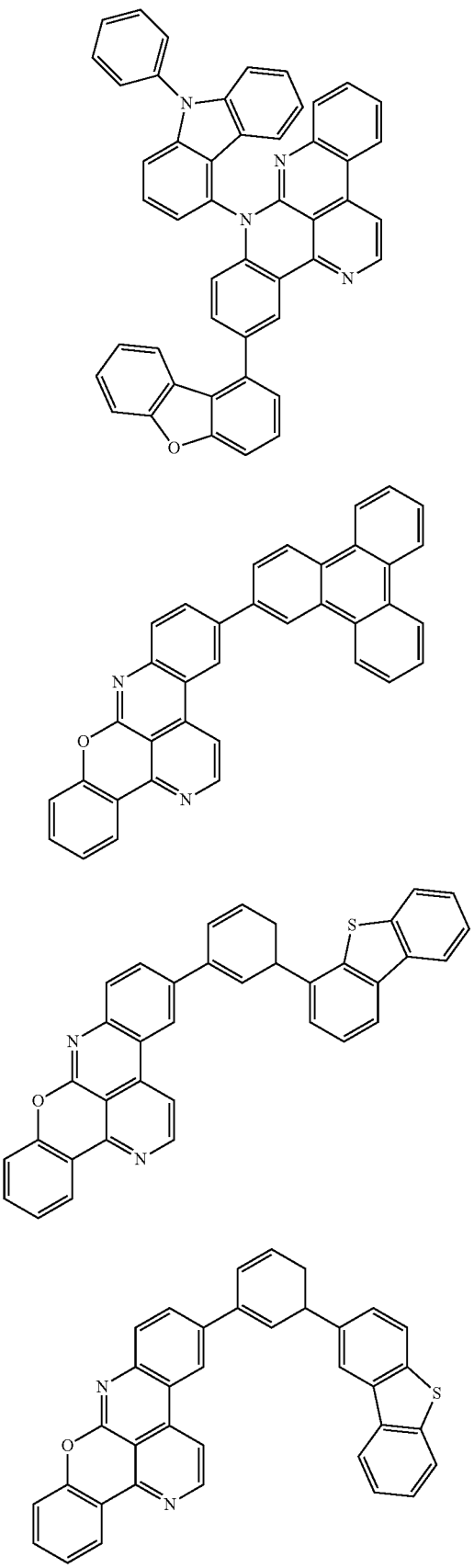

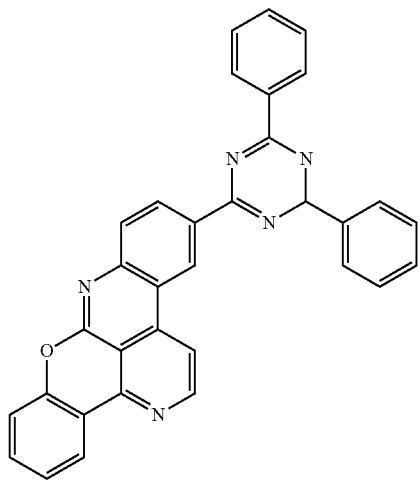 [SMILES: c1ccc(C2=NC(c3ccc4nc5c6c(nccc6c4c3)-c3ccccc3O5)=NC(c3ccccc3)N2)cc1]
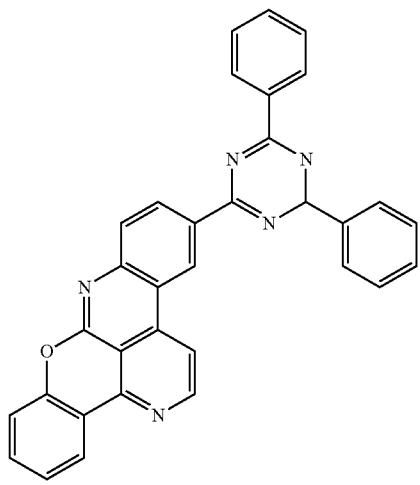 [SMILES: c1ccc(C2=NC(c3ccc4nc5c6c(nccc6c4c3)-c3ccccc3O5)=NC(c3ccccc3)N2)cc1]
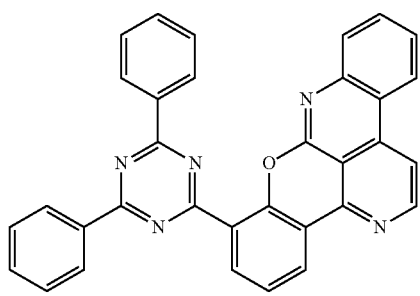 [SMILES: c1ccc(-c2nc(-c3ccccc3)nc(-c3cccc4c3Oc3nc5ccccc5c5ccnc-4c35)n2)cc1]

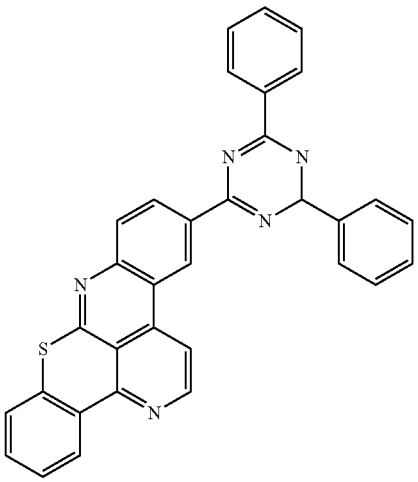 [SMILES: c1ccc(C2=NC(c3ccc4nc5c6c(nccc6c4c3)-c3ccccc3S5)=NC(c3ccccc3)N2)cc1]

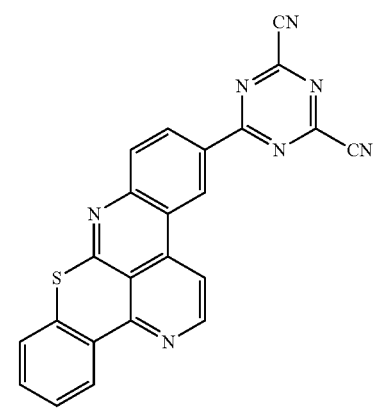 [SMILES: N#Cc1nc(C#N)nc(-c2ccc3nc4c5c(nccc5c3c2)-c2ccccc2S4)n1]

The base structure of the compounds of the invention can be represented by the routes outlined in schemes 1, 3 and 4 analogously to the thesis "Entwicklung neuer Synthesewege zu Pyridoacridinen" [Development of New Synthesis Routes to Pyridoacridines] (Stephan Rieder, Ludwig-Maximilian University of Munich, 2012), or by the route outlined in Scheme 2 analogously to Tetrahedron Letters 2013, 54, 2014-2017.

Scheme 1

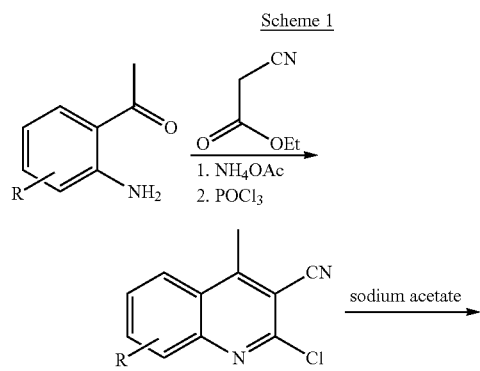

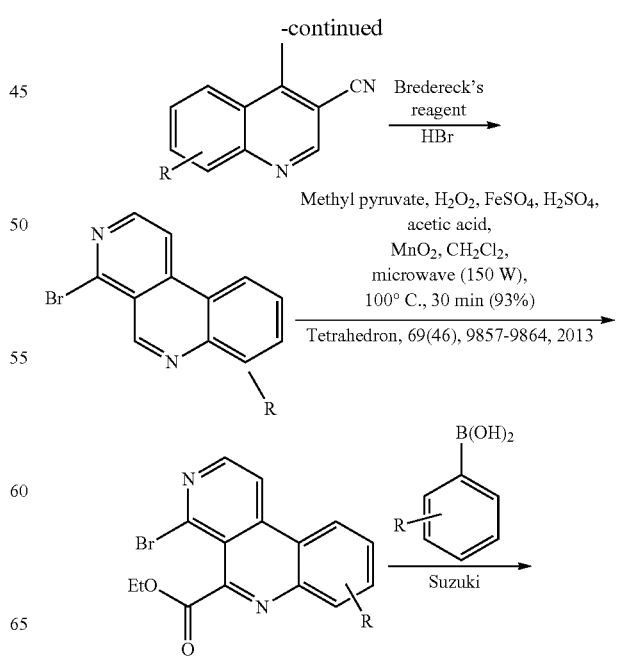

103
-continued
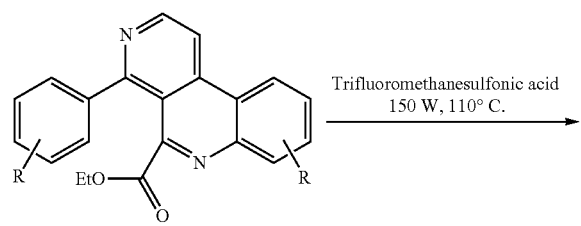
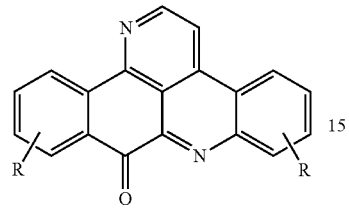
Scheme 2
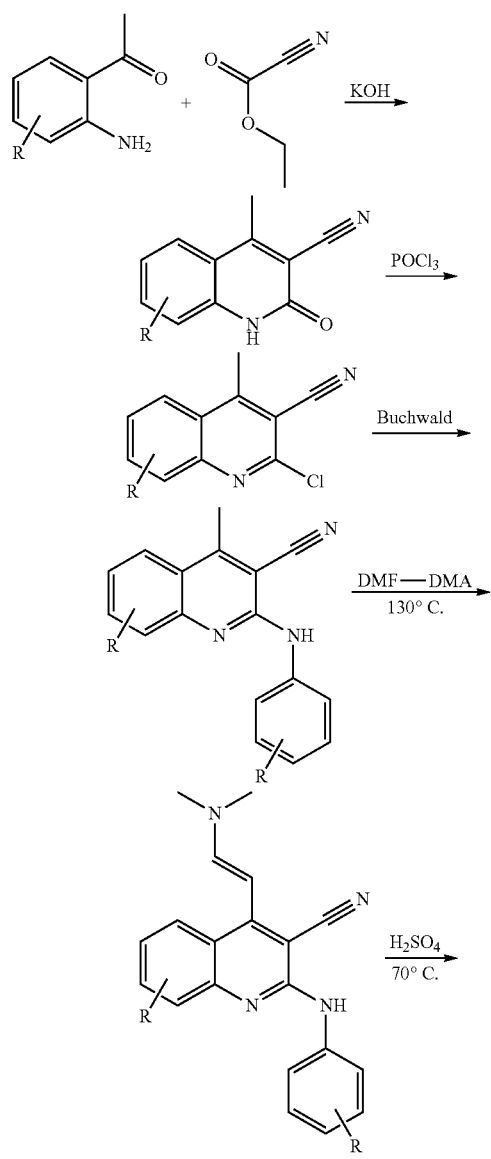
104
-continued
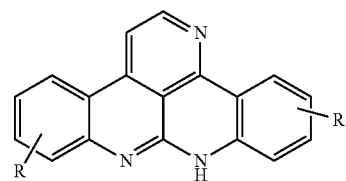
Scheme 3
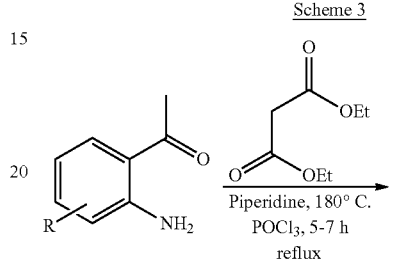
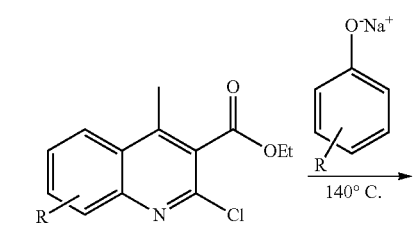
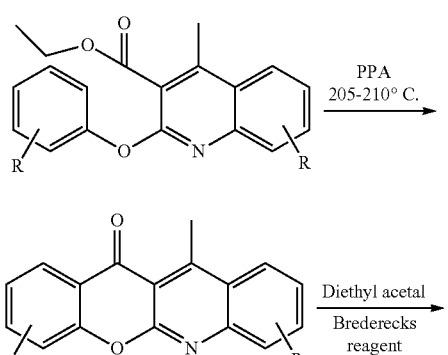
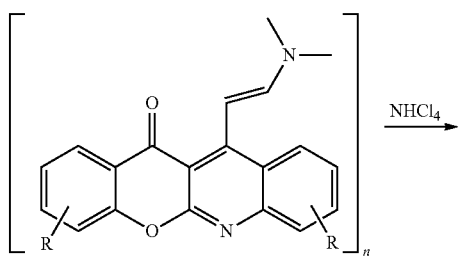
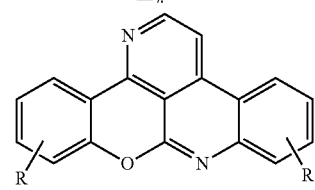

Scheme 4

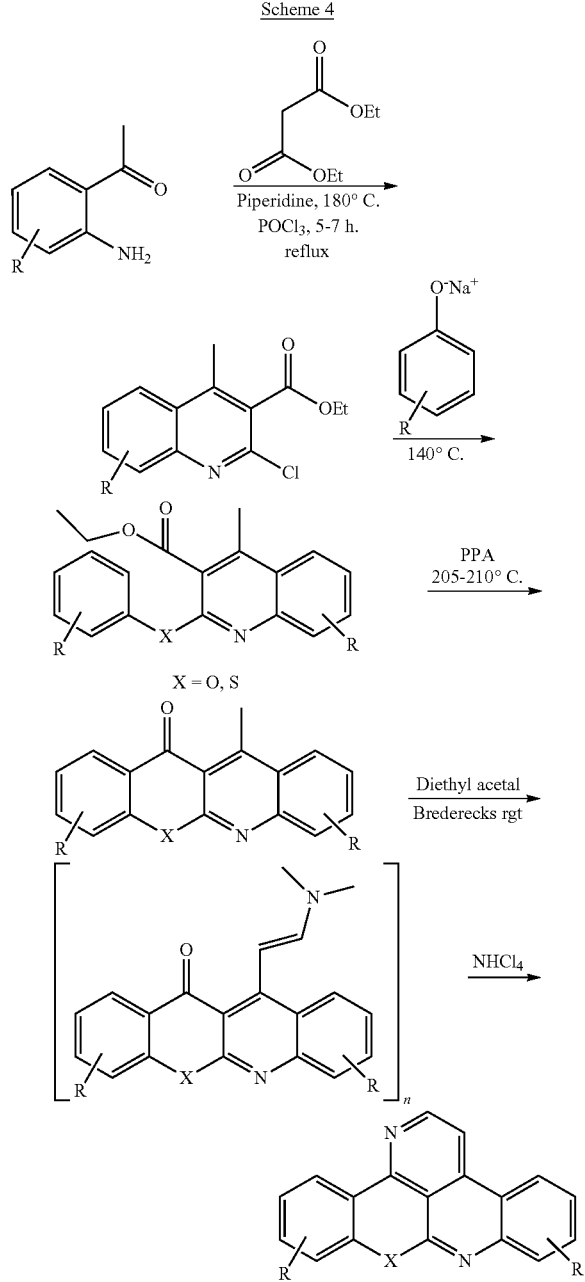

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole transport layer and/or in an exciton blocker layer and/or in a hole blocker layer. In a preferred embodiment of the invention, the compound of the invention is used as matrix material for red-phosphorescing emitters and/or as electron transport material in an electron transport layer or a hole blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. GBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608 or the as yet unpublished applications EP 16158460.2 or EP 16159829.7. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Additionally suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627 or in WO 2010/006680.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439 and the as yet unpublished application EP16179378.1. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

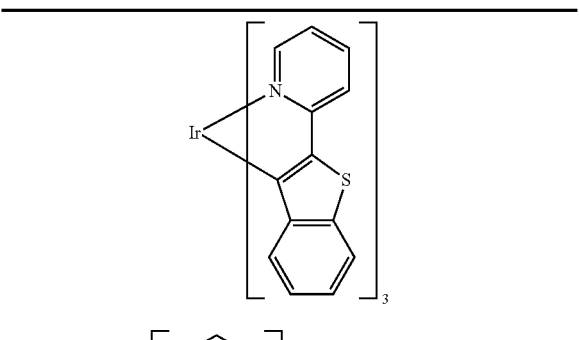
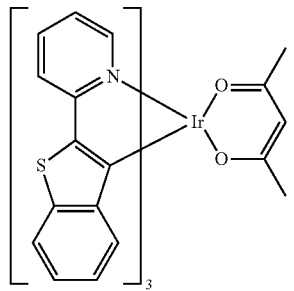
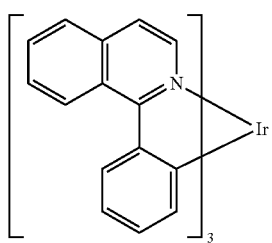
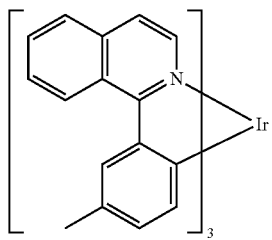
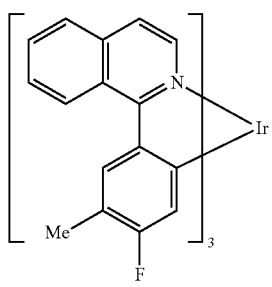
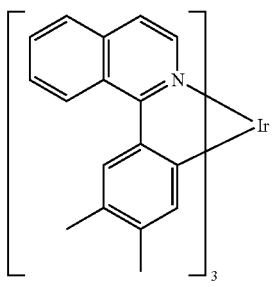
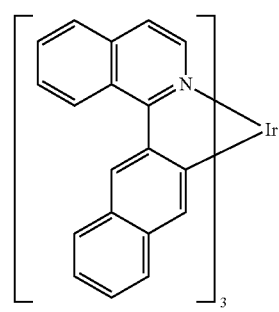
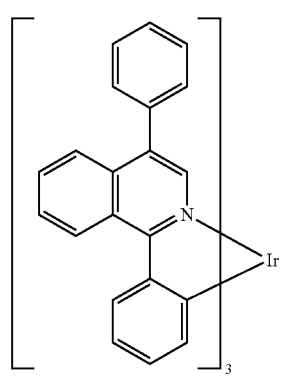
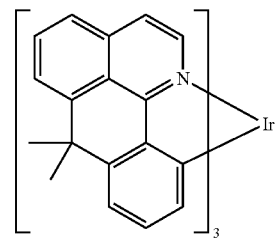
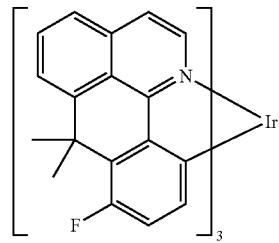
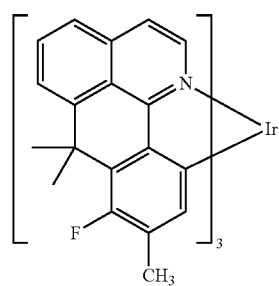

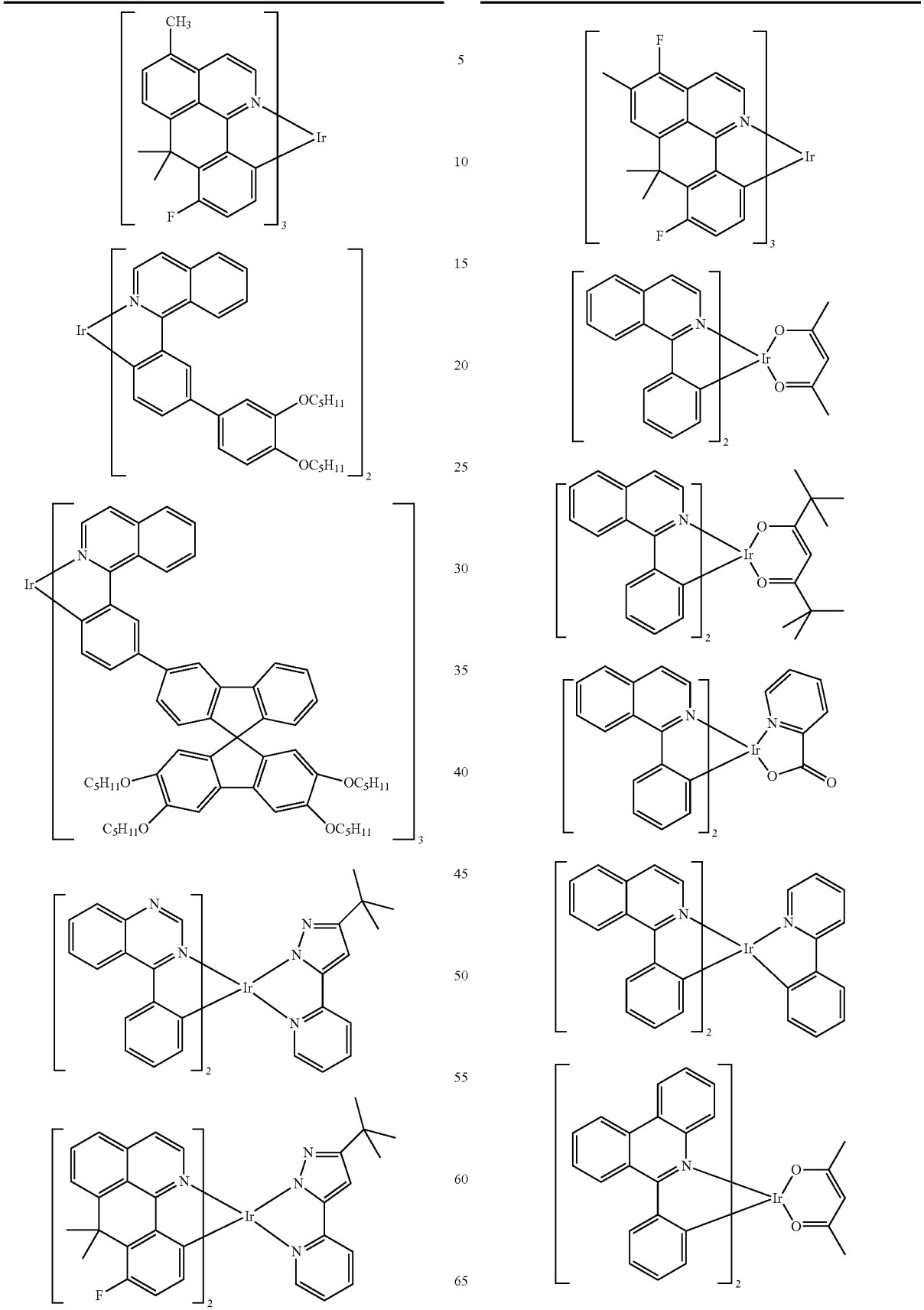

113
-continued
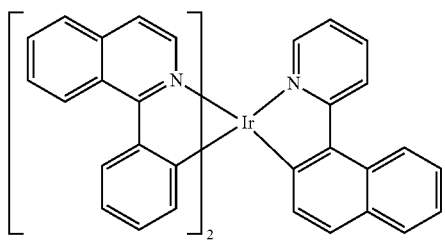
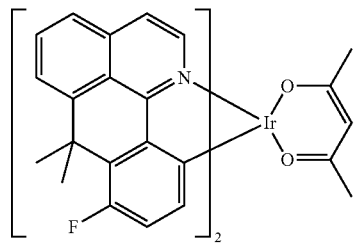
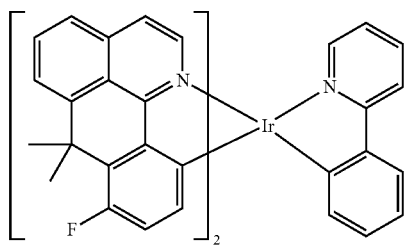
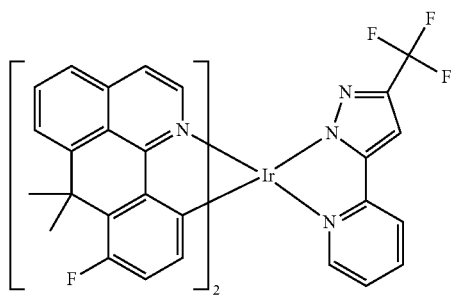
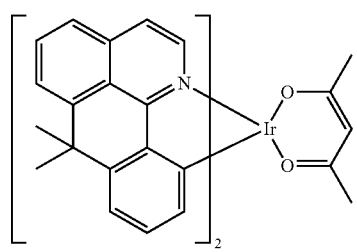
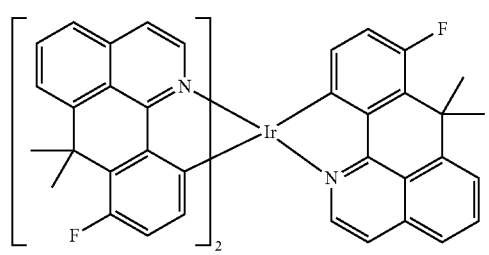
114
-continued
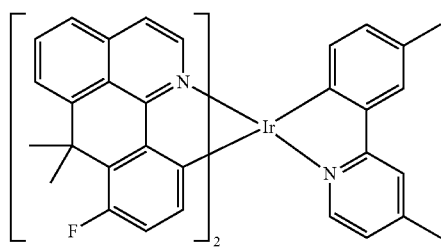
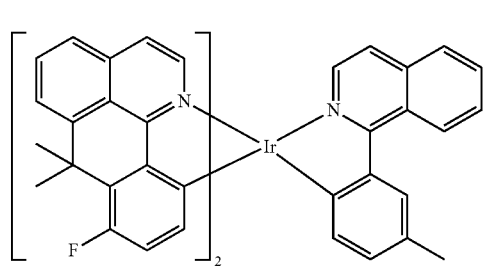
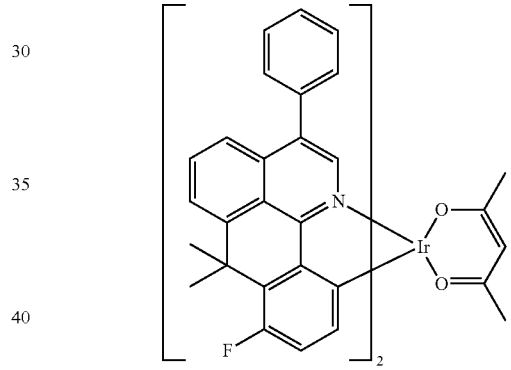
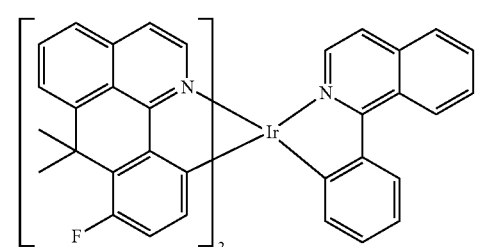
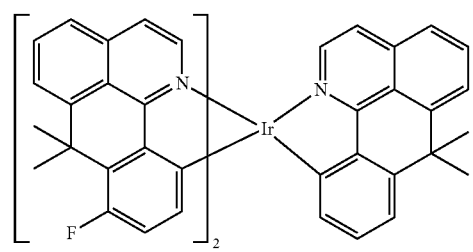

115
-continued
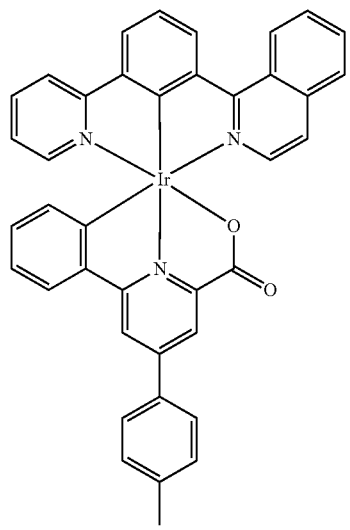
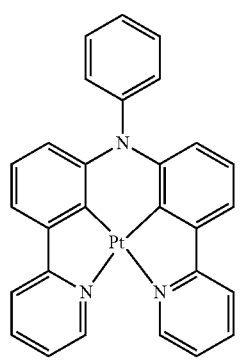
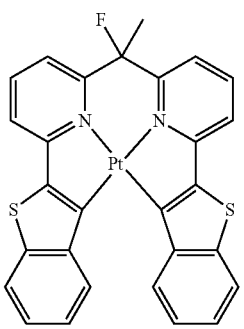
116
-continued
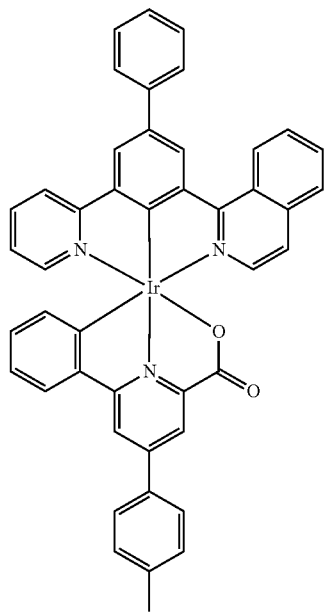
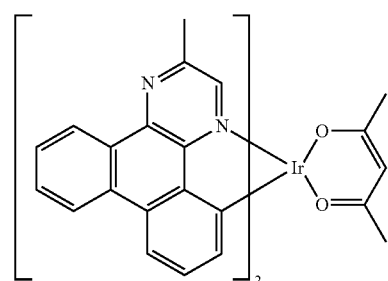
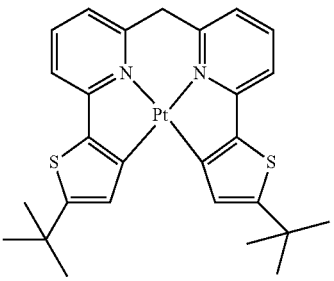
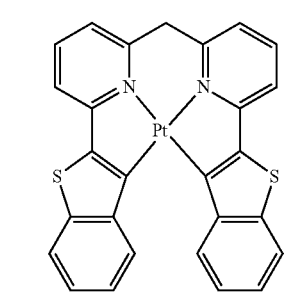

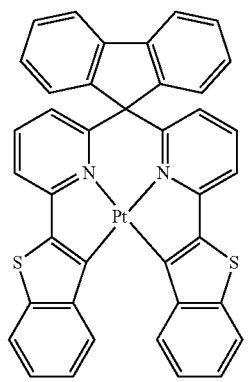
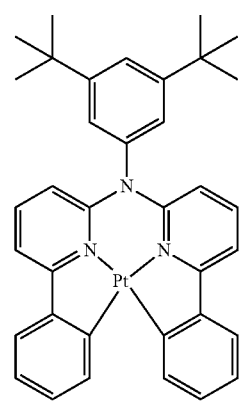
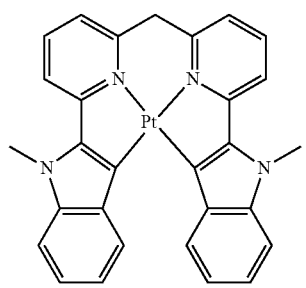
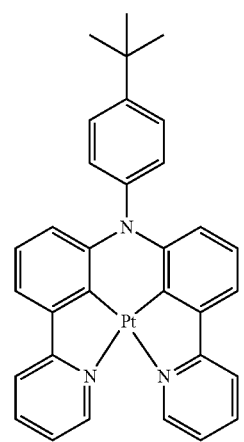
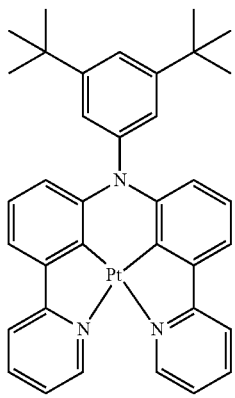
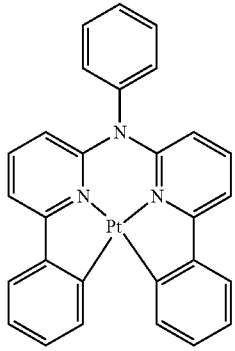
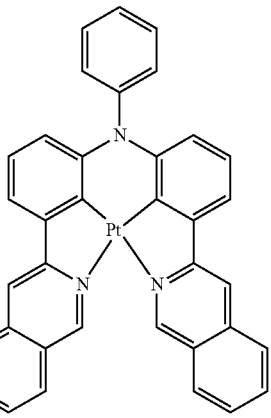
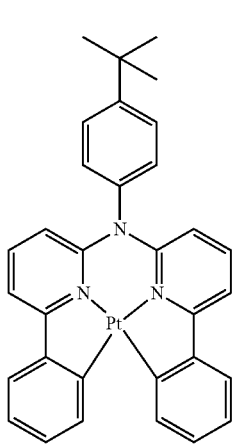

119
-continued
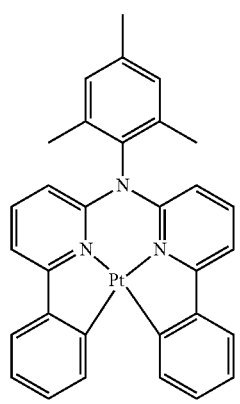
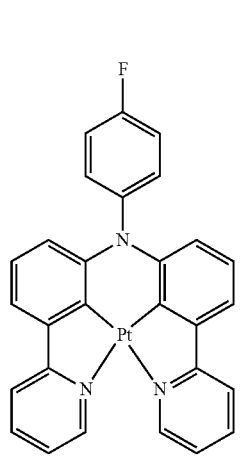
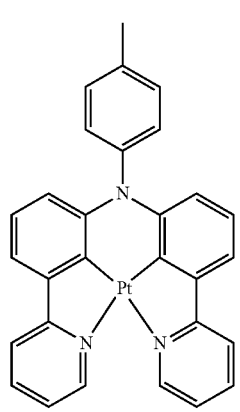
120
-continued

| 121 -continued | 122 -continued |
|---|---|
| 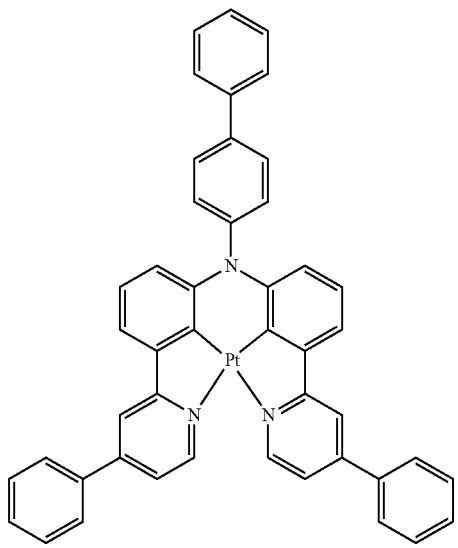 | 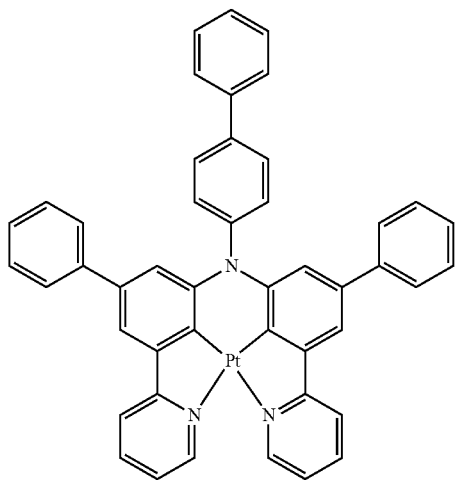 |
| 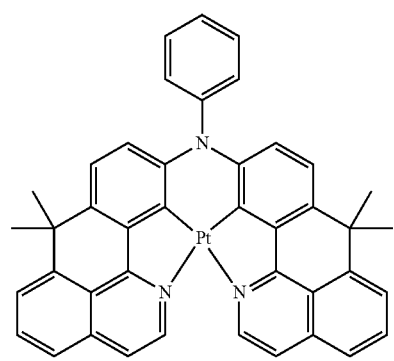 | 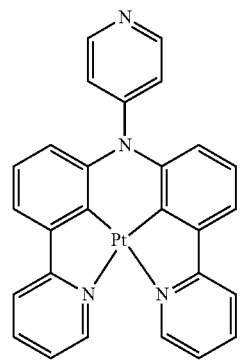 |
| 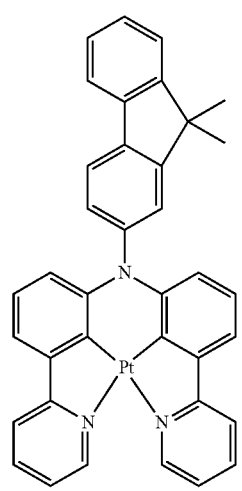 | 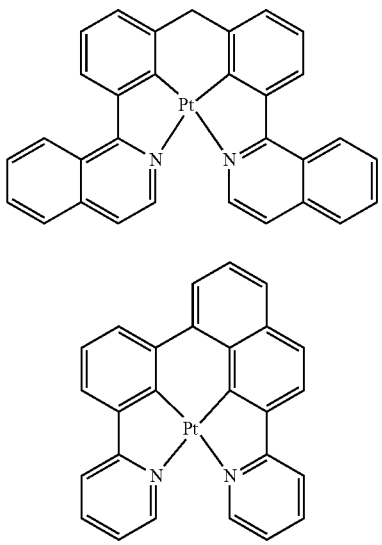 |

123
-continued
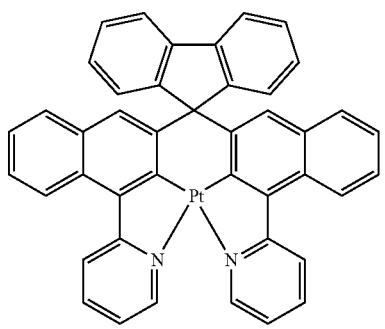
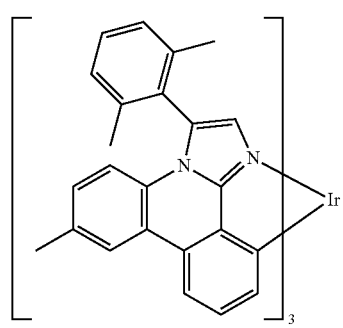
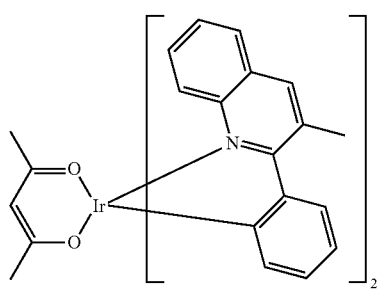
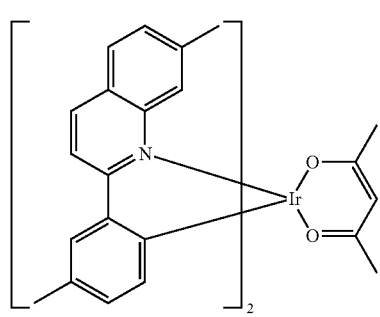
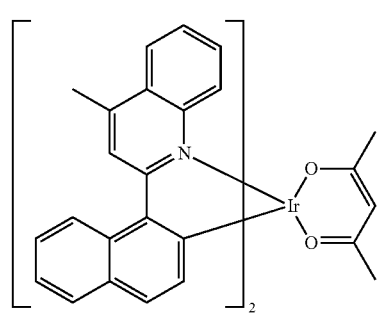
124
-continued
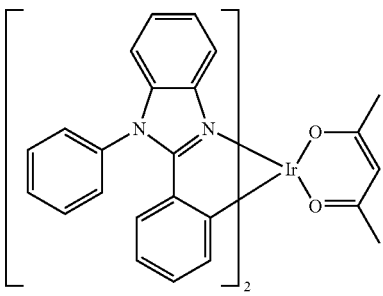
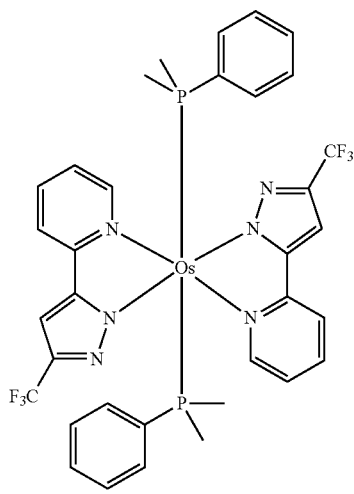
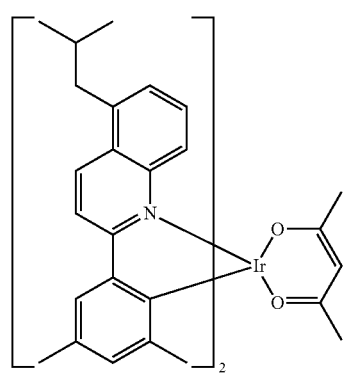
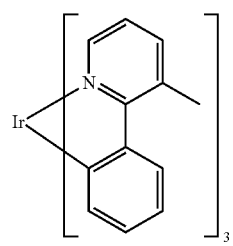
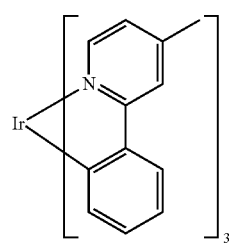

125
-continued
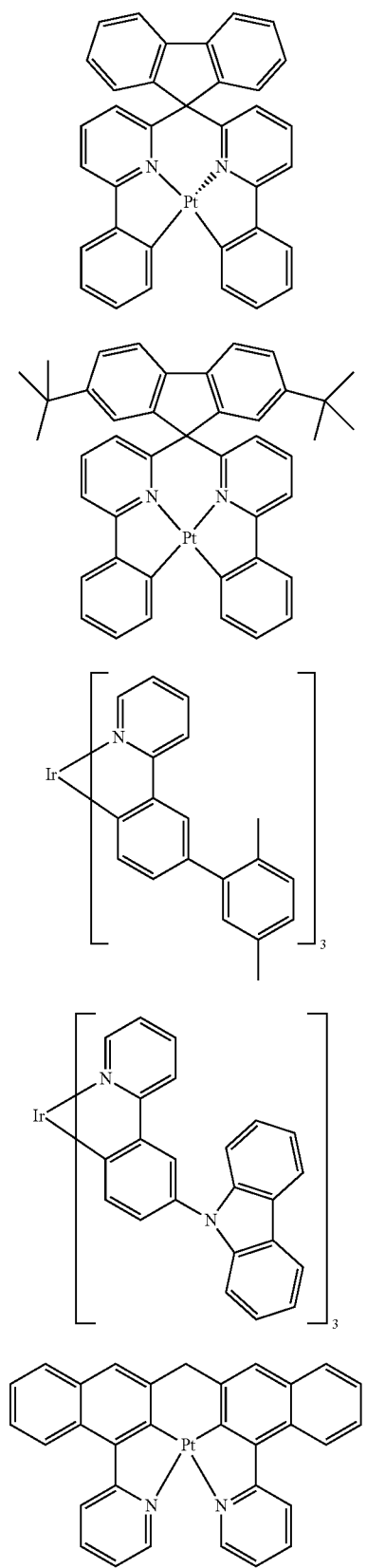
126
-continued
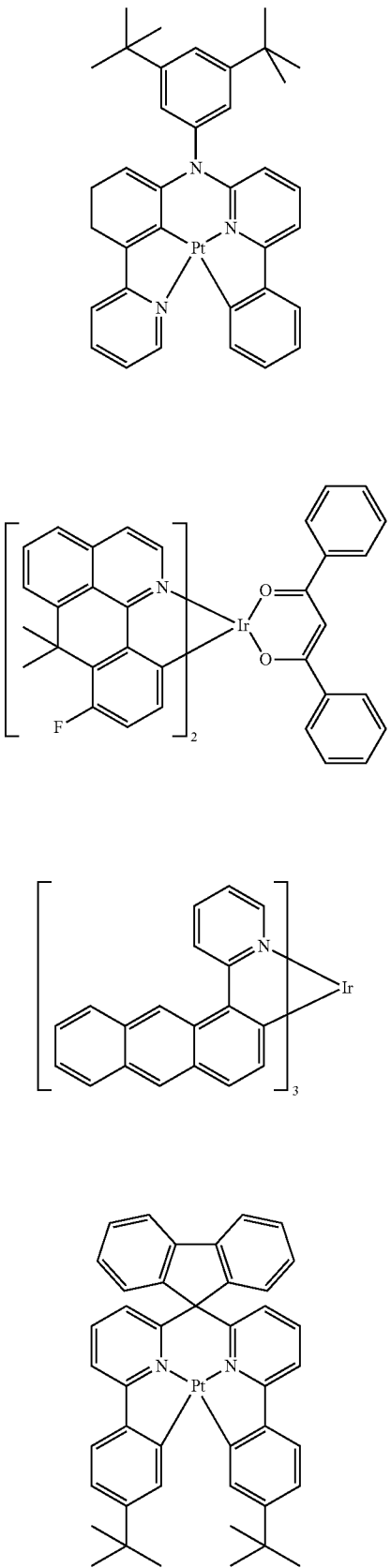

127
-continued
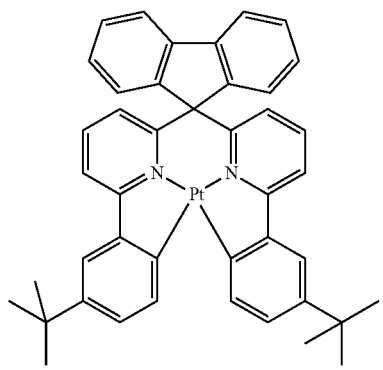
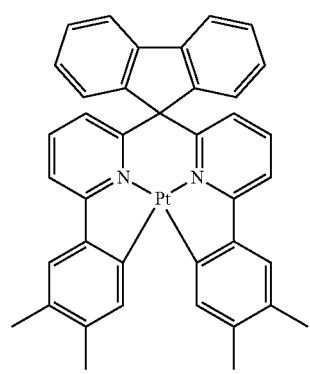
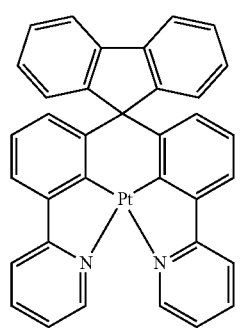
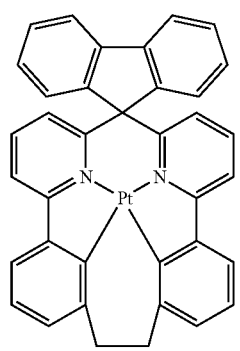
128
-continued
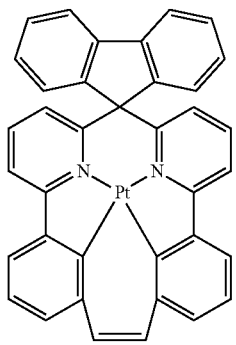
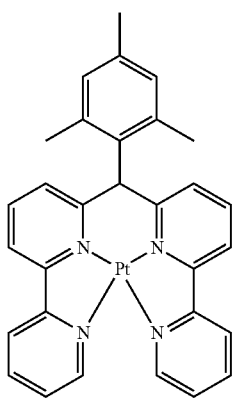
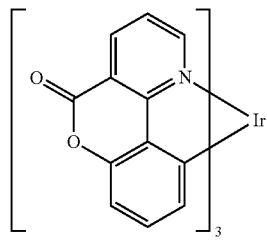
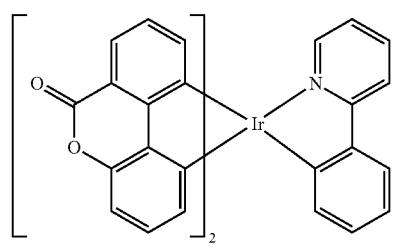
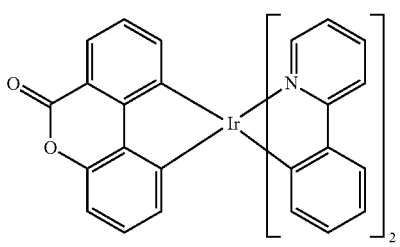

129
-continued
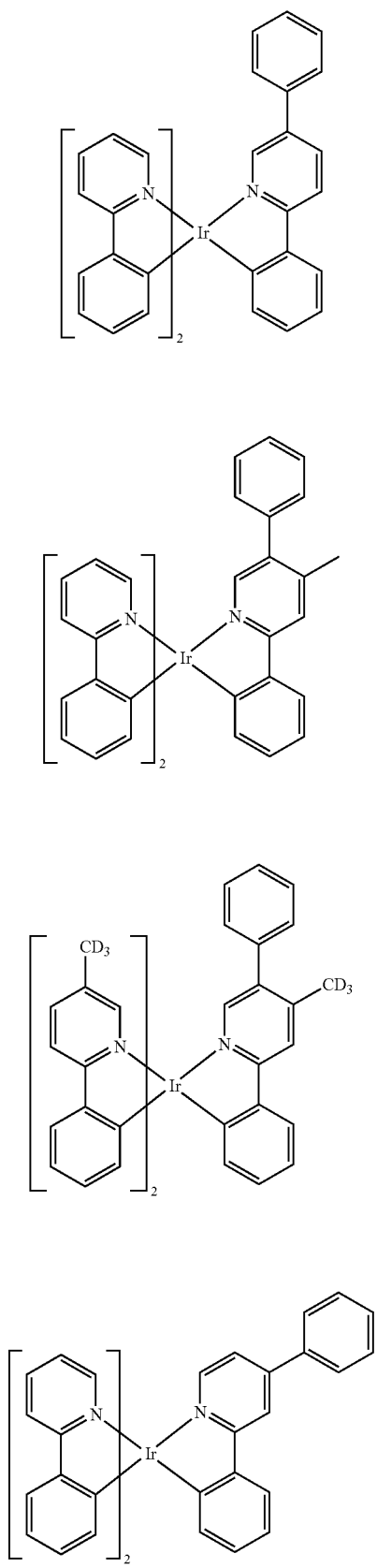
130
-continued
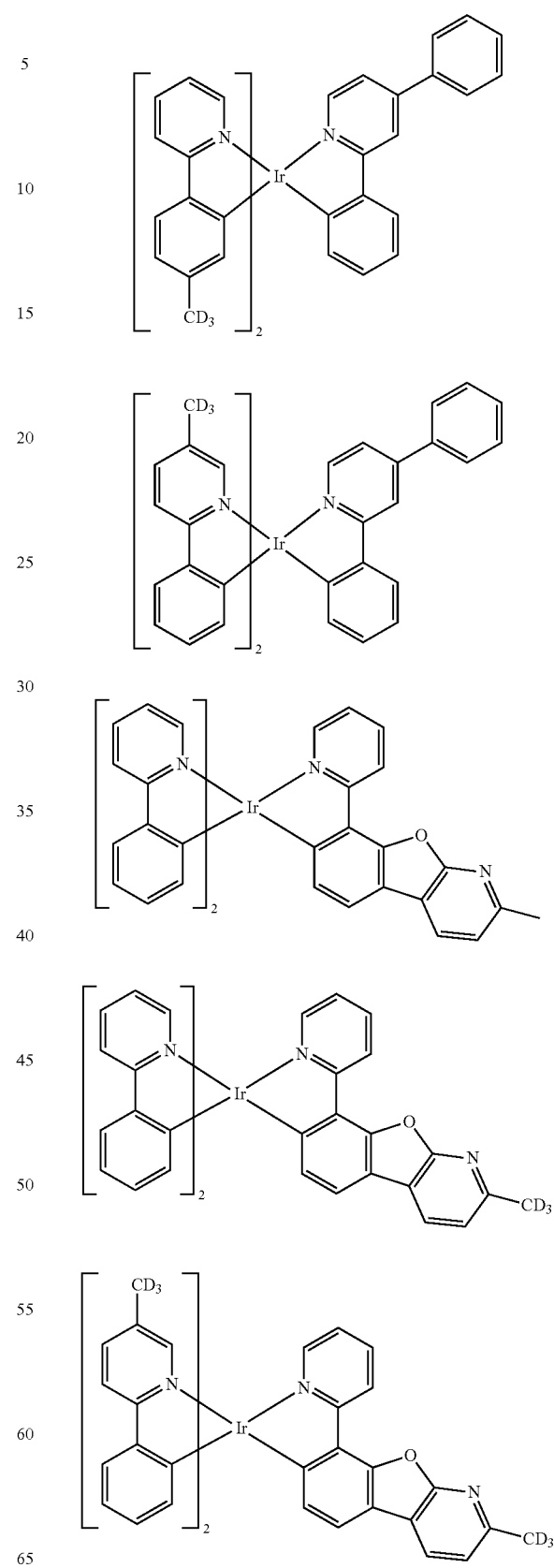

| 131 -continued | 132 -continued |
|---|---|
| 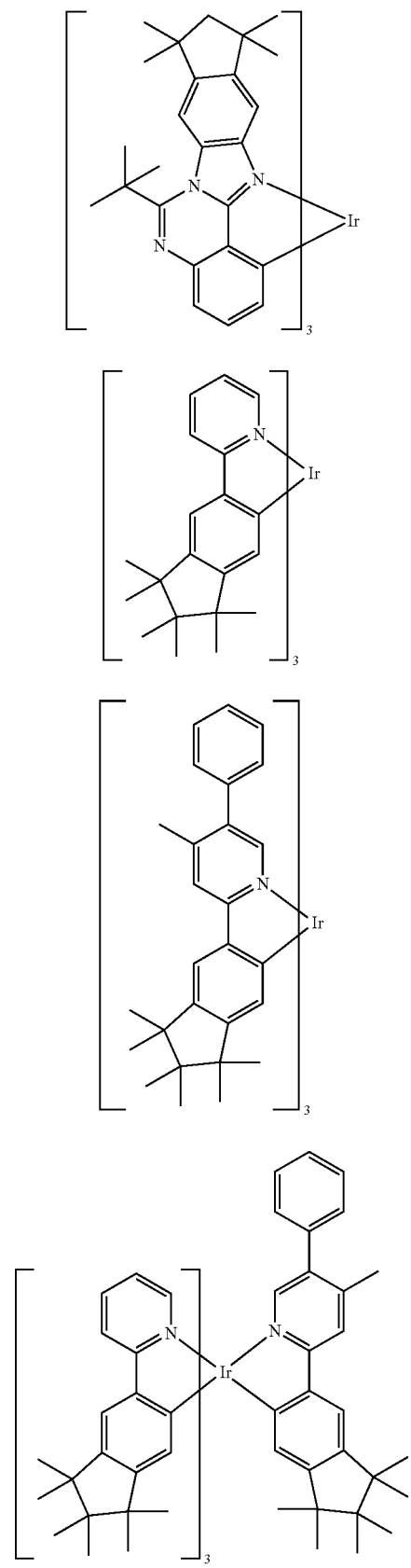 | 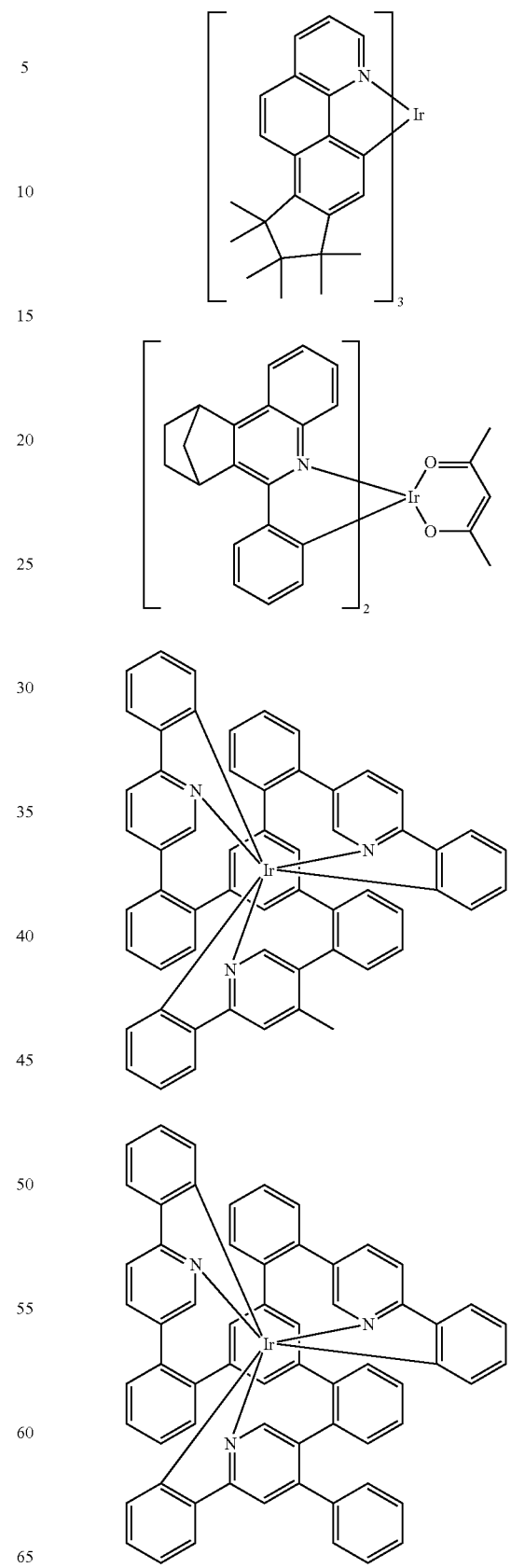 |

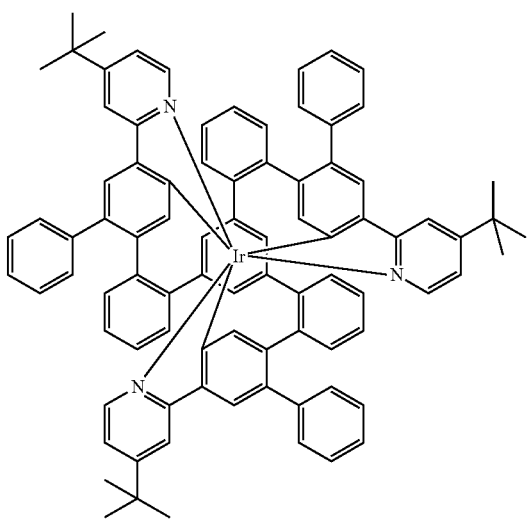

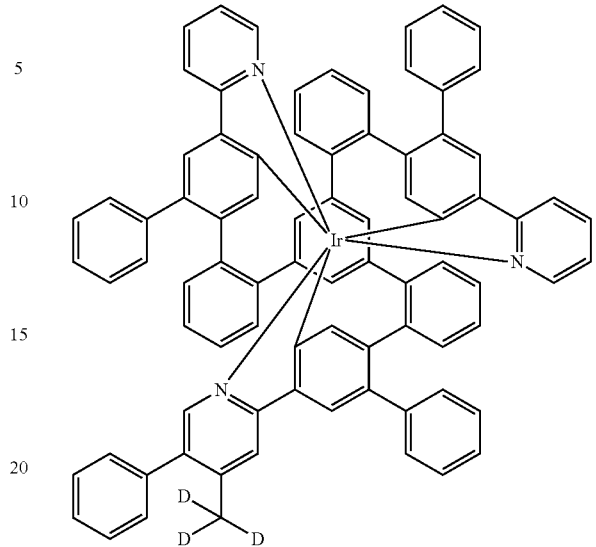

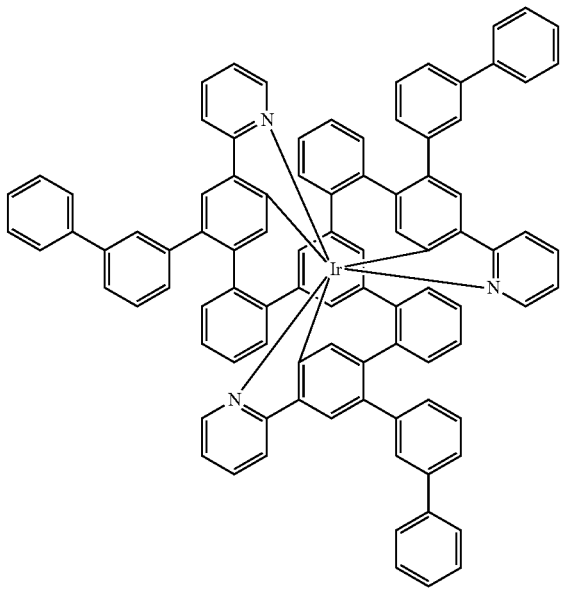

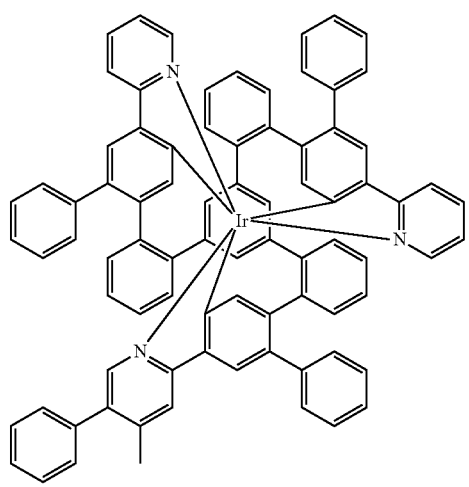

The compounds of the invention are especially also suitable as matrix materials for phosphorescent emitters in organic electroluminescent devices, as described, for example, in WO 98/24271, US 2011/0248247 and US 2012/0223633. In these multicolor display components, an additional blue emission layer is applied by vapor deposition over the full area to all pixels, including those having a color other than blue. It has been found that, surprisingly, the compounds of the invention, when they are used as matrix materials for the red and/or green pixels, still lead to very good emission together with the blue emission layer applied by vapor deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In a further preferred embodiment of the invention, the organic electroluminescent device contains the compound of the invention in an electron transport layer or in a hole blocker layer.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:

1. The compounds of the invention, used as matrix material for phosphorescent emitters, lead to long lifetimes.
2. The compounds of the invention lead to high efficiencies. This is especially true when the compounds are used as matrix material for a phosphorescent emitter.
3. The compounds of the invention lead to low operating voltages. This is especially true when the compounds are used as matrix material for a phosphorescent emitter.

These abovementioned advantages are not accompanied by a deterioration in the further electronic properties.

The invention is illustrated in more detail by the examples which follow, without any intention of restricting it thereby.

The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers. Further literature: thesis: "Entwicklung neuer Synthesewege zu Pyridoacridinen" by Stephan Raeder (2012), University of Munich.

a)
4-Methyl-2-oxo-1,2-dihydroquinoline-3-carbonitrile

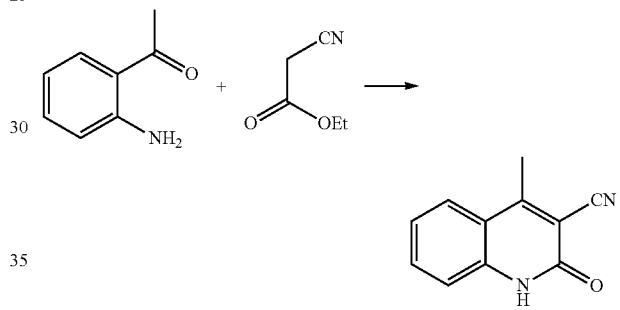

To 10.0 g (73.9 mmol) of 2-aminoacetophenone are added 10.0 g (88.4 mmol) of ethyl cyanoacetate. The mixture is heated under reflux at 200° C. in an oil bath for 1 h. Subsequently, the mixture is cooled down and 50 ml of ethanol are added. A light-colored precipitate forms, which is filtered off. In order to increase the yield, another 5 g of ethyl cyanoacetate can be added to the supernatant and it can be heated to 200° C. for a further 1.5 h. The residue is purified by suspending it in dichloromethane and then in petroleum benzene, separating it off as white crystals and drying. Yield: 5.4 g (29 mmol), 40% of theory.

The following compounds are prepared in an analogous manner:

| | Reactant 1 | Reactant 2 | Product | Yield |
|---|---|---|---|---|
| 1a | [structure with phenyl, aminoacetophenone] [887945-68-8] | [ethyl cyanoacetate structure] | [5-phenyl-4-methyl-3-CN quinolinone structure] | 37% |

-continued

| | Reactant 1 | Reactant 2 | Product | Yield |
|---|---|---|---|---|
| 2a | 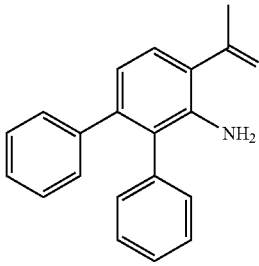 [353754-51-5] | 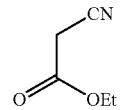 | 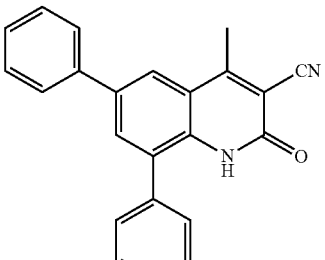 | 34% | b) 2-Chloro-4-methylquinoline-3-carbonitrile

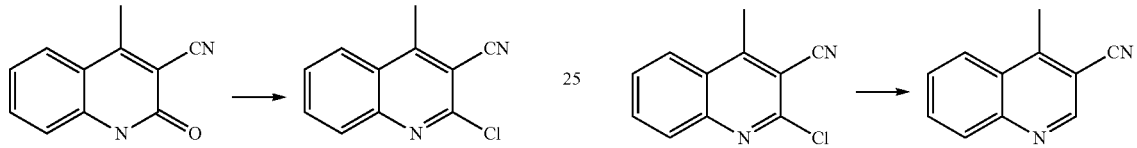

5 g (27 mmol) of 4-methyl-2-oxo-1,2-dihydroquinoline-3-carbonitrile are heated under reflux with 50 ml of phosphoryl chloride for 3 h. Subsequently, the phosphoryl chloride is drawn off under reduced pressure, ammonium chloride solution is added and the residue is filtered off. The residue is washed with water and recrystallized from ethanol. Yield: 5.5 g (27 mmol), 90% of theory.

The following compounds are prepared in an analogous manner:

c) 4-Methylquinoline-3-carbonitrile

To 15 g (74 mmol) of 2-chloro-4-methylquinoline-3-carbonitrile are added 8 g of sodium acetate and the mixture is suspended in about 800 ml of methanol. To this are added about 200 mg of palladium-charcoal (10%), and the mixture is hydrogenated under $H_2$ atmosphere at room temperature and standard pressure for 24 h. After the catalyst has been filtered off, a yellow-green solution is obtained, which, after removal of the methanol by rotary evaporation, forms a yellow residue. Purification is effected by means of flash chromatography on silica gel (eluent: dichloromethane:ethyl acetate=5:1). Yield: 12 g (71 mmol), 92% of theory.

| | Reactant 1 | Product | Yield |
|---|---|---|---|
| 1b | 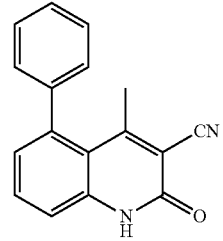 [SMILES: Cc1c(C#N)c(=O)[nH]c2cccc(-c3ccccc3)c12] | 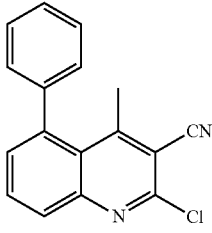 [SMILES: Cc1c(C#N)c(Cl)nc2cccc(-c3ccccc3)c12] | 89% |
| 2b | 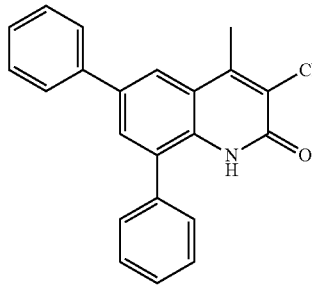 | 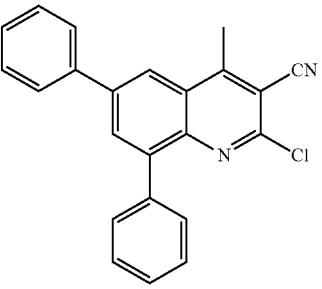 [SMILES: Cc1c(C#N)c(Cl)nc2c(-c3ccccc3)cc(-c3ccccc3)cc12] | 88% |

The following compounds are prepared in an analogous manner:

| | Reactant 1 | Product | Yield |
|---|---|---|---|
| 1c | 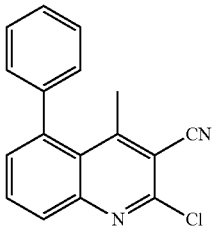 [SMILES: Cc1c(C#N)c(Cl)nc2cccc(-c3ccccc3)c12] | 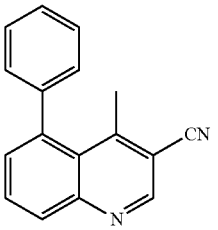 [SMILES: Cc1c(C#N)cnc2cccc(-c3ccccc3)c12] | 90% |
| 2c | 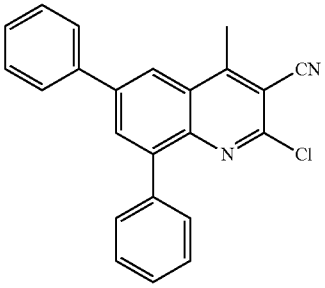 [SMILES: Cc1c(C#N)c(Cl)nc2c(-c3ccccc3)cc(-c3ccccc3)cc12] | 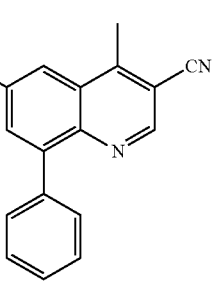 | 85% | d) 4-Bromobenzo[c][2,7]naphthyridine

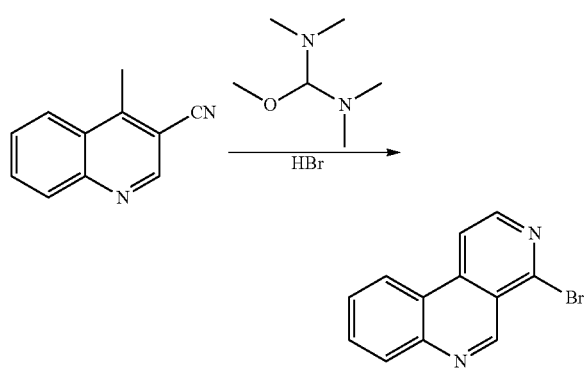

25 g (150 mmol) of 4-methylquinoline-3-carbonitrile are dissolved in 500 ml of DMF, and 50 g (290 mmol) of Bredereck's reagent are added. The mixture is converted in a microwave reactor at 150 W and max. 165° C. for 15 min.

The solvent is distilled off on a rotary evaporator and the residue is dissolved in 600 ml of hydrogen bromide in glacial acetic acid (40%) and 400 ml of glacial acetic acid. The reaction mixture is heated to 60° C. for 1 h, then transferred into 500 ml of water, neutralized with potassium carbonate and extracted with dichloromethane (4×150 ml). The organic phases are combined and dried over MgSO$_4$, and the solvent is distilled off on a rotary evaporator. The residue is purified by means of flash column chromatography (dichloromethane:methanol=97:3). Yield: 36 g (136 mmol), 95% of theory.

The following compounds are prepared in an analogous manner:

| | Reactant 1 | Product | Yield |
|---|---|---|---|
| 1d | 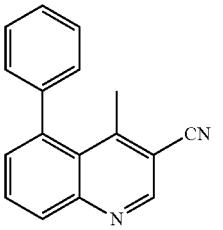 [SMILES: Cc1c(C#N)cnc2cccc(-c3ccccc3)c12] | 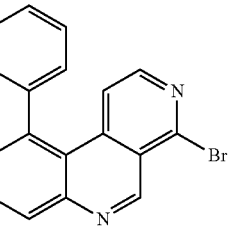 | 92% |

| Reactant 1 | Product | Yield |
|---|---|---|
| 2d | | 90% | e) Ethyl 4-bromobenzo[c][2,7]naphthyridine-5-carboxylate

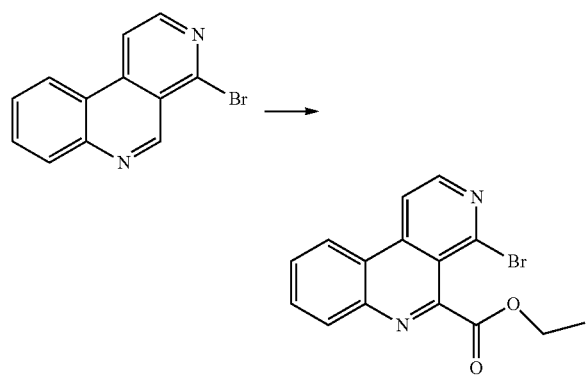

12 g (45 mmol) of ethyl 4-bromo-5,6-dihydrobenzo[c][2,7]naphthyridine-5-carboxylate are dissolved in 400 ml of dichloromethane, and 39 g (450 mmol) of manganese(IV) oxide. The mixture was converted in a microwave reactor at 150 W at max. 7.0 bar and 100° C. for 10 min (ramp time: 6 min). After being cooled down, the reaction mixture is filtered and washed with methanol, and the solvent is distilled off on a rotary evaporator. Yield: 14 g (42 mmol), 98% of theory.

The following compounds are prepared in an analogous manner:

| Reactant 1 | Product | Yield |
|---|---|---|
| 1e | | 93% |
| 2e | | 90% |

143 f) Ethyl 4-phenylbenzo[c][2,7]naphthyridine-5-carboxylate

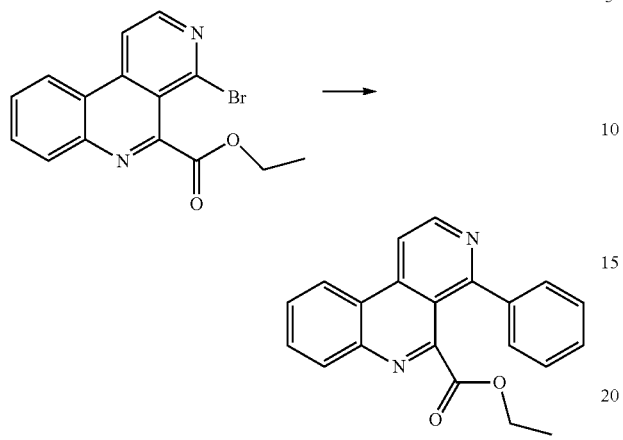

60 g (180 mmol) of ethyl 4-bromobenzo[c][2,7]naphthyridine-5-carboxylate and 4 g (18 mmol) of palladium(II) acetate are suspended in 400 ml of THF. To this are added a solution of 33 g (270 mmol) of benzeneboronic acid and 450 ml (540 mmol) of 1 M potassium carbonate solution in 400 ml of THF. The mixture is heated under reflux under a nitrogen atmosphere for 40 h, then transferred into 200 ml of water and extracted with dichloromethane (4×200 ml). The combined organic phases are dried over MgSO₄, and the solvent is distilled off on a rotary evaporator. The residue is purified by means of flash column chromatography (dichloromethane:ethyl acetate=3:1). Yield: 35 g (106 mmol), 60% of theory.

The following compounds are prepared in an analogous manner:

144 g) 1,8-Diazabenzo[fg]naphthacen-9-one

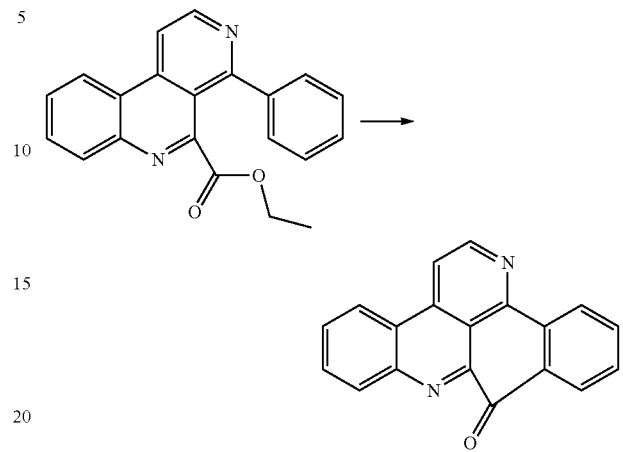

20 g (60 mmol) of ethyl 4-phenylbenzo[c][2,7]naphthyridine-5-carboxylate are dissolved in 100 ml of trifluoromethanesulfonic acid and converted with the aid of a microwave (reaction conditions: 150 W, reaction time 15 min, ramp time: 1 min, maximum pressure 7.0 bar, max. 85° C.). Subsequently, the mixture is admixed with 200 ml of ice-water, neutralized with K₂CO₃ and extracted with dichloromethane (3×250 ml). The combined organic phases are dried over MgSO₄ and concentrated under reduced pressure. The residue is purified by means of flash column chromatography (dichloromethane:ethyl acetate=3:1). Yield: 7 g (24 mmol), 42% of theory.

The following compounds are prepared in an analogous manner:

| | Reactant 1 | Product | Yield |
|---|---|---|---|
| 1f | | | 57% |
| 2f | | | 53% |

| Reactant 1 | Product | Yield |
|---|---|---|
| 1g | | 41% |
| 2g | | 37% | h) 11-Methyl-5-oxa-6-azanaphthacen-12-one

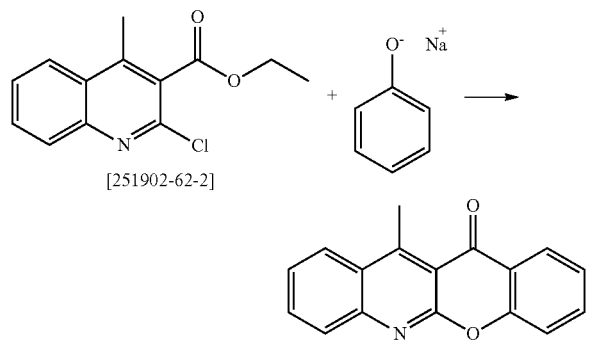

52.6 g (211 mmol) of ethyl 2-chloro-4-methylquinoline-3-carboxylate are dissolved together with 54 g (317 mmol) of sodium phenoxide in 100 ml of dimethylformamide and reacted at 155° C. for 6 h. Thereafter, the solvent is removed on a rotary evaporator, 10 times the amount of polyphosphoric acid is added to the residue and the mixture is heated to 130° C. for 5 h. The mixture is poured onto ice and neutralized with 6 N NaOH. The neutralized solution is extracted with ethyl acetate (4×500 ml). The combined organic phases are dried over MgSO₄, and the solvent is distilled off on a rotary evaporator. The residue is purified by means of flash column chromatography (dichloromethane: ethyl acetate=3:1). Yield: 13.8 g (52 mmol), 25% of theory.

The following compounds are prepared in an analogous manner:

| | Reactant 1 | Reactant 2 | Product | Yield |
|---|---|---|---|---|
| 1h | | | | 26% |
| 2h | | | | 25% | j) 9-Oxa-1,8-diazabenzo[fg]naphthacene l) 4-Methyl-2-phenylaminoquinoline-3-carbonitrile

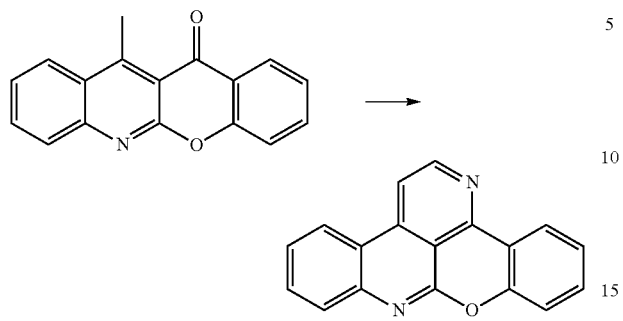

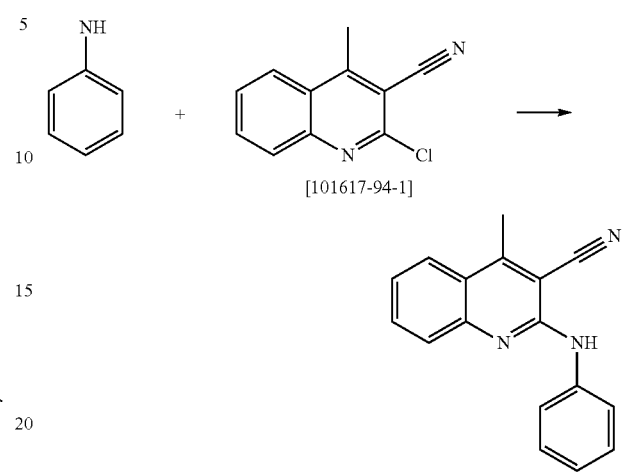

15.7 g (60 mmol) of 11-methyl-5-oxa-6-azanaphthacen-12-one are dissolved together with 22 g (150 mmol) of diethyl acetal in 10 ml of DMF and reacted in a laboratory microwave at 150° C. and 200 W for 3 h. Thereafter, the solvent is removed on a rotary evaporator, 10 times the amount of $NH_4OAc$ is added to the residue and the mixture is heated to 114° C. for 2 h. The mixture is poured onto ice and extracted with dichloromethane (4×50 ml). The combined organic phases are dried over $MgSO_4$, and the solvent is distilled off on a rotary evaporator. The residue is purified by means of flash column chromatography (dichloromethane:ethyl acetate=3:1). Yield: 7.8 g (27 mmol), 50% of theory.

The following compounds are prepared in an analogous manner:

38 g (190 mmol) of 2-chloro-4-methyl-3-quinolinecarbonitrile are dissolved together with 27 g (285 mmol) of aniline in 100 ml of ethylene glycol and heated to 140° C. for 6 h. Subsequently, the mixture is transferred to 50 ml of water and extracted with dichloromethane (3×50 ml). The combined organic phases are dried over $MgSO_4$, and the solvent is distilled off on a rotary evaporator. The residue is purified by means of flash column chromatography (dichloromethane:methanol=3:1). Yield: 39 g (152 mmol), 80% of theory.

The following compounds are prepared in an analogous manner:

| | Reactant 1 | Product | Yield |
|---|---|---|---|
| 1j | | | 52% |
| 2j | | | 46% |
| 3j | | | 48% |

| | Reactant 1 | Reactant 2 | Product | Yield |
|---|---|---|---|---|
| 1i | 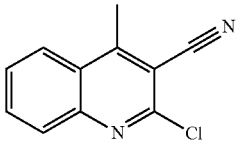 | 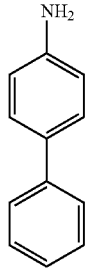 [92-67-1] | 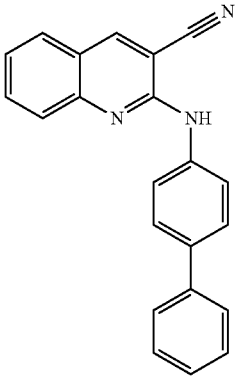 [SMILES: N#Cc1cc2ccccc2nc1Nc1ccc(-c2ccccc2)cc1] | 76% |
| 2i | 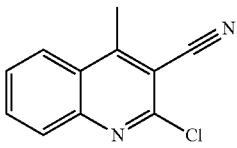 | 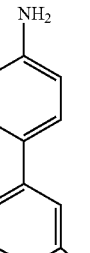 [1370034-59-5] | 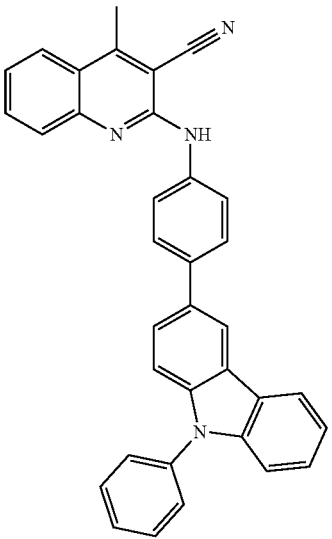 [SMILES: Cc1c(C#N)c(Nc2ccc(-c3ccc4c(c3)c3ccccc3n4-c3ccccc3)cc2)nc2ccccc12] | 78% |
k) 4-((E)-2-Dimethylaminovinyl)-2-phenylamino-quinoline-3-carbonitrile
-continued
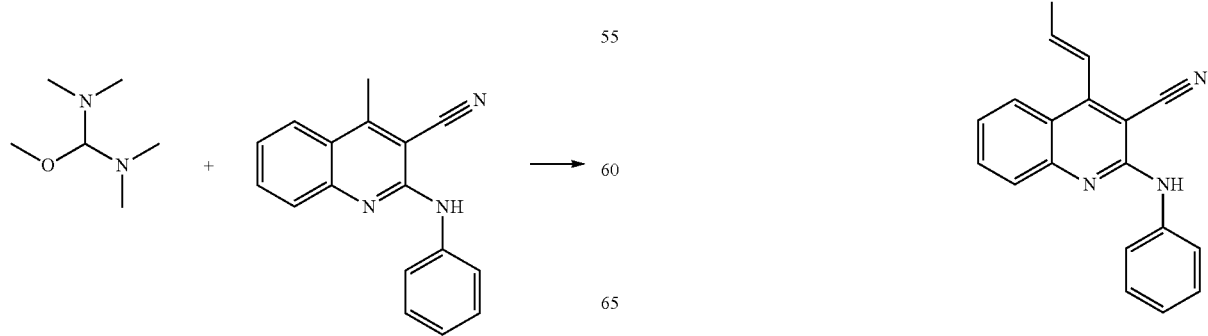

46 g (185 mmol) of 4-methyl-2-phenylaminoquinoline-3-carbonitrile together with 99.6 g (835 mmol) of d($!C258AAEC-1A15-4881-9D65-2CF1E685CC9A!$)imethoxymethyldimethylamine in 400 ml of N($!2F08A8C9-A65C-45E5-BE32-BC64E08B605A!$),N-dimethylformamide (400 ml) are heated to 100° C. for 12 h. After cooling, 1000 ml of ice-water are added. The solids are filtered off with suction and washed with a little heptane. Yield: 50 g (160 mmol), 89% of theory.

The following compounds are prepared in an analogous manner:

| | Reactant 1 | Product | Yield |
|---|---|---|---|
| 1k | | | 80% |
| 2k | | | 77% |
| 3k | [1527467-30-6] | | 63% |

-continued

| Reactant 1 | Product | Yield |
|---|---|---|
| 4k [498564-15-1] | | 64% |
| 5k [123858-53-7] | | 63% |
| 6k | | 60% | l) 9H-1,8,9-Triazabenzo[fg]naphthacene

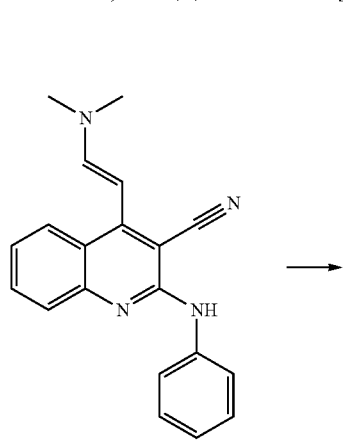

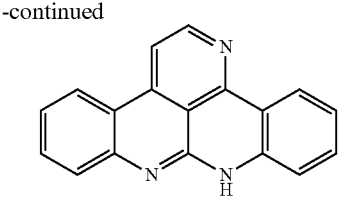

27.3 g (87 mmol) of 4-((E)-2-dimethylaminovinyl)-2-phenylaminoquinoline-3-carbonitrile are suspended in 60 ml of conc. $H_2SO_4$ under protective gas and heated to 70° C. for 4 h. After cooling, the mixture is added to ice-water, the pH is adjusted to 9 with $Na_2CO_3$ solution, and the mixture is extracted with ethyl acetate. After concentration, the product is purified by chromatography (methanol:dichloromethane 1:2). Yield: 50 g (160 mmol), 89% of theory.

The following compounds are prepared in an analogous manner:

| | Reactant 1 | Product | Yield |
|---|---|---|---|
| 11 | 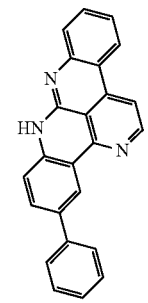 [SMILES: c1ccc(-c2ccc3c(c2)-c2nccc4c2c(nc2ccccc24)N3)cc1] | | 84% |
| 21 | 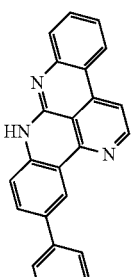 | | 86% | m) 1,8,11,13-Tetraazabenzo[fg]naphthacen-9-one

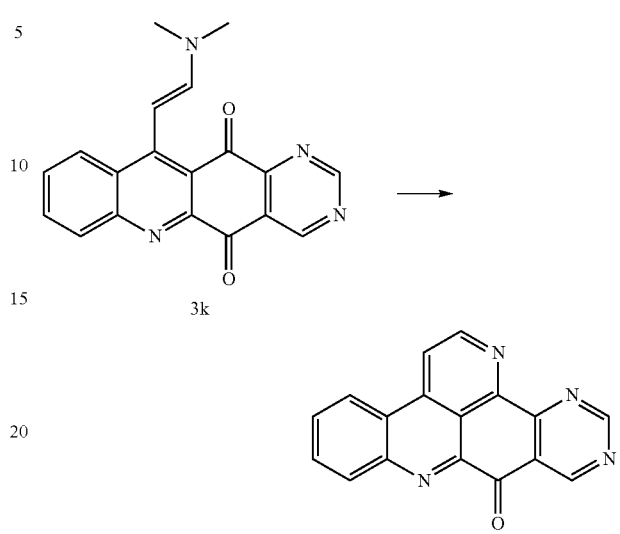

24.7 g (75 mmol) of 11-((E)-2-dimethylaminovinyl)-1,3,6-triazanaphthacene-5,12-dione together with 28.9 g (375 mmol) of ammonium acetate in 400 ml ethanol are heated under reflux for 3 h. The solids are filtered off with suction and washed with a little heptane. Yield: 19.1 g (67 mmol), 90% of theory.

The following compounds are prepared in an analogous manner:

| | Reactant 1 | Product | Yield |
|---|---|---|---|
| 1m | | | 86% |
| 2m | 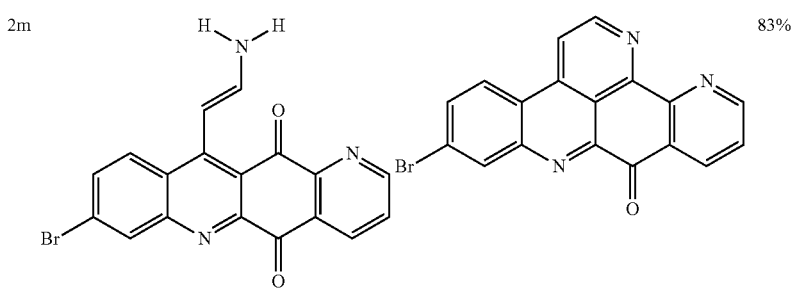 | | 83% |

| Reactant 1 | Product | Yield |
|---|---|---|
| 3m | | 84% | n) Spiro Synthesis

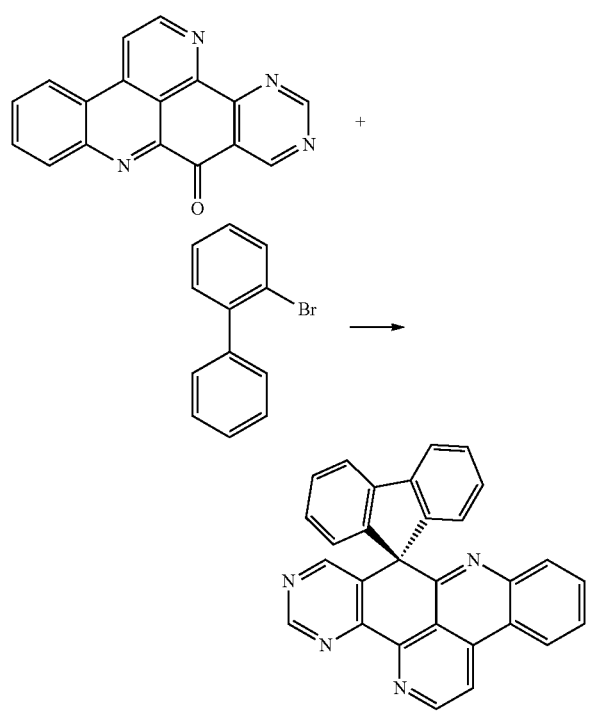

A 1 l four-neck flask is initially charged with 23 g (99 mmol) of 2-bromobiphenyl in 100 ml of THF and cooled to −78° C. By means of a dropping funnel, 41.0 ml (103 mmol) of n-BuLi (2.5 M in n-hexane) are added dropwise at this temperature and the mixture is stirred for 1 h. Subsequently, 13 g (49 mmol) of 1,8,11,13-tetraazabenzo[fg]naphthacen-9-one, dissolved in 300 ml of THF, are added by means of a dropping funnel and the reaction is warmed to room temperature within 3 h. This is followed by hydrolysis with 500 ml of water and removal of the organic solvents on a rotary evaporator. The solid that precipitates out is filtered, suspended in 400 ml of glacial acetic acid and, after addition of 150 ml of concentrated hydrochloric acid, stirred at 100° C. for 2 h. After cooling to room temperature, 400 ml of water are added, and the precipitated solids are filtered off and washed with 200 ml of water, 200 ml of ethanol and lastly with 200 ml of n-heptane. The solids are subjected to hot extraction and recrystallization with n-heptane/toluene over alumina. Further purification is effected by means of recrystallization from toluene/heptane and zone sublimation (310° C., $10^{-5}$ bar). Yield: 15.9 g (37 mmol), 83% of theory The following compounds are prepared in an analogous manner:

| Reactant 1 | Product | Yield |
|---|---|---|
| 1n | | 82% |

-continued
| | Reactant 1 | Product | Yield |
|---|---|---|---|
| 2n | | | 79% |
| 3n | | | 81% |
| 4n | | | 86% |
| 5n | 2r | | 65% |
o) 9-Phenyl-9H-1,8,9-triazabenzo[fg]naphthacene
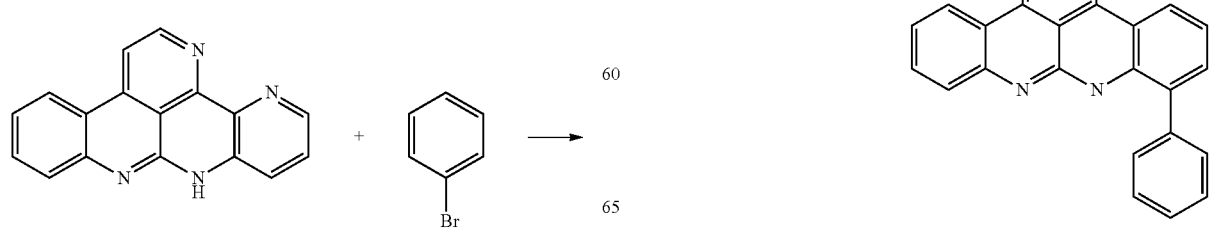

A degassed solution of 23 g (147 mmol) of bromobenzene and 39 g (147 mmol) of 9H-1,8,9-triazabenzo[fg]naphthacene in 600 ml of toluene is saturated with $N_2$ for 1 h. Added to the solution thereafter are first 2.09 ml (8.6 mmol) of P(tBu)$_3$, then 1.38 g (6.1 mmol) of palladium(II) acetate, and then 17.7 g (185 mmol) of NaOtBu are added in the solid state. The reaction mixture is heated under reflux for 1 h. After cooling to room temperature, 500 ml of water are added cautiously. The aqueous phase is washed with 3×50 ml of toluene, dried over MgSO$_4$, and the solvent is removed under reduced pressure. Thereafter, the crude product is purified by chromatography using silica gel with heptane/ethyl acetate (20/1). The residue is recrystallized from toluene and finally sublimed under high vacuum (p=5×10$^{-6}$ mbar). The yield is 40 g (115 mmol), corresponding to 80% of theory.

The following compounds are prepared in an analogous manner:

| | Reactant 1 | Reactant 2 | Product | Yield |
|---|---|---|---|---|
| 1o | 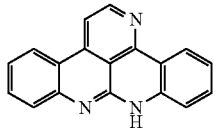 [SMILES: c1ccc2c(c1)Nc1nc3ccccc3c3ccnc-2c13] | 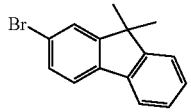 [SMILES: CC1(C)c2ccccc2-c2ccc(Br)cc21] | 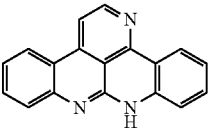 [SMILES: c1ccc2c(c1)Nc1nc3ccccc3c3ccnc-2c13] | 83% |
| 2o | 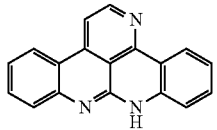 [SMILES: c1ccc2c(c1)Nc1nc3ccccc3c3ccnc-2c13] | 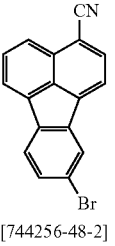  [744256-48-2] | 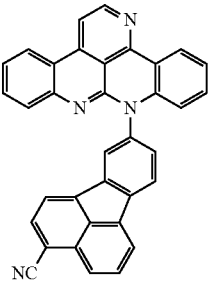 [SMILES: N#Cc1ccc2c3c(cccc13)-c1ccc(N3c4ccccc4-c4nccc5c4c3nc3ccccc35)cc1-2] | 81% |
| 3o | 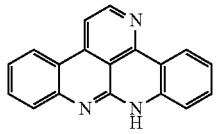 [SMILES: c1ccc2c(c1)Nc1nc3ccccc3c3ccnc-2c13] | 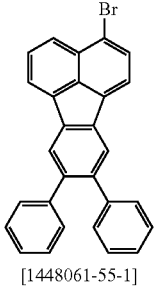 [SMILES: Brc1ccc2c3c(cccc13)-c1cc(-c3ccccc3)c(-c3ccccc3)cc1-2]  [1448061-55-1] | 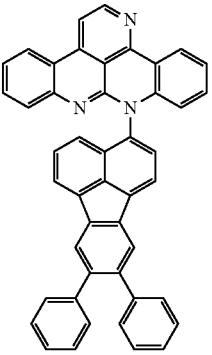 [SMILES: c1ccc(-c2cc3c(cc2-c2ccccc2)-c2ccc(N4c5ccccc5-c5nccc6c5c4nc4ccccc46)c4cccc-3c24)cc1] | 77% |
| 4o | 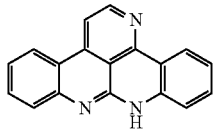 [SMILES: c1ccc2c(c1)Nc1nc3ccccc3c3ccnc-2c13] | 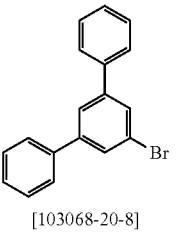 [SMILES: Brc1cc(-c2ccccc2)cc(-c2ccccc2)c1]  [103068-20-8] | 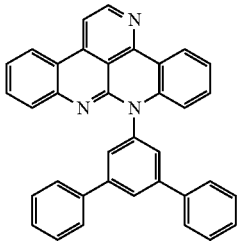 [SMILES: c1ccc(-c2cc(-c3ccccc3)cc(N3c4ccccc4-c4nccc5c4c3nc3ccccc35)c2)cc1] | 72% |
| 5o | 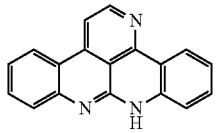 [SMILES: c1ccc2c(c1)Nc1nc3ccccc3c3ccnc-2c13] | 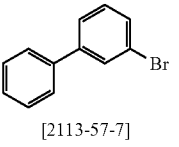 [SMILES: Brc1cccc(-c2ccccc2)c1]  [2113-57-7] | 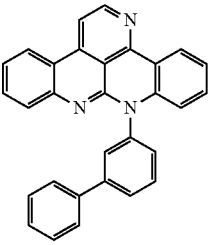 [SMILES: c1ccc(-c2cccc(N3c4ccccc4-c4nccc5c4c3nc3ccccc35)c2)cc1] | 63% |

-continued
| | Reactant 1 | Reactant 2 | Product | Yield |
|---|---|---|---|---|
| 6o | 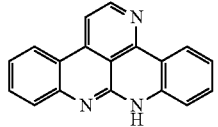 [SMILES: c1ccc2c(c1)Nc1nc3ccccc3c3ccnc-2c13] | 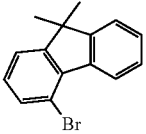 [942615-32-9] | 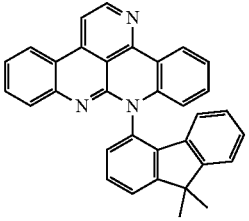 [SMILES: CC1(C)c2ccccc2-c2c(N3c4ccccc4-c4nccc5c4c3nc3ccccc35)cccc21] | 52% |
| 7o | 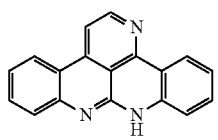 [SMILES: c1ccc2c(c1)Nc1nc3ccccc3c3ccnc-2c13] | 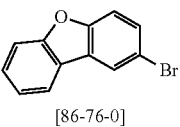 [SMILES: Brc1ccc2oc3ccccc3c2c1] [86-76-0] | 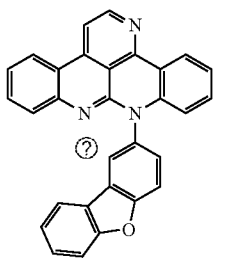 [SMILES: c1ccc2c(c1)-c1nccc3c1c(nc1ccccc13)N2c1ccc2oc3ccccc3c2c1] | 81% |
| 8o | 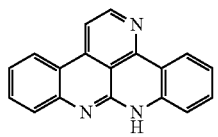 [SMILES: c1ccc2c(c1)Nc1nc3ccccc3c3ccnc-2c13] | 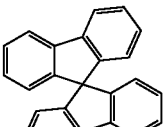 [1161009-88-6] | 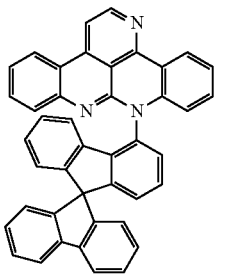 [SMILES: c1ccc2c(c1)-c1nccc3c1c(nc1ccccc13)N2c1cccc2c1-c1ccccc1C21c2ccccc2-c2ccccc21] | 84% |
| 9o | 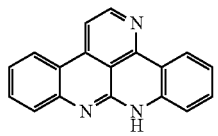 [SMILES: c1ccc2c(c1)Nc1nc3ccccc3c3ccnc-2c13] | 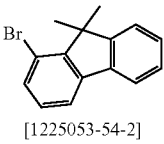 [1225053-54-2] | 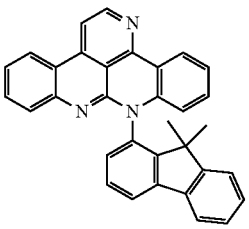 [SMILES: CC1(C)c2ccccc2-c2cccc(N3c4ccccc4-c4nccc5c4c3nc3ccccc35)c21] | 87% |
| 10o | 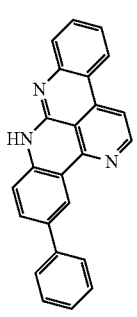 [SMILES: c1ccc(-c2ccc3c(c2)-c2nccc4c2c(nc2ccccc24)N3)cc1] | 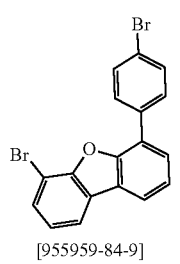 [SMILES: Brc1ccc(-c2cccc3c2oc2c(Br)cccc23)cc1] [955959-84-9] | 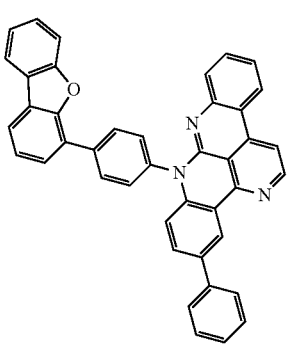 [SMILES: c1ccc(-c2ccc3c(c2)-c2nccc4c2c(nc2ccccc24)N3c2ccc(-c3cccc4c3oc3ccccc34)cc2)cc1] | 80% |

-continued

| | Reactant 1 | Reactant 2 | Product | Yield |
|---|---|---|---|---|
| 11o | | | | 78% |
| 12o | | | | 77% |
| 13o | | | | 79% |
| 14o | | | | 60% |

| | Reactant 1 | Reactant 2 | Product | Yield |
|---|---|---|---|---|
| 15o | | [30169-34-7] | | 61% |
| 16o | | [760212-40-8] | | 68% |
| 17o | | CAS 1153-85-1 | | 65% |
| 18o | | CAS 57102-42-8 | | 62% |
p) 9-(4,6-Diphenylpyridin-2-yl)-9H-1,8,9-triaz-abenzo[fg]naphthacene
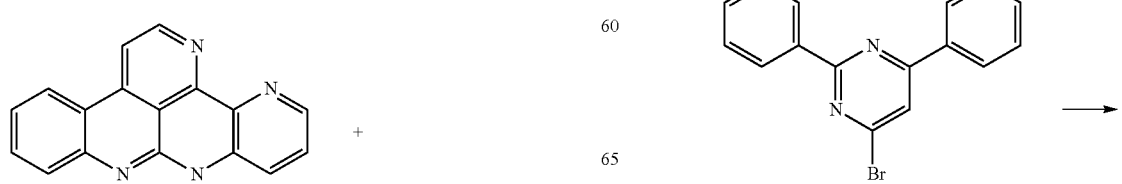

-continued

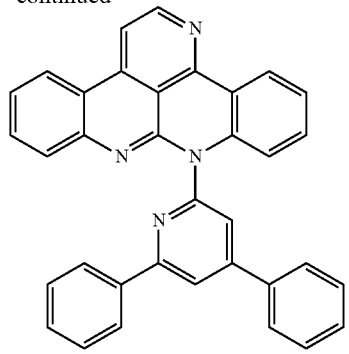

16 g (60 mmol) of 9H-1,8,9-triazabenzo[fg]naphthacene are dissolved in 300 ml of dimethylformamide under protective gas atmosphere, and 3 g of NaH, 60% in mineral oil, (75 mmol) are added. After 1 h at room temperature, a solution of 19 g (62 mmol) of 4-bromo-2,6-diphenylpyrimidine in 150 ml of dimethylformamide is added dropwise. The reaction mixture is stirred at room temperature for 12 h. After this time, the reaction mixture is poured onto ice and extracted three times with dichloromethane. The combined organic phases are dried over $Na_2SO_4$ and concentrated. The residue is recrystallized from toluene and finally fractionally sublimed twice (p about $10^{-6}$ mbar, T=330-360° C.). Yield: 23 g, 80% of theory; purity: 99.9% by HPLC.

The following compounds are prepared in an analogous manner:

| | Reactant 1 | Reactant 2 | Product | Yield |
|---|---|---|---|---|
| 1p | | [1403252-59-4] | | 76% |
| 2p | | | | 77% |
| 3p | | [29874-83-7] | | 82% |
| 4p | | [6484-25-9] | | 67% |

-continued

| | Reactant 1 | Reactant 2 | Product | Yield |
|---|---|---|---|---|
| 5p | | [1292317-90-8] | | 87% |
| 6p | | [163053-24-6] | | 88% |
| 7p | | [1413376-86-9] | | 74% |
| 8p | | 2915-16-4 | | 75% |
| 9p | | [3842-55-5] | | 76% |

-continued

| | Reactant 1 | Reactant 2 | Product | Yield |
|---|---|---|---|---|
| 10p | | [3842-55-5] | | 81% |
| 11p | | [6484-25-9] | | 82% |
| 12p | | [1292317-90-8] | | 84% |
| 13p | | [1869142-00-6] | | 86% |

| Reactant 1 | Reactant 2 | Product | Yield |
|---|---|---|---|
| 14p | [1614244-72-2] | | 80% | q) 5-Bromo-9-thia-1,8-diazabenzo[fg]naphthacene

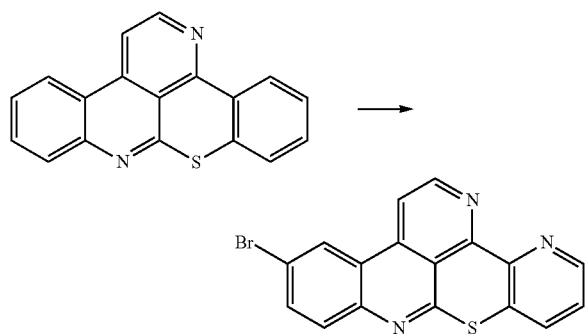

10.6 g (37.3 mmol) of 9-thia-1,8-diazabenzo[fg]naphthacene are initially charged in 80 ml of DMF. Subsequently, 13.3 g (74.6 mmol) of NBS are added in portions and the reaction mixture is stirred at 40° C. for 4 h. Subsequently, 15 ml of water are added to the mixture and extraction is effected with $CH_2Cl_2$. The organic phase is dried over $MgSO_4$ and the solvents are removed under reduced pressure. The product is subjected to extractive stirring with hot hexane and filtered off with suction. Yield: 11.4 g (31 mmol), 70% of theory, purity by $^1$H NMR about 97%.

The following compounds are prepared in an analogous manner:

| Reactant | Product | Yield |
|---|---|---|
| 1q | | 71% |
| 2q | | 68% |
| 3q | | 66% |

-continued

| | Reactant | Product | Yield |
|---|---|---|---|
| 4q | | | 67% | r) 5-[3-Eth-(Z)-ylidene-1-phenyl-2-prop-2-en-(E)-ylidene-2,3-dihydro-1H-indol-5-yl]-9-thin-1,8-diazabenzo[fg]naphthacene

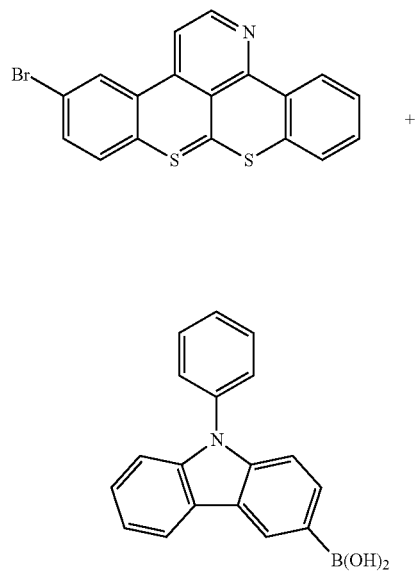

+

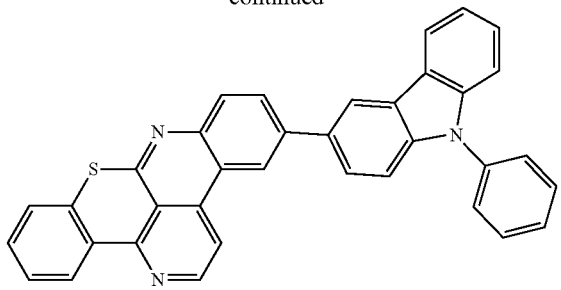

24 g (66 mmol) of 5-bromo-9-thia-1,8-diazabenzo[fg]naphthacene, 17 g (664 mmol) of 2-N-phenylcarbazole-3-boronic acid and 13.7 g (100 mmol) of sodium tetraborate are dissolved in 100 ml of THF and 60 ml of water and degassed. 0.91 g (1.3 mmol) of bis(triphenylphosphine) palladium(II) chloride and 1 g (20 mmol) of hydrazinium hydroxide are added. The reaction mixture is then stirred under a protective gas atmosphere at 70° C. for 48 h. The cooled solution is supplemented with toluene, washed repeatedly with water, dried and concentrated. The product is purified via column chromatography on silica gel with toluene/heptane (1:2). Yield: 29 g (55 mmol), 84% of theory.

The following compounds are prepared in an analogous manner:

| | Reactant 1 | Reactant 2 | Product | Yield |
|---|---|---|---|---|
| 1r | | | | 80% |

[1572537-51-1]

-continued

| | Reactant 1 | Reactant 2 | Product | Yield |
|---|---|---|---|---|
| 2r | | | | 78% |
| 3r | | | | 76% |
| 4r | [326852-72-6] | | | 81% |
| 5r | | [1001911-63-2] | | 76% |
| 6r | | [1642121-58-1] | | 79% |

| Reactant 1 | Reactant 2 | Product | Yield |
|---|---|---|---|
| 7r | [1642121-58-1] | | 69% |
| 8r | | | 66% |

Production of the OLEDs

Examples I1 to I21 which follow (see table 1) present the use of the materials of the invention in OLEDs.

Pretreatment for Examples I1-I21:

Glass plaques coated with structured ITO (indium tin oxide) of thickness 50 nm are treated prior to coating, first with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1. The materials required for production of the OLEDs are shown in Table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:IC2:TER1 (50%:45%:5%) mean here that the material IC1 is present in the layer in a proportion by volume of 50%, IC2 in a proportion by volume of 45% and TER1 in a proportion by volume of 5%. Analogously, the electron transport layer may also consist of a mixture of two materials.

The OLEDs are characterized in a standard manner. The electroluminescence spectra are determined at a luminance of 1000 cd/m$^2$, and the CIE 1931 x and y color coordinates are calculated therefrom.

Use of Materials of the Invention in OLEDs

The materials of the invention can be used in the emission layer in red-phosphorescing OLEDs. The inventive compounds IV1 to IV21 are used in Examples I1 to I21 as matrix material in the emission layer. The color coordinates of the electroluminescence spectra of the OLEDs are CIEx=0.67 and CIEy=0.33. The materials are thus suitable for use in the emission layer of red OLEDs.

In addition, the materials of the invention can be used successfully in the hole blocker layer (HBL) or electron blocker layer (EBL). This is shown in experiments I9 and I21. Here too, the color coordinates of the spectrum of each of the OLEDs are CIEx=0.67 and CIEy=0.33.

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| I1 | HATCN 5 nm | SpMA1 125 nm | SpMA2 10 nm | IC1:IV1:TER1 (50%:45%:5%) 40 nm | — | ST1:LiQ (50%:50%) 35 nm | — |
| I2 | HATCN 5 nm | SpMA1 125 nm | SpMA2 10 nm | IC1:IV2:TER1 (50%:45%:5%) 40 nm | — | ST1:LiQ (50%:50%) 35 nm | — |
| I3 | HATCN 5 nm | SpMA1 125 nm | SpMA2 10 nm | IC1:IV3:TER1 (50%:45%:5%) 40 nm | — | ST1:LiQ (50%:50%) 35 nm | — |
| I4 | HATCN 5 nm | SpMA1 125 nm | SpMA2 10 nm | IC1:IV4:TER1 (50%:45%:5%) 40 nm | — | ST1:LiQ (50%:50%) 35 nm | — |
| I5 | HATCN 5 nm | SpMA1 125 nm | SpMA2 10 nm | IC1:IV5:TER1 (50%:45%:5%) 40 nm | — | ST1:LiQ (50%:50%) 35 nm | — |

TABLE 1-continued

Structure of the OLEDs

| Ex. | HIL thickness | HTL thickness | EBL thickness | EML thickness | HBL thickness | ETL thickness | EIL thickness |
|---|---|---|---|---|---|---|---|
| I6 | HATCN 5 nm | SpMA1 125 nm | SpMA2 10 nm | IV6:TER1 (95%:5%) 40 nm | — | ST1:LiQ (50%:50%) 35 nm | — |
| I7 | HATCN 5 nm | SpMA1 125 nm | SpMA2 10 nm | IC1:IV7:TER1 (50%:45%:5%) 40 nm | — | ST1:LiQ (50%:50%) 35 nm | — |
| I8 | HATCN 5 nm | SpMA1 125 nm | SpMA2 10 nm | IC1:IV8:TER1 (50%:45%:5%) 40 nm | — | ST1:LiQ (50%:50%) 35 nm | — |
| I9 | HATCN 5 nm | SpMA1 125 nm | SpMA2 10 nm | IV9:TER1 (95%:5%) 40 nm | IV9 5 nm | ST1:LiQ (50%:50%) 30 nm | — |
| I10 | HATCN 5 nm | SpMA1 125 nm | SpMA2 10 nm | IV10:TER1 (95%:5%) 40 nm | — | ST1:LiQ (50%:50%) 35 nm | — |
| I11 | HATCN 5 nm | SpMA1 125 nm | SpMA2 10 nm | IC1:IV11:TER1 (50%:45%:5%) 40 nm | — | ST1:LiQ (50%:50%) 35 nm | — |
| I12 | HATCN 5 nm | SpMA1 125 nm | SpMA2 10 nm | IV12:TER1 (95%:5%) 40 nm | — | ST1:LiQ (50%:50%) 35 nm | — |
| I13 | HATCN 5 nm | SpMA1 125 nm | SpMA2 10 nm | IV13:TER1 (95%:5%) 40 nm | — | ST1:LiQ (50%:50%) 35 nm | — |
| I14 | HATCN 5 nm | SpMA1 125 nm | SpMA2 10 nm | IC2:IV14:TER1 (50%:45%:5%) 40 nm | — | ST1:LiQ (50%:50%) 35 nm | — |
| I15 | HATCN 5 nm | SpMA1 125 nm | SpMA2 10 nm | IV15:TER1 (95%:5%) 40 nm | — | ST1:LiQ (50%:50%) 35 nm | — |
| I16 | HATCN 5 nm | SpMA1 125 nm | SpMA2 10 nm | IV16:TER1 (95%:5%) 40 nm | — | ST1:LiQ (50%:50%) 35 nm | — |
| I17 | HATCN 5 nm | SpMA1 125 nm | SpMA2 10 nm | IV17:TER1 (95%:5%) 40 nm | — | ST1:LiQ (50%:50%) 35 nm | — |
| I18 | HATCN 5 nm | SpMA1 125 nm | SpMA2 10 nm | IV18:TER1 (95%:5%) 40 nm | — | ST1:LiQ (50%:50%) 35 nm | — |
| I19 | HATCN 5 nm | SpMA1 125 nm | SpMA2 10 nm | IC2:IV19:TER1 (50%:45%:5%) 40 nm | — | ST1:LiQ (50%:50%) 35 nm | — |
| I20 | HATCN 5 nm | SpMA1 125 nm | SpMA2 10 nm | IV20:TER1 (95%:5%) 40 nm | — | ST1:LiQ (50%:50%) 35 nm | — |
| I21 | HATCN 5 nm | SpMA1 125 nm | EG21 10 nm | IC1:IV21:TER1 (50%:45%:5%) 40 nm | — | ST1:LiQ (50%:50%) 35 nm | — |

TABLE 2

Structural formulae of the materials for the OLEDs

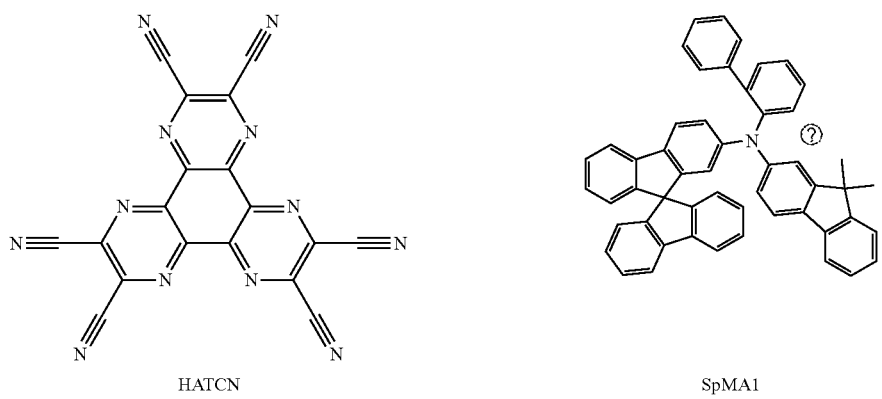

HATCN                SpMA1

TABLE 2-continued
Structural formulae of the materials for the OLEDs
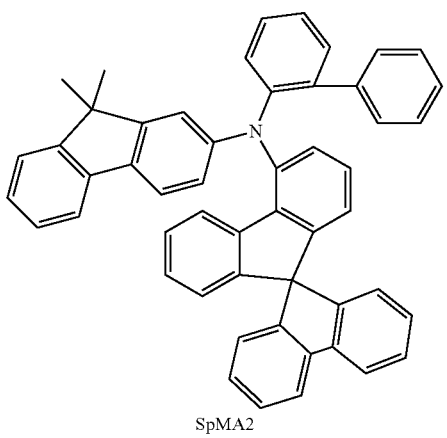
SpMA2
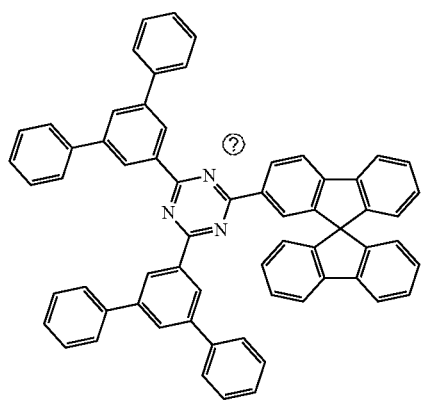 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST1
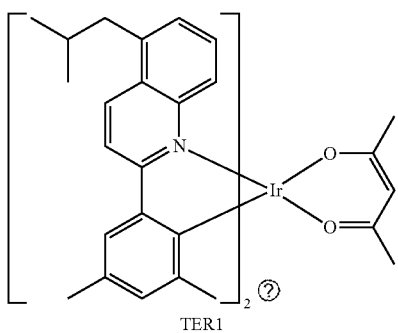
TER1
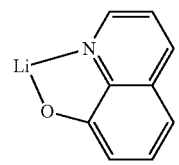
LiQ
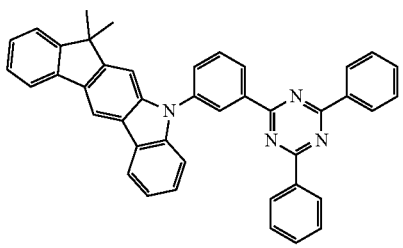 [SMILES: CC1(C)c2ccccc2-c2cc3c4ccccc4n(-c4cccc(-c5nc(-c6ccccc6)nc(-c6ccccc6)n5)c4)c3cc21]
IC1
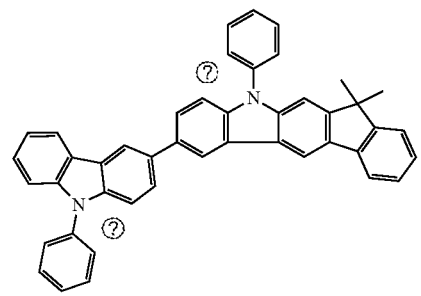 [SMILES: CC1(C)c2ccccc2-c2cc3c4cc(-c5ccc6c(c5)c5ccccc5n6-c5ccccc5)ccc4n(-c4ccccc4)c3cc21]
IC2
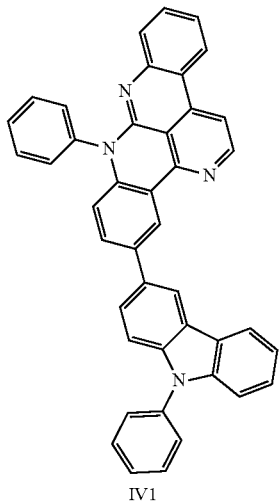
IV1
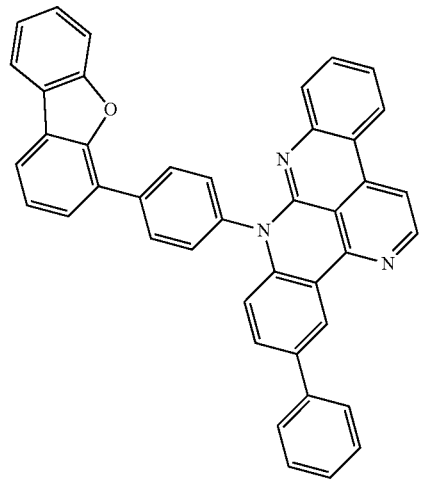 [SMILES: c1ccc(-c2ccc3c(c2)-c2nccc4c2c(nc2ccccc24)N3c2ccc(-c3cccc4c3oc3ccccc34)cc2)cc1]
IV2

TABLE 2-continued
Structural formulae of the materials for the OLEDs
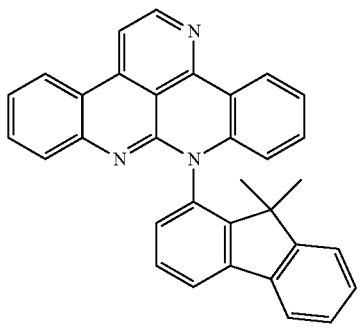 [SMILES: CC1(C)c2ccccc2-c2cccc(N3c4ccccc4-c4nccc5c4c3nc3ccccc35)c21]
IV3
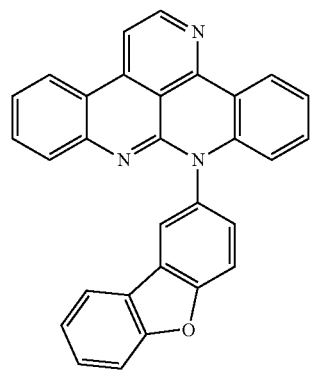 [SMILES: c1ccc2c(c1)-c1nccc3c1c(nc1ccccc13)N2c1ccc2oc3ccccc3c2c1]
IV4
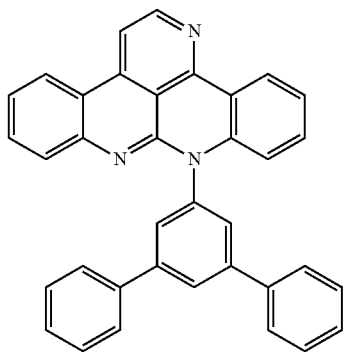 [SMILES: c1ccc(-c2cc(-c3ccccc3)cc(N3c4ccccc4-c4nccc5c4c3nc3ccccc35)c2)cc1]
IV5
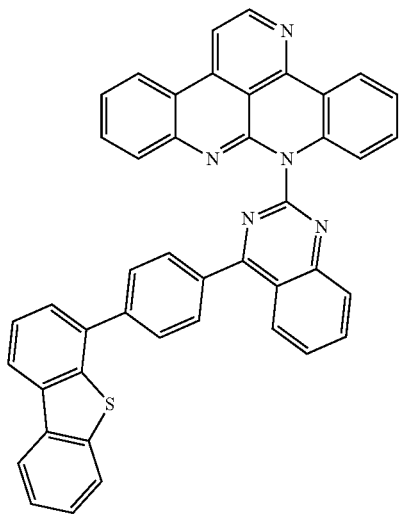 [SMILES: c1ccc2c(c1)-c1nccc3c1c(nc1ccccc13)N2c1nc(-c2ccc(-c3cccc4c3sc3ccccc34)cc2)c2ccccc2n1]
IV6
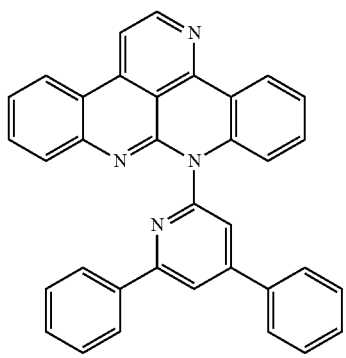 [SMILES: c1ccc(-c2cc(-c3ccccc3)nc(N3c4ccccc4-c4nccc5c4c3nc3ccccc35)c2)cc1]
IV7
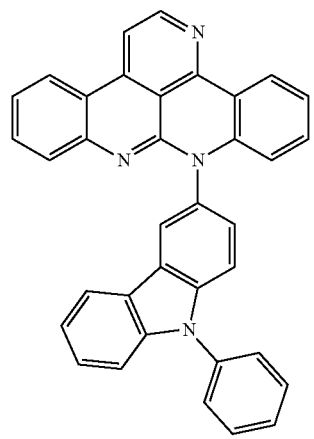 [SMILES: c1ccc(-n2c3ccccc3c3cc(N4c5ccccc5-c5nccc6c5c4nc4ccccc46)ccc32)cc1]
IV8

TABLE 2-continued
Structural formulae of the materials for the OLEDs
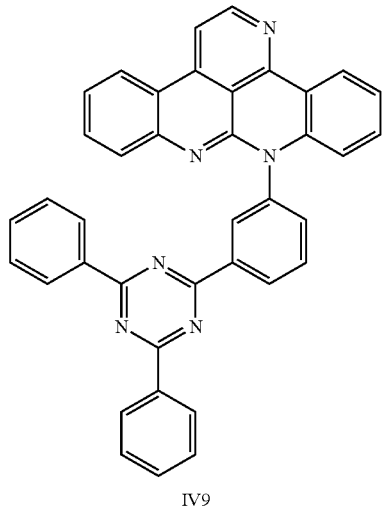
IV9
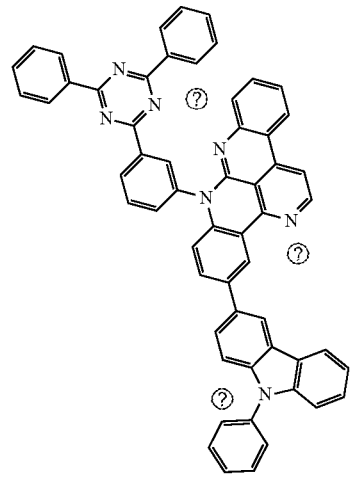 [SMILES: c1ccc(-c2nc(-c3ccccc3)nc(-c3cccc(N4c5ccc(-c6ccc7c(c6)c6ccccc6n7-c6ccccc6)cc5-c5nccc6c5c4nc4ccccc46)c3)n2)cc1]
IV10
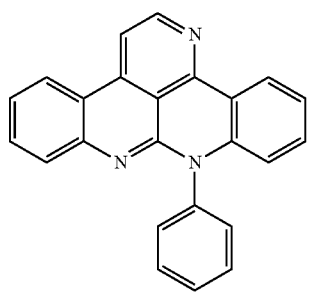 [SMILES: c1ccc(N2c3ccccc3-c3nccc4c3c2nc2ccccc24)cc1]
IV11
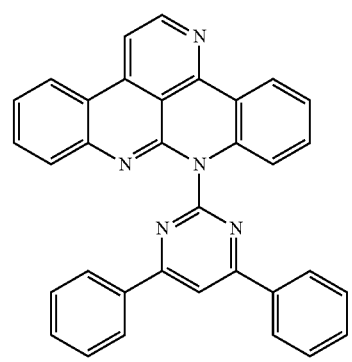 [SMILES: c1ccc(-c2cc(-c3ccccc3)nc(N3c4ccccc4-c4nccc5c4c3nc3ccccc35)n2)cc1]
IV12
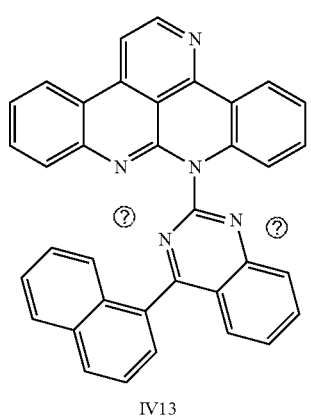
IV13
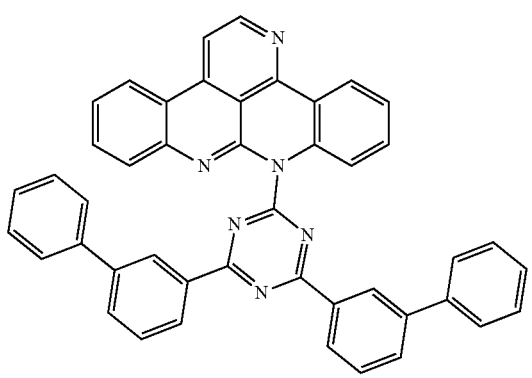 [SMILES: c1ccc(-c2cccc(-c3nc(-c4cccc(-c5ccccc5)c4)nc(N4c5ccccc5-c5nccc6c5c4nc4ccccc46)n3)c2)cc1]
IV14

TABLE 2-continued
Structural formulae of the materials for the OLEDs
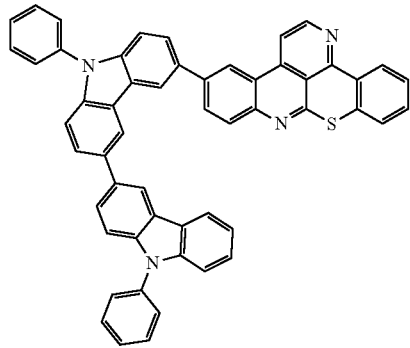 [SMILES: c1ccc(-n2c3ccccc3c3cc(-c4ccc5c(c4)c4cc(-c6ccc7nc8c9c(nccc9c7c6)-c6ccccc6S8)ccc4n5-c4ccccc4)ccc32)cc1]
IV15
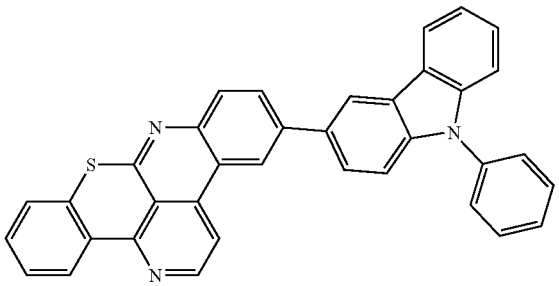 [SMILES: c1ccc(-n2c3ccccc3c3cc(-c4ccc5nc6c7c(nccc7c5c4)-c4ccccc4S6)ccc32)cc1]
IV16
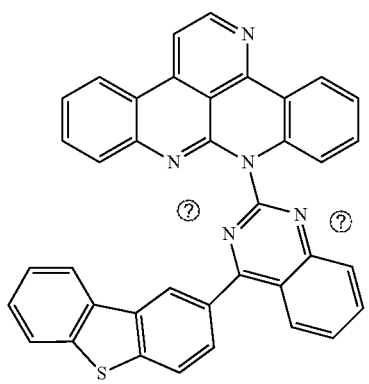 [SMILES: c1ccc2c(c1)-c1nccc3c1c(nc1ccccc13)N2c1nc(-c2ccc3sc4ccccc4c3c2)c2ccccc2n1]
IV17
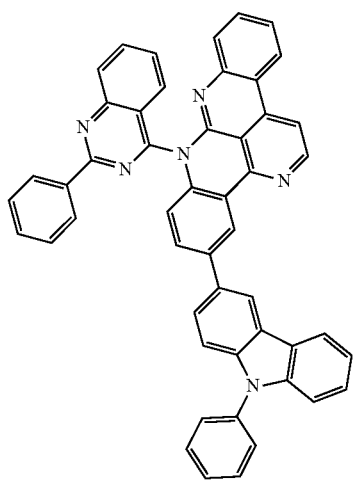 [SMILES: c1ccc(-c2nc(N3c4ccc(-c5ccc6c(c5)c5ccccc5n6-c5ccccc5)cc4-c4nccc5c4c3nc3ccccc35)c3ccccc3n2)cc1]
IV18
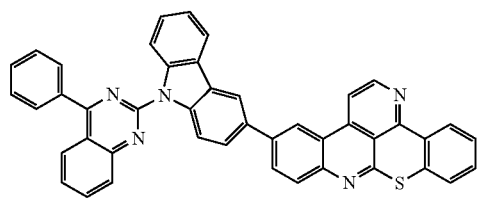 [SMILES: c1ccc(-c2nc(-n3c4ccccc4c4cc(-c5ccc6nc7c8c(nccc8c6c5)-c5ccccc5S7)ccc43)nc3ccccc23)cc1]
IV19
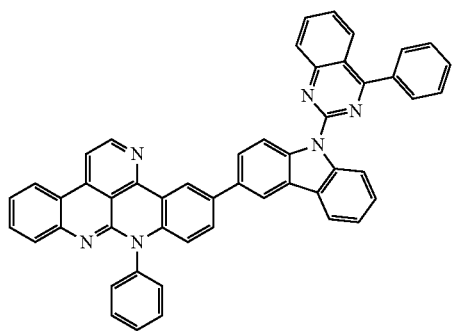 [SMILES: c1ccc(-c2nc(-n3c4ccccc4c4cc(-c5ccc6c(c5)-c5nccc7c5c(nc5ccccc57)N6c5ccccc5)ccc43)nc3ccccc23)cc1]
IV20
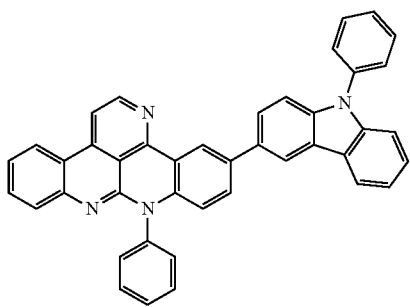 [SMILES: c1ccc(N2c3ccc(-c4ccc5c(c4)c4ccccc4n5-c4ccccc4)cc3-c3nccc4c3c2nc2ccccc24)cc1]
IV21

The invention claimed is:
1. A compound of formula (1)

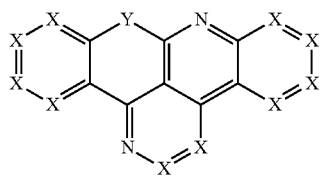

Formula (1)

where the symbols and indices used are as follows:
X is the same or different at each instance and is CR or N;
Y is NR', C(R")$_2$, C=O, BR', O or S;
R, R" are the same or different at each instance and are H, D, F, Cl, Br, I, N(R$^1$)$_2$, NAr$_2$, CN, NO$_2$, OR$^1$, SR$^1$, COOR$^1$, C(=O)N(R$^1$)$_2$, Si(R$^1$)$_3$, B(OR$^1$)$_2$, C(=O)R$^1$, P(=O)(R$^1$)$_2$, S(=O)R$^1$, S(=O)$_2$R$^1$, OSO$_2$R$^1$, a straight-chain alkyl group having 1 to 20 carbon atoms or an alkenyl or alkynyl group having 2 to 20 carbon atoms or a branched or cyclic alkyl group having 3 to 20 carbon atoms and where the alkyl, alkenyl or alkynyl group may in each case be substituted by one or more R$^1$ radicals, where one or more nonadjacent CH$_2$ groups may be replaced by Si(R$^1$)$_2$, C=O, NR$^1$, O, S or CONR$^1$, or an aromatic or heteroaromatic ring system which has 5 to 60 aromatic ring atoms and may be substituted in each case by one or more R$^1$ radicals; at the same time, two R radicals together may also form an aliphatic or heteroaliphatic ring system; in addition, two R" radicals together may also form an aliphatic, heteroaliphatic, aromatic or heteroaromatic ring system;
R' is an aromatic or heteroaromatic ring system which has 5 to 40 aromatic ring atoms and may be substituted by one or more R$^1$ radicals;
Ar is the same or different at each instance and is an aromatic or heteroaromatic ring system which has 5 to 40 aromatic ring atoms and may be substituted by one or more R$^1$ radicals;
R$^1$ is the same or different at each instance and is H, D, F, Cl, Br, I, N(R$^2$)$_2$, CN, NO$_2$, OR$^2$, SR$^2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more R$^2$ radicals and where one or more nonadjacent CH$_2$ groups may be replaced by Si(R$_2$)$^2$, C=O, NR$^2$, O, S or CONR$^2$, or an aromatic or heteroaromatic ring system which has 5 to 40 aromatic ring atoms and may be substituted in each case by one or more R$^2$ radicals; at the same time, two or more R$^1$ radicals together may form a ring system;
R$^2$ is the same or different at each instance and is H, D, F or an aliphatic, aromatic or heteroaromatic organic radical having 1 to 20 carbon atoms, in which one or more hydrogen atoms may also be replaced by F;
with the proviso that the compound of the formula (1) contains at least one substituent R' and/or that the compound of the formula (1) contains at least one substituent R selected from the group consisting of NAr$_2$ and an aromatic or heteroaromatic ring system which has 5 to 60 aromatic ring atoms and may be substituted by one or more R$^1$ radicals;

where the following compounds are excluded from the invention:

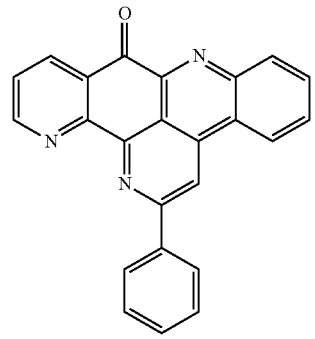

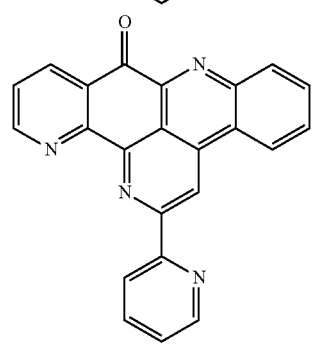

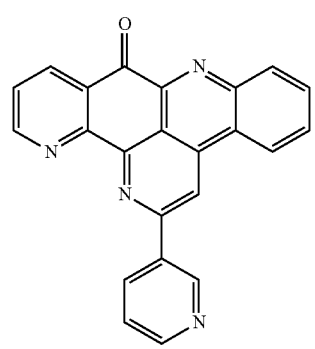

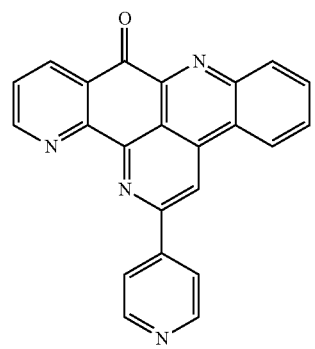

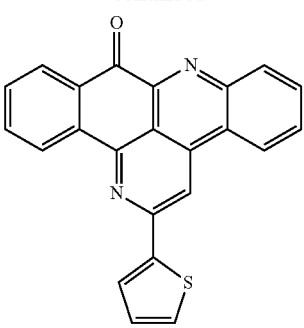
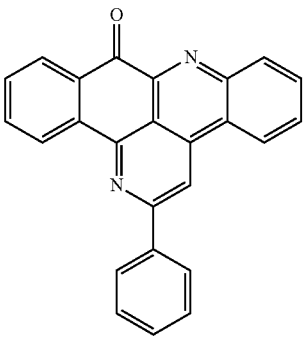
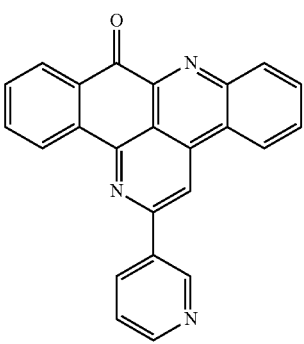
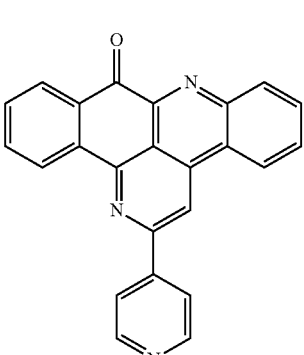
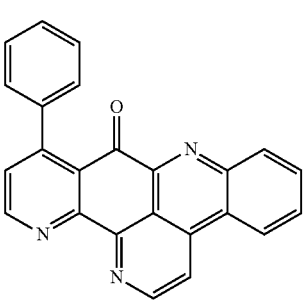
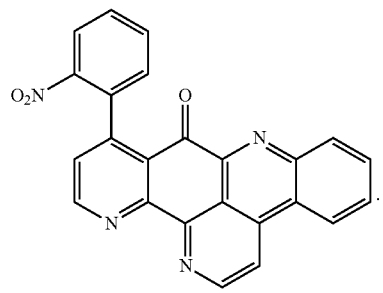
2. The compound as claimed in claim 1, characterized in that Y is NR', O or S.
3. The compound as claimed in claim 1, characterized in that the compound contains not more than two nitrogen atoms per ring.
4. The compound as claimed in claim 1, wherein the compound is of one of the formulae (2a) to (2k)
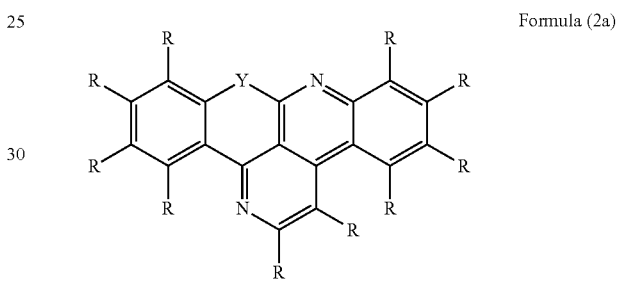
Formula (2a)
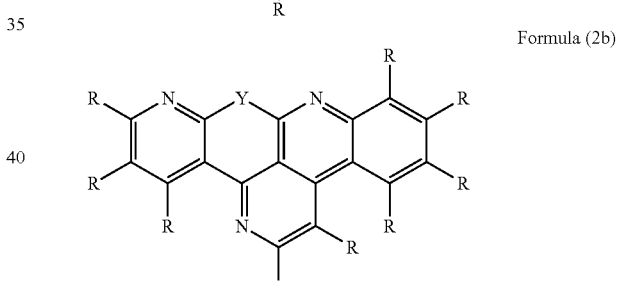
Formula (2b)
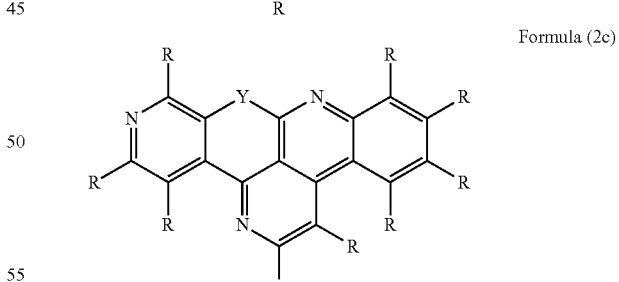
Formula (2c)
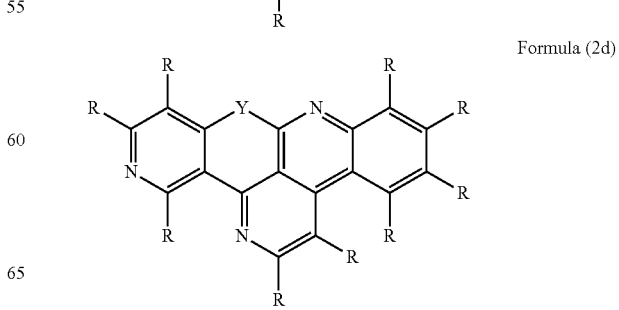
Formula (2d)

-continued

Formula (2e)
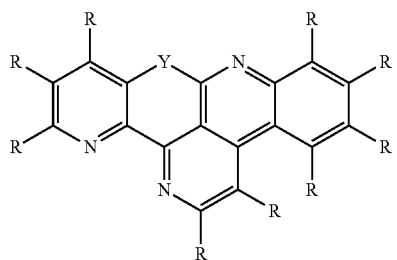

Formula (2f)
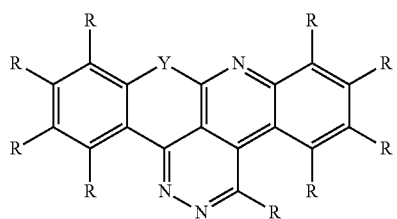

Formula (2g)
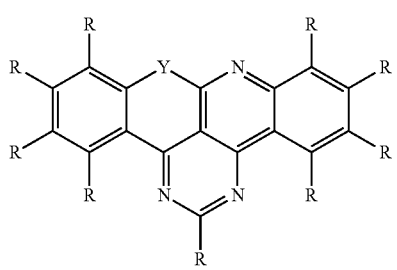

Formula (2h)
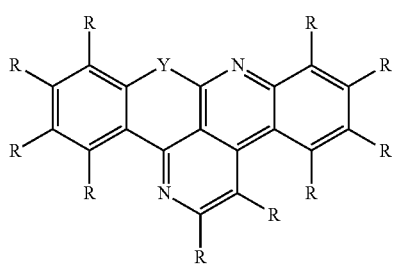

Formula (2i)
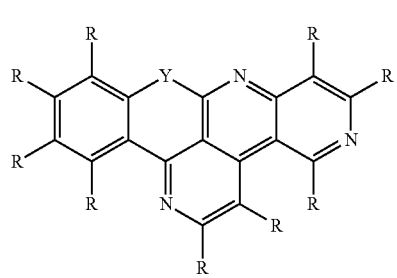

Formula (2j)
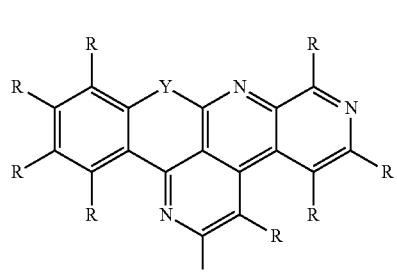

-continued

Formula (2k)
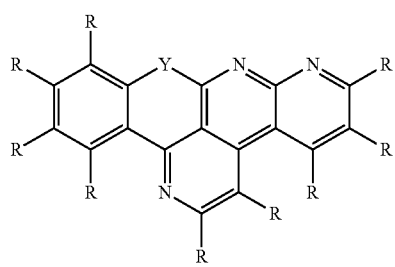

where the symbols used have the definitions given in claim 1.

5. The compound as claimed in claim 1, wherein the compound is of one of the formulae (2a') and (2a")

Formula (2a')
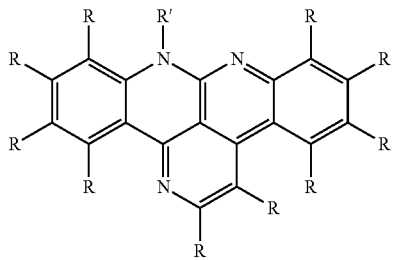

Formula (2a")
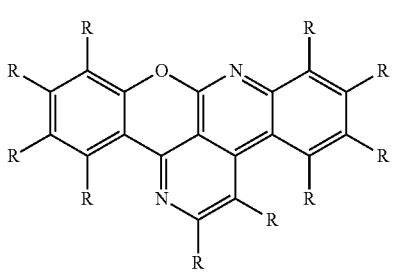

where R and R' have the definitions given in claim 1 and at least one R group in formula (2a") is selected from the group consisting of NAr$_2$ and an aromatic or heteroaromatic ring system.

6. The compound as claimed in claim 1, wherein the compound is of formula (3)

Formula (3)
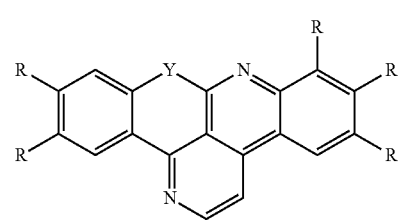

where the symbols used have the definitions given in claim 1.

7. The compound as claimed in claim 1, wherein the compound is of formula (5) or formula (6)

Formula (5)

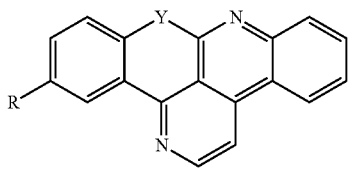

Formula (6)

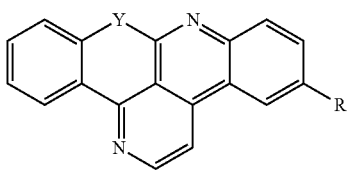

where the symbols used have the definitions given in claim 1.

8. The compound as claimed in claim 1, wherein the compound is of one of the formulae (5'), (5"), (6') and (6")

Formula (5')

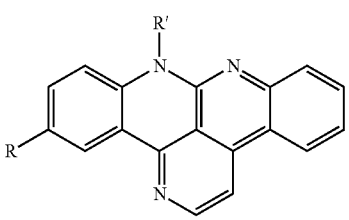

Formula (5")

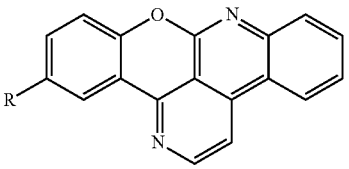

Formula (6')

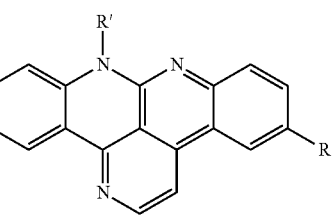

Formula (6")

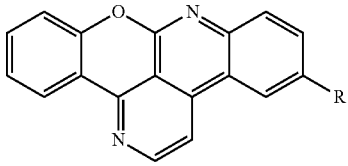

where R and R' have the definitions given in claim 1 and the R group in the formulae (5") and (6") is selected from the group consisting of $NAr_2$ and an aromatic or heteroaromatic ring system.

9. The compound as claimed in claim 1, characterized in that R or R' or Ar', when they are aromatic or heteroaromatic ring systems, are selected from phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, phenanthrene, triphenylene or a combination of two or three of these groups, each of which may be substituted by one or more $R^1$ radicals.

10. A formulation comprising at least one compound as claimed in claim 1 and at least one further compound, where the further compound is one or more solvents and/or a further organic or inorganic compound.

11. An electronic device comprising at least one compound as claimed in claim 1.

12. An organic electroluminescent device, characterized in that the compound as claimed in claim 1, is used as matrix material for phosphorescent emitters and/or in an electron transport layer and/or in a hole blocker layer.

\* \* \* \* \*